(12) United States Patent
Nakamura et al.

(10) Patent No.: US 7,691,577 B2
(45) Date of Patent: Apr. 6, 2010

(54) PROTEIN HAVING AN EGF-LIKE REPEAT SEQUENCE

(75) Inventors: Noriko Nakamura, Fujisawa (JP); Tetsuo Sudo, Fujisawa (JP); Takatoshi Yamada, Urayasu (JP)

(73) Assignee: Toray Industries, Inc., Tokyo (JP)

( * ) Notice: Subject to any disclaimer, the term of this patent is extended or adjusted under 35 U.S.C. 154(b) by 456 days.

(21) Appl. No.: 11/475,860

(22) Filed: Jun. 28, 2006

(65) Prior Publication Data

US 2010/0047769 A1   Feb. 25, 2010

Related U.S. Application Data

(63) Continuation-in-part of application No. 11/219,698, filed on Sep. 7, 2005, now abandoned, which is a continuation of application No. 10/959,996, filed on Oct. 8, 2004, now abandoned, which is a continuation of application No. 10/795,402, filed on Mar. 9, 2004, now abandoned, which is a continuation of application No. 10/404,841, filed on Apr. 2, 2003, now abandoned.

(60) Provisional application No. 60/369,318, filed on Apr. 3, 2002.

(30) Foreign Application Priority Data

May 17, 2006   (JP) .............................. 2006-138094

(51) Int. Cl.
*C12N 15/11*   (2006.01)
*C12N 15/63*   (2006.01)
*C12N 5/10*   (2006.01)
*C12Q 1/68*   (2006.01)

(52) U.S. Cl. .................... 435/6; 435/320.1; 435/325; 435/252.3; 536/24.1

(58) Field of Classification Search ................... None
See application file for complete search history.

(56) References Cited

U.S. PATENT DOCUMENTS

2003/0224477 A1 * 12/2003 Heartlein et al. ........... 435/69.1

OTHER PUBLICATIONS

GenBank Accession No. AC124669 (Feb. 2004).*

* cited by examiner

*Primary Examiner*—Rebecca Prouty
(74) *Attorney, Agent, or Firm*—Birch, Stewart, Kolasch & Birch, LLP

(57) ABSTRACT

The present invention provides SELF protein having controlling effects on growth and differentiation of undifferentiated cells, wherein the protein contains a novel EGF-like repeat sequence, SELF gene encoding the same, a recombinant vector and a transformed cell containing the SELF gene, a method for treatment or prophylaxis with SELF protein or a recombinant expression vector containing SELF gene, SELF promoter, a recombinant vector and a transformed cell containing SELF promoter, and a screening method using the transformed cell containing SELF promoter.

9 Claims, 11 Drawing Sheets
(5 of 11 Drawing Sheet(s) Filed in Color)

1   2

201 KDa
                ▬
117 KDa                114 KDa

82 KDa                 84.7 KDa

47 KDa                 48.0 KDa 32.5 KDa 25.7 KDa

FIG.4

SEQUENCE LISTING

```
<160> NUMBER OF SEQ ID NOS: 34

<210> SEQ ID NO 1
<211> LENGTH: 5245
<212> TYPE: DNA
<213> ORGANISM: Mus musculus
<220> FEATURE:
<221> NAME/KEY: misc_feature
<222> LOCATION: (4927)..(4927)
<223> OTHER INFORMATION: n is A, C, G or T
<220> FEATURE:
<221> NAME/KEY: CDS
<222> LOCATION: (157)..(4365)
<220> FEATURE:
<223> OTHER INFORMATION: Inventor: Nakamura, Noriko; Sudo, Tetsuo;
      Yamada, Takatoshi

<400> SEQUENCE: 1
gcccgggcag gtcgcagtcg tgcctcacgc cttcctaagc tgcgcgggtc tccggagtgc         60
gacgcgagct agcggaaggg aactgtgcgg ccagtcggtc gtgcggtgac tgcagccacc        120
tgcccgagcc ccgtggcccg ccctcagatc ccggcg atg cgc ctc ggc gcc gcc        174
                                         Met Arg Leu Gly Ala Ala
                                          1               5 tgg gcg ctg ctg ctg gcc gca gcc ctg ggg ctc ggg acg cgc ggg gtg        222
Trp Ala Leu Leu Leu Ala Ala Ala Leu Gly Leu Gly Thr Arg Gly Val
        10                  15                  20
```

-continued

| | |
|---|---|
| cgc gct gcc gtg gcc ctc gcc gac ttc tac ccg ttc ggc acg aag cgc<br>Arg Ala Ala Val Ala Leu Ala Asp Phe Tyr Pro Phe Gly Thr Lys Arg<br>        25                  30                  35 | 270 |
| ggc gac acc gtc acc ccg aag cag gac gac ggc ggc tca ggg ctg caa<br>Gly Asp Thr Val Thr Pro Lys Gln Asp Asp Gly Gly Ser Gly Leu Gln<br>    40                  45                  50 | 318 |
| cca ctc tcg gtg ccc ttt ccg ttc ttc ggc gcc gag cac tcc gga ctc<br>Pro Leu Ser Val Pro Phe Pro Phe Phe Gly Ala Glu His Ser Gly Leu<br>55                  60                  65                  70 | 366 |
| tac gtg aac aat aat ggg atc atc tcc ttc ctg aag gaa gtt tct cag<br>Tyr Val Asn Asn Asn Gly Ile Ile Ser Phe Leu Lys Glu Val Ser Gln<br>                75                  80                  85 | 414 |
| ttc acc ccc gtg gcc ttc ccc atc gcc aaa gac cgc tgt gtg gta gca<br>Phe Thr Pro Val Ala Phe Pro Ile Ala Lys Asp Arg Cys Val Val Ala<br>    90                  95                  100 | 462 |
| gcc ttc tgg gca gat gta gac aac cgg cgt gca ggt gat gtc tac tac<br>Ala Phe Trp Ala Asp Val Asp Asn Arg Arg Ala Gly Asp Val Tyr Tyr<br>                105                  110                  115 | 510 |
| cgg gag gcc acc gac cca gcc atg ctg aac aga gcc acg gag gac atc<br>Arg Glu Ala Thr Asp Pro Ala Met Leu Asn Arg Ala Thr Glu Asp Ile<br>120                  125                  130 | 558 |
| aga cgg tac ttt cct gag ctc ccg gac ttc tct gct acc tgg gtt ttt<br>Arg Arg Tyr Phe Pro Glu Leu Pro Asp Phe Ser Ala Thr Trp Val Phe<br>135                  140                  145                  150 | 606 |
| gtt gcg acc tgg tac cgt gtg acc ttc ttt gga ggc agc agc tct tcc<br>Val Ala Thr Trp Tyr Arg Val Thr Phe Phe Gly Gly Ser Ser Ser Ser<br>                155                  160                  165 | 654 |
| ccc gtt aac aca ttc caa act gta ctc atc acc gat ggc cga ttc tcc<br>Pro Val Asn Thr Phe Gln Thr Val Leu Ile Thr Asp Gly Arg Phe Ser<br>                170                  175                  180 | 702 |
| ttc acc atc ttc aac tat gag tcc atc ttg tgg act acc ggc aca cac<br>Phe Thr Ile Phe Asn Tyr Glu Ser Ile Leu Trp Thr Thr Gly Thr His<br>                185                  190                  195 | 750 |
| gcc agc agc ggg ggt gac act gat ggc ttg gga ggc att gca gcc cag<br>Ala Ser Ser Gly Gly Asp Thr Asp Gly Leu Gly Gly Ile Ala Ala Gln<br>          200                  205                  210 | 798 |
| gca ggt ttc aac gca ggt gat ggg cac cgc tac ttc aac atc ccc ggg<br>Ala Gly Phe Asn Ala Gly Asp Gly His Arg Tyr Phe Asn Ile Pro Gly<br>215                  220                  225                  230 | 846 |
| tcg cgc aca gca gac atg gct gag gtg gag acc acc acc aac gtg ggc<br>Ser Arg Thr Ala Asp Met Ala Glu Val Glu Thr Thr Thr Asn Val Gly<br>                235                  240                  245 | 894 |
| gtg ccc ggc cgc tgg gcg ttt aga atc gat gat gcc cag gtg cgc gtg<br>Val Pro Gly Arg Trp Ala Phe Arg Ile Asp Asp Ala Gln Val Arg Val<br>          250                  255                  260 | 942 |
| ggg ggc tgc ggc cat aca acc tct gtg tgc ctg gtc ctg cgt cca tgc<br>Gly Gly Cys Gly His Thr Thr Ser Val Cys Leu Val Leu Arg Pro Cys<br>          265                  270                  275 | 990 |
| ctc aat ggt ggc aag tgc att gat gac tgc gtc acg ggc aat ccc tct<br>Leu Asn Gly Gly Lys Cys Ile Asp Asp Cys Val Thr Gly Asn Pro Ser<br>280                  285                  290 | 1038 |
| tac acc tgt tcc tgt ctc gct ggc ttc aca ggc cgg aga tgc cac ctg<br>Tyr Thr Cys Ser Cys Leu Ala Gly Phe Thr Gly Arg Arg Cys His Leu<br>295                  300                  305                  310 | 1086 |
| gat gtg aac gag tgt gct tcc cac ccc tgt cag aat ggt ggg acc tgc<br>Asp Val Asn Glu Cys Ala Ser His Pro Cys Gln Asn Gly Gly Thr Cys<br>                315                  320                  325 | 1134 |
| acc cat ggt gtc aac agc ttc agc tgc cag tgc cca gcc ggc ttc aag<br>Thr His Gly Val Asn Ser Phe Ser Cys Gln Cys Pro Ala Gly Phe Lys<br>          330                  335                  340 | 1182 |

-continued

```
gga ccc acc tgt gaa tcg gcc caa tct ccg tgt gac aac aaa gta tgt    1230
Gly Pro Thr Cys Glu Ser Ala Gln Ser Pro Cys Asp Asn Lys Val Cys
        345                 350                 355 caa aat ggt ggc cag tgc cag gca gag agc agc tct gca gta tgt gtg    1278
Gln Asn Gly Gly Gln Cys Gln Ala Glu Ser Ser Ser Ala Val Cys Val
    360                 365                 370 tgt cag gct gga tac act ggg gcc acc tgt gag aca gat gtg gat gaa    1326
Cys Gln Ala Gly Tyr Thr Gly Ala Thr Cys Glu Thr Asp Val Asp Glu
375                 380                 385                 390 tgc agt tct gac cca tgc cag aat ggg gga tca tgt gtt gac ctg gtt    1374
Cys Ser Ser Asp Pro Cys Gln Asn Gly Gly Ser Cys Val Asp Leu Val
                395                 400                 405 gga aac tac agc tgt att tgt gtg gag ccc ttc gag gga cct cag tgt    1422
Gly Asn Tyr Ser Cys Ile Cys Val Glu Pro Phe Glu Gly Pro Gln Cys
            410                 415                 420 gag aca gga agc tac ctg gtg cct tca ccc tgc ctc tcc aac ccc tgc    1470
Glu Thr Gly Ser Tyr Leu Val Pro Ser Pro Cys Leu Ser Asn Pro Cys
        425                 430                 435 cag aac ggg ggc acc tgt gtg gat gct gat gag gga tac gtg tgt gaa    1518
Gln Asn Gly Gly Thr Cys Val Asp Ala Asp Glu Gly Tyr Val Cys Glu
    440                 445                 450 tgc cct gaa ggc ttc atg ggc ttg gac tgc aga gag agg atc ctc aat    1566
Cys Pro Glu Gly Phe Met Gly Leu Asp Cys Arg Glu Arg Ile Leu Asn
455                 460                 465                 470 gac tgt gac tgc cgg aac gga ggc aga tgc ctg ggt gcc aac acc acc    1614
Asp Cys Asp Cys Arg Asn Gly Gly Arg Cys Leu Gly Ala Asn Thr Thr
                475                 480                 485 ctc tgc cag tgt cct cca ggc ttc ttt ggg ctc ctc tgt gaa ttt gaa    1662
Leu Cys Gln Cys Pro Pro Gly Phe Phe Gly Leu Leu Cys Glu Phe Glu
            490                 495                 500 gtc aca gcc acg ccc tgc aac atg aac acg cag tgt cca gat gga ggc    1710
Val Thr Ala Thr Pro Cys Asn Met Asn Thr Gln Cys Pro Asp Gly Gly
        505                 510                 515 tac tgc atg gag tat ggc gga agc tac cta tgt gtc tgc cac aca gac    1758
Tyr Cys Met Glu Tyr Gly Gly Ser Tyr Leu Cys Val Cys His Thr Asp
    520                 525                 530 cac aac atc agc cac tct ctg cca tcc ccc tgc gac tca gac cct tgc    1806
His Asn Ile Ser His Ser Leu Pro Ser Pro Cys Asp Ser Asp Pro Cys
535                 540                 545                 550 ttt aat gga ggt tcc tgt gac gcc cac gag gac tcc tac acg tgc gag    1854
Phe Asn Gly Gly Ser Cys Asp Ala His Glu Asp Ser Tyr Thr Cys Glu
                555                 560                 565 tgc cct cgt gga ttc cac ggc agg cac tgt gag aaa gcc cgg cca cac    1902
Cys Pro Arg Gly Phe His Gly Arg His Cys Glu Lys Ala Arg Pro His
            570                 575                 580 ctg tgc agc tca ggg ccc tgc cgg aat gga ggc aca tgc aag gaa atg    1950
Leu Cys Ser Ser Gly Pro Cys Arg Asn Gly Gly Thr Cys Lys Glu Met
        585                 590                 595 ggc gac gag tac cgc tgc acc tgc cct tat aga ttc act ggg aga cac    1998
Gly Asp Glu Tyr Arg Cys Thr Cys Pro Tyr Arg Phe Thr Gly Arg His
    600                 605                 610 tgt gag att gga aag cca gac tcc tgt gcc tct ggc ccc tgt cat aat    2046
Cys Glu Ile Gly Lys Pro Asp Ser Cys Ala Ser Gly Pro Cys His Asn
615                 620                 625                 630 ggt ggg act tgt ttc cac tac att ggc aaa tac aag tgt gac tgc cct    2094
Gly Gly Thr Cys Phe His Tyr Ile Gly Lys Tyr Lys Cys Asp Cys Pro
                635                 640                 645 cca gga ttc tct gga cgg cac tgt gag ata gct ccc tca ccc tgc ttc    2142
Pro Gly Phe Ser Gly Arg His Cys Glu Ile Ala Pro Ser Pro Cys Phe
```

-continued

|  |  |  |  |  |  |  |  |  |  |  |  |  |  |  |  |
|---|---|---|---|---|---|---|---|---|---|---|---|---|---|---|---|
|  | 650 |  |  |  | 655 |  |  |  | 660 |  |  |  |  |  |  |

```
cgg agc cca tgt atg aat ggg ggt acc tgt gag gat cta ggg aca gat      2190
Arg Ser Pro Cys Met Asn Gly Gly Thr Cys Glu Asp Leu Gly Thr Asp
        665                 670                 675 ttc tcc tgc tac tgc cag cca ggg tat aca gga cac cgg tgt cag gca      2238
Phe Ser Cys Tyr Cys Gln Pro Gly Tyr Thr Gly His Arg Cys Gln Ala
        680                 685                 690 gag gtg gac tgt ggt cac cct gag gag gtg gag cat gct acc atg cgc      2286
Glu Val Asp Cys Gly His Pro Glu Glu Val Glu His Ala Thr Met Arg
695                 700                 705                 710 ttc aac gga act cac gtg ggc tca gtg gcc ctg tac aca tgt gag ccc      2334
Phe Asn Gly Thr His Val Gly Ser Val Ala Leu Tyr Thr Cys Glu Pro
                715                 720                 725 ggc ttc agc ctg agt gcc ctc agc cat ata cgt gtc tgt cag cca caa      2382
Gly Phe Ser Leu Ser Ala Leu Ser His Ile Arg Val Cys Gln Pro Gln
        730                 735                 740 ggg gtc tgg agc cag cct ccc cag tgc att gaa gta gat gag tgc cgg      2430
Gly Val Trp Ser Gln Pro Pro Gln Cys Ile Glu Val Asp Glu Cys Arg
        745                 750                 755 tct cag cca tgc ctg cac gga ggc tcc tgc cag gac ctc att gct gat      2478
Ser Gln Pro Cys Leu His Gly Gly Ser Cys Gln Asp Leu Ile Ala Asp
        760                 765                 770 tac cag tgc ctc tgc agc ccg ggg tat gaa gga gtc cac tgt gag cta      2526
Tyr Gln Cys Leu Cys Ser Pro Gly Tyr Glu Gly Val His Cys Glu Leu
775                 780                 785                 790 gag aca gat gag tgc caa gca cag cca tgc aga aat ggg ggc tcc tgc      2574
Glu Thr Asp Glu Cys Gln Ala Gln Pro Cys Arg Asn Gly Gly Ser Cys
                795                 800                 805 agg gac ctc ccc agg gct ttc atc tgc cag tgc cct gaa ggt ttt gtt      2622
Arg Asp Leu Pro Arg Ala Phe Ile Cys Gln Cys Pro Glu Gly Phe Val
        810                 815                 820 gga atc cac tgt gaa aca gag gtg gat gcc tgt gcc tcc agc ccc tgc      2670
Gly Ile His Cys Glu Thr Glu Val Asp Ala Cys Ala Ser Ser Pro Cys
        825                 830                 835 cag cac gga ggc cgg tgt gag gac ggt ggt ggg gcc tac ctg tgc gtg      2718
Gln His Gly Gly Arg Cys Glu Asp Gly Gly Gly Ala Tyr Leu Cys Val
        840                 845                 850 tgt cca gag ggc ttc ttt ggc tac aac tgt gag aca gtg agt gac ccc      2766
Cys Pro Glu Gly Phe Phe Gly Tyr Asn Cys Glu Thr Val Ser Asp Pro
855                 860                 865                 870 tgc ttc tct agc ccc tgt ggg agc cgc ggc tac tgc ttg gcc agc aac      2814
Cys Phe Ser Ser Pro Cys Gly Ser Arg Gly Tyr Cys Leu Ala Ser Asn
                875                 880                 885 ggg tcc cac agc tgt acc tgc aaa gtg ggc tac aca ggc aag gac tgc      2862
Gly Ser His Ser Cys Thr Cys Lys Val Gly Tyr Thr Gly Lys Asp Cys
        890                 895                 900 acc aaa gag ctc ctc cca cca aca gcc ctc agg gta gaa agg gtg gag      2910
Thr Lys Glu Leu Leu Pro Pro Thr Ala Leu Arg Val Glu Arg Val Glu
        905                 910                 915 gag agt ggg gtc tcc atc tcc tgg agt cca ccc gag ggc acc acg gcc      2958
Glu Ser Gly Val Ser Ile Ser Trp Ser Pro Pro Glu Gly Thr Thr Ala
        920                 925                 930 agg cag gtg ctg gat ggc tat gca gtc acc tat gcc tcg tcg gat gga      3006
Arg Gln Val Leu Asp Gly Tyr Ala Val Thr Tyr Ala Ser Ser Asp Gly
935                 940                 945                 950 tcg tcc cgg cgc aca gac ttt gtg gac cgg agc cgc tcc tct cac cag      3054
Ser Ser Arg Arg Thr Asp Phe Val Asp Arg Ser Arg Ser Ser His Gln
                955                 960                 965 ctt cgg gcc cta gca gcc ggc cgc gcc tac aat atc tcc gtt ttc tca      3102
```

```
Leu Arg Ala Leu Ala Ala Gly Arg Ala Tyr Asn Ile Ser Val Phe Ser
             970                 975                 980 gtc aag aga aac aca aac aac aaa aat gac atc agc agg cct gca gca        3150
Val Lys Arg Asn Thr Asn Asn Lys Asn Asp Ile Ser Arg Pro Ala Ala
             985                 990                 995 ctg ctc acc cgc acc cga ccc cgc cct ata gaa gac ttt gag gtc acc        3198
Leu Leu Thr Arg Thr Arg Pro Arg Pro Ile Glu Asp Phe Glu Val Thr
    1000                1005                1010 aac att tca gcc aat gcc atc tca gtg cag tgg gct ctt cac agg atc        3246
Asn Ile Ser Ala Asn Ala Ile Ser Val Gln Trp Ala Leu His Arg Ile
1015                1020                1025                1030 cag cac gcc act gtc agc agg gtc cgg gtg tcc atc ctc tac ccc gag        3294
Gln His Ala Thr Val Ser Arg Val Arg Val Ser Ile Leu Tyr Pro Glu
                1035                1040                1045 gcc tct gcg gtc cag tcc act gag gtg gac agg agt gtg gac cgc ctc        3342
Ala Ser Ala Val Gln Ser Thr Glu Val Asp Arg Ser Val Asp Arg Leu
            1050                1055                1060 aca ttt ggg gac ctg ctg cca ggg aga aga tac act gtg cgg cta acc        3390
Thr Phe Gly Asp Leu Leu Pro Gly Arg Arg Tyr Thr Val Arg Leu Thr
    1065                1070                1075 acc ctt agt ggg cct gga gga gct gaa tat cct acc gag agc ctg gct        3438
Thr Leu Ser Gly Pro Gly Gly Ala Glu Tyr Pro Thr Glu Ser Leu Ala
1080                1085                1090 tca gct cca ctg aac gtg tgg acc cgg cct ttg cca cca gca aac ctg        3486
Ser Ala Pro Leu Asn Val Trp Thr Arg Pro Leu Pro Pro Ala Asn Leu
1095                1100                1105                1110 act gcc tct cga gtc aca gct acc tct gcc cat atg gtc tgg gac acc        3534
Thr Ala Ser Arg Val Thr Ala Thr Ser Ala His Met Val Trp Asp Thr
                1115                1120                1125 ccc gct cca ggt atc tca ctg gag gct tat gtc atc aat gtg acc aca        3582
Pro Ala Pro Gly Ile Ser Leu Glu Ala Tyr Val Ile Asn Val Thr Thr
            1130                1135                1140 agt caa agt acc aag agc cgc tac atc ccc aat ggg aag ctg gtg tcc        3630
Ser Gln Ser Thr Lys Ser Arg Tyr Ile Pro Asn Gly Lys Leu Val Ser
        1145                1150                1155 tat aca gtg cgt gat ctg atg cca ggt cgg cgg tac cag ctc tca gtt        3678
Tyr Thr Val Arg Asp Leu Met Pro Gly Arg Arg Tyr Gln Leu Ser Val
    1160                1165                1170 aca gct gtg cag agc aca gag cag ggc cag ctg cac agt gag cct gca        3726
Thr Ala Val Gln Ser Thr Glu Gln Gly Gln Leu His Ser Glu Pro Ala
1175                1180                1185                1190 cac ctc tac atc atc acc tcc ccc agg gat ggc acc gac aga cgc tgg        3774
His Leu Tyr Ile Ile Thr Ser Pro Arg Asp Gly Thr Asp Arg Arg Trp
                1195                1200                1205 cac cat gga gga cac cac tca cgg atg ctc aga aac aga cca gcc cct        3822
His His Gly Gly His His Ser Arg Met Leu Arg Asn Arg Pro Ala Pro
            1210                1215                1220 gtg cgc ctg cct gag ctg cgc ctg ctc aat gac cac agt gcc cct gaa        3870
Val Arg Leu Pro Glu Leu Arg Leu Leu Asn Asp His Ser Ala Pro Glu
        1225                1230                1235 aca cca act cag tca tcc agg ttc tca gag ctt gta gat gga aga gga        3918
Thr Pro Thr Gln Ser Ser Arg Phe Ser Glu Leu Val Asp Gly Arg Gly
    1240                1245                1250 aga gtg agt gcc agg ttt ggt ggc ttg ccc agc aga gca gta act gtg        3966
Arg Val Ser Ala Arg Phe Gly Gly Leu Pro Ser Arg Ala Val Thr Val
1255                1260                1265                1270 aga tca caa ccc acc act ccg gtg cca ctc aag aac aca gag gcc cct        4014
Arg Ser Gln Pro Thr Thr Pro Val Pro Leu Lys Asn Thr Glu Ala Pro
                1275                1280                1285
```

-continued

```
gag cag gtc cat ctg gcc ctc cag cta ccc aag aac agc agc aaa gac    4062
Glu Gln Val His Leu Ala Leu Gln Leu Pro Lys Asn Ser Ser Lys Asp
        1290                1295                1300 aca gaa agt acc cct ggc agc tgt tca gaa gat gct tgt cag aat gga    4110
Thr Glu Ser Thr Pro Gly Ser Cys Ser Glu Asp Ala Cys Gln Asn Gly
    1305                1310                1315 ggc acc tgt gtc cca ggt gcc gat gcc cac agc tgt gac tgc agg cct    4158
Gly Thr Cys Val Pro Gly Ala Asp Ala His Ser Cys Asp Cys Arg Pro
1320                1325                1330 ggg ttc aaa ggc aga cac tgt gag ctt gcc tgt gaa aaa gtg ccc cgc    4206
Gly Phe Lys Gly Arg His Cys Glu Leu Ala Cys Glu Lys Val Pro Arg
1335                1340                1345                1350 ccc tgc aca cgg ctg ttc tct gag acc aag tca ttt cct gtc tgg gaa    4254
Pro Cys Thr Arg Leu Phe Ser Glu Thr Lys Ser Phe Pro Val Trp Glu
            1355                1360                1365 ggc gac atc tgc cac cat gtg tat aag aaa gtc tac aaa gtt cac cag    4302
Gly Asp Ile Cys His His Val Tyr Lys Lys Val Tyr Lys Val His Gln
        1370                1375                1380 gac gtg tgc ttt aag gag cgc tgc cag agc aca agc ctc agg aaa ccc    4350
Asp Val Cys Phe Lys Glu Arg Cys Gln Ser Thr Ser Leu Arg Lys Pro
    1385                1390                1395 aaa cag gaa aca aag taacagtcaa acactgaaga gatcttaagg aaatcattct    4405
Lys Gln Glu Thr Lys
   1400 ccttcatacc aagatctgtt gagaactgga gacaccatca cacccagcaa cctggacacc    4465 aaggtccttt atcagacact gatggtgaca actcagcact gtgctgttac agacccaacc    4525 aggaaggttc cagaattccc tgtctatagc ctctcaatag ataacctg gtctgagctt     4585 gcatatgaat ctactttcag gtggaaatga ctctctcatt gcagaccagt tacaatgagg    4645 tacaagaatc acctggcccc ttcaggacca tgggccttgc tggcagatgg atcaaggatg    4705 ccaaacagtc caaacaatgc caaaggaaag gacctaagga cataccccca agccctacga    4765 gcagcattct gctggtagac tagggcggga gtcttgtcat gtaacctgca ggagatccta    4825 aatatagcct ctctctgggg gtgctagagt ggaccctgga attctaagca ctaataaccc    4885 tgaaatcaaa gaaactgccc gtttgatcca gcatgcccca cnccgcctcc ccaagcataa    4945 actgtgagat gttaaagggc attggaattt tttttttcac agtagtctgg aaaatactgg    5005 gttacactac agaaatccct gtataggctg aacacagccc cacactgact tattggcata    5065 attggaatga cagactggct agccagagag aatttactcc tctcccttgg aggagccagg    5125 gcagtccatc tttccagtgg tggaagagag gcatatctgc aaagctccca cttcaggagt    5185 gactatcacc tttttcttct atagtgtagg acatgaagga gaaatgtcac ccaaaggcct    5245
```

<210> SEQ ID NO 2
<211> LENGTH: 1403
<212> TYPE: PRT
<213> ORGANISM: Mus musculus

<400> SEQUENCE: 2

```
Met Arg Leu Gly Ala Ala Trp Ala Leu Leu Ala Ala Ala Leu Gly
  1               5                  10                  15

Leu Gly Thr Arg Gly Val Arg Ala Ala Val Ala Leu Ala Asp Phe Tyr
             20                  25                  30

Pro Phe Gly Thr Lys Arg Gly Asp Thr Val Thr Pro Lys Gln Asp Asp
         35                  40                  45

Gly Gly Ser Gly Leu Gln Pro Leu Ser Val Pro Phe Pro Phe Gly
     50                  55                  60
```

```
Ala Glu His Ser Gly Leu Tyr Val Asn Asn Asn Gly Ile Ile Ser Phe
 65                  70                  75                  80

Leu Lys Glu Val Ser Gln Phe Thr Pro Val Ala Phe Pro Ile Ala Lys
                 85                  90                  95

Asp Arg Cys Val Val Ala Ala Phe Trp Ala Asp Val Asp Asn Arg Arg
            100                 105                 110

Ala Gly Asp Val Tyr Tyr Arg Glu Ala Thr Asp Pro Ala Met Leu Asn
        115                 120                 125

Arg Ala Thr Glu Asp Ile Arg Arg Tyr Phe Pro Glu Leu Pro Asp Phe
    130                 135                 140

Ser Ala Thr Trp Val Phe Val Ala Thr Trp Tyr Arg Val Thr Phe Phe
145                 150                 155                 160

Gly Gly Ser Ser Ser Pro Val Asn Thr Phe Gln Thr Val Leu Ile
                165                 170                 175

Thr Asp Gly Arg Phe Ser Phe Thr Ile Phe Asn Tyr Glu Ser Ile Leu
            180                 185                 190

Trp Thr Thr Gly Thr His Ala Ser Ser Gly Gly Asp Thr Asp Gly Leu
            195                 200                 205

Gly Gly Ile Ala Ala Gln Ala Gly Phe Asn Ala Gly Asp Gly His Arg
        210                 215                 220

Tyr Phe Asn Ile Pro Gly Ser Arg Thr Ala Asp Met Ala Glu Val Glu
225                 230                 235                 240

Thr Thr Thr Asn Val Gly Val Pro Gly Arg Trp Ala Phe Arg Ile Asp
            245                 250                 255

Asp Ala Gln Val Arg Val Gly Gly Cys Gly His Thr Thr Ser Val Cys
            260                 265                 270

Leu Val Leu Arg Pro Cys Leu Asn Gly Gly Lys Cys Ile Asp Asp Cys
            275                 280                 285

Val Thr Gly Asn Pro Ser Tyr Thr Cys Ser Cys Leu Ala Gly Phe Thr
290                 295                 300

Gly Arg Arg Cys His Leu Asp Val Asn Glu Cys Ala Ser His Pro Cys
305                 310                 315                 320

Gln Asn Gly Gly Thr Cys Thr His Gly Val Asn Ser Phe Ser Cys Gln
                325                 330                 335

Cys Pro Ala Gly Phe Lys Gly Pro Thr Cys Glu Ser Ala Gln Ser Pro
            340                 345                 350

Cys Asp Asn Lys Val Cys Gln Asn Gly Gly Gln Cys Gln Ala Glu Ser
            355                 360                 365

Ser Ser Ala Val Cys Val Cys Gln Ala Gly Tyr Thr Gly Ala Thr Cys
        370                 375                 380

Glu Thr Asp Val Asp Glu Cys Ser Ser Asp Pro Cys Gln Asn Gly Gly
385                 390                 395                 400

Ser Cys Val Asp Leu Val Gly Asn Tyr Ser Cys Ile Cys Val Glu Pro
                405                 410                 415

Phe Glu Gly Pro Gln Cys Glu Thr Gly Ser Tyr Leu Val Pro Ser Pro
            420                 425                 430

Cys Leu Ser Asn Pro Cys Gln Asn Gly Gly Thr Cys Val Asp Ala Asp
            435                 440                 445

Glu Gly Tyr Val Cys Glu Cys Pro Glu Gly Phe Met Gly Leu Asp Cys
        450                 455                 460

Arg Glu Arg Ile Leu Asn Asp Cys Asp Cys Arg Asn Gly Gly Arg Cys
465                 470                 475                 480
```

```
Leu Gly Ala Asn Thr Thr Leu Cys Gln Cys Pro Gly Phe Phe Gly
            485                 490                 495

Leu Leu Cys Glu Phe Glu Val Thr Ala Thr Pro Cys Asn Met Asn Thr
        500                 505                 510

Gln Cys Pro Asp Gly Gly Tyr Cys Met Glu Tyr Gly Ser Tyr Leu
        515                 520                 525

Cys Val Cys His Thr Asp His Asn Ile Ser His Ser Leu Pro Ser Pro
    530                 535                 540

Cys Asp Ser Asp Pro Cys Phe Asn Gly Gly Ser Cys Asp Ala His Glu
545                 550                 555                 560

Asp Ser Tyr Thr Cys Glu Cys Pro Arg Gly Phe His Gly Arg His Cys
            565                 570                 575

Glu Lys Ala Arg Pro His Leu Cys Ser Ser Gly Pro Cys Arg Asn Gly
            580                 585                 590

Gly Thr Cys Lys Glu Met Gly Asp Glu Tyr Arg Cys Thr Cys Pro Tyr
            595                 600                 605

Arg Phe Thr Gly Arg His Cys Glu Ile Gly Lys Pro Asp Ser Cys Ala
        610                 615                 620

Ser Gly Pro Cys His Asn Gly Gly Thr Cys Phe His Tyr Ile Gly Lys
625                 630                 635                 640

Tyr Lys Cys Asp Cys Pro Pro Gly Phe Ser Gly Arg His Cys Glu Ile
            645                 650                 655

Ala Pro Ser Pro Cys Phe Arg Ser Pro Cys Met Asn Gly Gly Thr Cys
                660                 665                 670

Glu Asp Leu Gly Thr Asp Phe Ser Cys Tyr Cys Gln Pro Gly Tyr Thr
        675                 680                 685

Gly His Arg Cys Gln Ala Glu Val Asp Cys Gly His Pro Glu Glu Val
        690                 695                 700

Glu His Ala Thr Met Arg Phe Asn Gly Thr His Val Gly Ser Val Ala
705                 710                 715                 720

Leu Tyr Thr Cys Glu Pro Gly Phe Ser Leu Ser Ala Leu Ser His Ile
            725                 730                 735

Arg Val Cys Gln Pro Gln Gly Val Trp Ser Gln Pro Gln Cys Ile
        740                 745                 750

Glu Val Asp Glu Cys Arg Ser Gln Pro Cys Leu His Gly Gly Ser Cys
        755                 760                 765

Gln Asp Leu Ile Ala Asp Tyr Gln Cys Leu Cys Ser Pro Gly Tyr Glu
    770                 775                 780

Gly Val His Cys Glu Leu Glu Thr Asp Glu Cys Gln Ala Gln Pro Cys
785                 790                 795                 800

Arg Asn Gly Gly Ser Cys Arg Asp Leu Pro Arg Ala Phe Ile Cys Gln
            805                 810                 815

Cys Pro Glu Gly Phe Val Gly Ile His Cys Glu Thr Glu Val Asp Ala
        820                 825                 830

Cys Ala Ser Ser Pro Cys Gln His Gly Gly Arg Cys Glu Asp Gly Gly
        835                 840                 845

Gly Ala Tyr Leu Cys Val Cys Pro Glu Gly Phe Tyr Gly Asn Cys
        850                 855                 860

Glu Thr Val Ser Asp Pro Cys Phe Ser Pro Cys Gly Ser Arg Gly
865                 870                 875                 880

Tyr Cys Leu Ala Ser Asn Gly Ser His Ser Cys Thr Cys Lys Val Gly
                885                 890                 895

Tyr Thr Gly Lys Asp Cys Thr Lys Glu Leu Leu Pro Pro Thr Ala Leu
```

-continued

```
                900                 905                 910
Arg Val Glu Arg Val Glu Ser Gly Val Ser Ile Ser Trp Ser Pro
    915                 920                 925
Pro Glu Gly Thr Thr Ala Arg Gln Val Leu Asp Gly Tyr Ala Val Thr
    930                 935                 940
Tyr Ala Ser Ser Asp Gly Ser Ser Arg Arg Thr Asp Phe Val Asp Arg
945                 950                 955                 960
Ser Arg Ser Ser His Gln Leu Arg Ala Leu Ala Ala Gly Arg Ala Tyr
                965                 970                 975
Asn Ile Ser Val Phe Ser Val Lys Arg Asn Thr Asn Lys Asn Asp
            980                 985                 990
Ile Ser Arg Pro Ala Ala Leu Leu Thr Arg Thr Arg Pro Arg Pro Ile
        995                 1000                1005
Glu Asp Phe Glu Val Thr Asn Ile Ser Ala Asn Ala Ile Ser Val Gln
    1010                1015                1020
Trp Ala Leu His Arg Ile Gln His Ala Thr Val Ser Arg Val Arg Val
1025                1030                1035                1040
Ser Ile Leu Tyr Pro Glu Ala Ser Ala Val Gln Ser Thr Glu Val Asp
            1045                1050                1055
Arg Ser Val Asp Arg Leu Thr Phe Gly Asp Leu Leu Pro Gly Arg Arg
        1060                1065                1070
Tyr Thr Val Arg Leu Thr Thr Leu Ser Gly Pro Gly Gly Ala Glu Tyr
    1075                1080                1085
Pro Thr Glu Ser Leu Ala Ser Ala Pro Leu Asn Val Trp Thr Arg Pro
    1090                1095                1100
Leu Pro Pro Ala Asn Leu Thr Ala Ser Arg Val Thr Ala Thr Ser Ala
1105                1110                1115                1120
His Met Val Trp Asp Thr Pro Ala Pro Gly Ile Ser Leu Glu Ala Tyr
            1125                1130                1135
Val Ile Asn Val Thr Thr Ser Gln Ser Thr Lys Ser Arg Tyr Ile Pro
        1140                1145                1150
Asn Gly Lys Leu Val Ser Tyr Thr Val Arg Asp Leu Met Pro Gly Arg
    1155                1160                1165
Arg Tyr Gln Leu Ser Val Thr Ala Val Gln Ser Thr Glu Gln Gly Gln
    1170                1175                1180
Leu His Ser Glu Pro Ala His Leu Tyr Ile Ile Thr Ser Pro Arg Asp
1185                1190                1195                1200
Gly Thr Asp Arg Arg Trp His His Gly Gly His His Ser Arg Met Leu
            1205                1210                1215
Arg Asn Arg Pro Ala Pro Val Arg Leu Pro Glu Leu Arg Leu Leu Asn
        1220                1225                1230
Asp His Ser Ala Pro Glu Thr Pro Thr Gln Ser Ser Arg Phe Ser Glu
    1235                1240                1245
Leu Val Asp Gly Arg Gly Arg Val Ser Ala Arg Phe Gly Gly Leu Pro
    1250                1255                1260
Ser Arg Ala Val Thr Val Arg Ser Gln Pro Thr Thr Pro Val Pro Leu
1265                1270                1275                1280
Lys Asn Thr Glu Ala Pro Glu Gln Val His Leu Ala Leu Gln Leu Pro
            1285                1290                1295
Lys Asn Ser Ser Lys Asp Thr Glu Ser Thr Pro Gly Ser Cys Ser Glu
        1300                1305                1310
Asp Ala Cys Gln Asn Gly Gly Thr Cys Val Pro Gly Ala Asp Ala His
    1315                1320                1325
```

Ser Cys Asp Cys Arg Pro Gly Phe Lys Gly Arg His Cys Glu Leu Ala
    1330                1335                1340

Cys Glu Lys Val Pro Arg Pro Cys Thr Arg Leu Phe Ser Glu Thr Lys
1345                1350                1355                1360

Ser Phe Pro Val Trp Glu Gly Asp Ile Cys His His Val Tyr Lys Lys
                1365                1370                1375

Val Tyr Lys Val His Gln Asp Val Cys Phe Lys Glu Arg Cys Gln Ser
            1380                1385                1390

Thr Ser Leu Arg Lys Pro Lys Gln Glu Thr Lys
        1395                1400

<210> SEQ ID NO 3
<211> LENGTH: 1381
<212> TYPE: PRT
<213> ORGANISM: Mus musculus

<400> SEQUENCE: 3

Arg Ala Ala Val Ala Leu Ala Asp Phe Tyr Pro Phe Gly Thr Lys Arg
  1               5                  10                  15

Gly Asp Thr Val Thr Pro Lys Gln Asp Gly Gly Ser Gly Leu Gln
             20                  25                  30

Pro Leu Ser Val Pro Phe Pro Phe Gly Ala Glu His Ser Gly Leu
         35                  40                  45

Tyr Val Asn Asn Gly Ile Ile Ser Phe Leu Lys Glu Val Ser Gln
      50                  55                  60

Phe Thr Pro Val Ala Phe Pro Ile Ala Lys Asp Arg Cys Val Val Ala
 65                  70                  75                  80

Ala Phe Trp Ala Asp Val Asp Asn Arg Ala Gly Asp Val Tyr Tyr
                 85                  90                  95

Arg Glu Ala Thr Asp Pro Ala Met Leu Asn Arg Ala Thr Glu Asp Ile
                100                 105                 110

Arg Arg Tyr Phe Pro Glu Leu Pro Asp Phe Ser Ala Thr Trp Val Phe
            115                 120                 125

Val Ala Thr Trp Tyr Arg Val Thr Phe Phe Gly Gly Ser Ser Ser Ser
        130                 135                 140

Pro Val Asn Thr Phe Gln Thr Val Leu Ile Thr Asp Gly Arg Phe Ser
145                 150                 155                 160

Phe Thr Ile Phe Asn Tyr Glu Ser Ile Leu Trp Thr Thr Gly Thr His
                165                 170                 175

Ala Ser Ser Gly Gly Asp Thr Asp Gly Leu Gly Gly Ile Ala Ala Gln
            180                 185                 190

Ala Gly Phe Asn Ala Gly Asp Gly His Arg Tyr Phe Asn Ile Pro Gly
        195                 200                 205

Ser Arg Thr Ala Asp Met Ala Glu Val Glu Thr Thr Asn Val Gly
        210                 215                 220

Val Pro Gly Arg Trp Ala Phe Arg Ile Asp Asp Ala Gln Val Arg Val
225                 230                 235                 240

Gly Gly Cys Gly His Thr Thr Ser Val Cys Leu Val Leu Arg Pro Cys
                245                 250                 255

Leu Asn Gly Gly Lys Cys Ile Asp Asp Cys Val Thr Gly Asn Pro Ser
            260                 265                 270

Tyr Thr Cys Ser Cys Leu Ala Gly Phe Thr Gly Arg Arg Cys His Leu
        275                 280                 285

Asp Val Asn Glu Cys Ala Ser His Pro Cys Gln Asn Gly Gly Thr Cys

```
                290                 295                 300
Thr His Gly Val Asn Ser Phe Ser Cys Gln Cys Pro Ala Gly Phe Lys
305                 310                 315                 320

Gly Pro Thr Cys Glu Ser Ala Gln Ser Pro Cys Asp Asn Lys Val Cys
                325                 330                 335

Gln Asn Gly Gly Gln Cys Gln Ala Glu Ser Ser Ala Val Cys Val
            340                 345                 350

Cys Gln Ala Gly Tyr Thr Gly Ala Thr Cys Glu Thr Asp Val Asp Glu
            355                 360                 365

Cys Ser Ser Asp Pro Cys Gln Asn Gly Gly Ser Cys Val Asp Leu Val
370                 375                 380

Gly Asn Tyr Ser Cys Ile Cys Val Glu Pro Phe Glu Gly Pro Gln Cys
385                 390                 395                 400

Glu Thr Gly Ser Tyr Leu Val Pro Ser Pro Cys Leu Ser Asn Pro Cys
                405                 410                 415

Gln Asn Gly Gly Thr Cys Val Asp Ala Asp Glu Gly Tyr Val Cys Glu
            420                 425                 430

Cys Pro Glu Gly Phe Met Gly Leu Asp Cys Arg Glu Arg Ile Leu Asn
            435                 440                 445

Asp Cys Asp Cys Arg Asn Gly Gly Arg Cys Leu Gly Ala Asn Thr Thr
        450                 455                 460

Leu Cys Gln Cys Pro Pro Gly Phe Phe Gly Leu Leu Cys Glu Phe Glu
465                 470                 475                 480

Val Thr Ala Thr Pro Cys Asn Met Asn Thr Gln Cys Pro Asp Gly Gly
                485                 490                 495

Tyr Cys Met Glu Tyr Gly Gly Ser Tyr Leu Cys Val Cys His Thr Asp
            500                 505                 510

His Asn Ile Ser His Ser Leu Pro Ser Pro Cys Asp Ser Asp Pro Cys
        515                 520                 525

Phe Asn Gly Gly Ser Cys Asp Ala His Glu Asp Ser Tyr Thr Cys Glu
        530                 535                 540

Cys Pro Arg Gly Phe His Gly Arg His Cys Glu Lys Ala Arg Pro His
545                 550                 555                 560

Leu Cys Ser Ser Gly Pro Cys Arg Asn Gly Gly Thr Cys Lys Glu Met
                565                 570                 575

Gly Asp Glu Tyr Arg Cys Thr Cys Pro Tyr Arg Phe Thr Gly Arg His
            580                 585                 590

Cys Glu Ile Gly Lys Pro Asp Ser Cys Ala Ser Gly Pro Cys His Asn
            595                 600                 605

Gly Gly Thr Cys Phe His Tyr Ile Gly Lys Tyr Lys Cys Asp Cys Pro
        610                 615                 620

Pro Gly Phe Ser Gly Arg His Cys Glu Ile Ala Pro Ser Pro Cys Phe
625                 630                 635                 640

Arg Ser Pro Cys Met Asn Gly Gly Thr Cys Glu Asp Leu Gly Thr Asp
                645                 650                 655

Phe Ser Cys Tyr Cys Gln Pro Gly Tyr Thr Gly His Arg Cys Gln Ala
            660                 665                 670

Glu Val Asp Cys Gly His Pro Glu Glu Val Glu His Ala Thr Met Arg
            675                 680                 685

Phe Asn Gly Thr His Val Gly Ser Val Ala Leu Tyr Thr Cys Glu Pro
        690                 695                 700

Gly Phe Ser Leu Ser Ala Leu Ser His Ile Arg Val Cys Gln Pro Gln
705                 710                 715                 720
```

```
Gly Val Trp Ser Gln Pro Pro Gln Cys Ile Glu Val Asp Cys Arg
            725                 730                 735

Ser Gln Pro Cys Leu His Gly Gly Ser Cys Gln Asp Leu Ile Ala Asp
            740                 745                 750

Tyr Gln Cys Leu Cys Ser Pro Gly Tyr Glu Gly Val His Cys Glu Leu
            755                 760                 765

Glu Thr Asp Glu Cys Gln Ala Gln Pro Cys Arg Asn Gly Gly Ser Cys
    770                 775                 780

Arg Asp Leu Pro Arg Ala Phe Ile Cys Gln Cys Pro Glu Gly Phe Val
785                 790                 795                 800

Gly Ile His Cys Glu Thr Glu Val Asp Ala Cys Ala Ser Ser Pro Cys
                805                 810                 815

Gln His Gly Gly Arg Cys Glu Asp Gly Gly Ala Tyr Leu Cys Val
            820                 825                 830

Cys Pro Glu Gly Phe Phe Gly Tyr Asn Cys Glu Thr Val Ser Asp Pro
        835                 840                 845

Cys Phe Ser Ser Pro Cys Gly Ser Arg Gly Tyr Cys Leu Ala Ser Asn
    850                 855                 860

Gly Ser His Ser Cys Thr Cys Lys Val Gly Tyr Thr Gly Lys Asp Cys
865                 870                 875                 880

Thr Lys Glu Leu Leu Pro Pro Thr Ala Leu Arg Val Glu Arg Val Glu
                885                 890                 895

Glu Ser Gly Val Ser Ile Ser Trp Ser Pro Pro Glu Gly Thr Thr Ala
            900                 905                 910

Arg Gln Val Leu Asp Gly Tyr Ala Val Thr Tyr Ala Ser Ser Asp Gly
            915                 920                 925

Ser Ser Arg Arg Thr Asp Phe Val Asp Arg Ser Arg Ser Ser His Gln
        930                 935                 940

Leu Arg Ala Leu Ala Ala Gly Arg Ala Tyr Asn Ile Ser Val Phe Ser
945                 950                 955                 960

Val Lys Arg Asn Thr Asn Asn Lys Asn Asp Ile Ser Arg Pro Ala Ala
                965                 970                 975

Leu Leu Thr Arg Thr Arg Pro Arg Pro Ile Glu Asp Phe Glu Val Thr
            980                 985                 990

Asn Ile Ser Ala Asn Ala Ile Ser Val Gln Trp Ala Leu His Arg Ile
            995                 1000                1005

Gln His Ala Thr Val Ser Arg Val Arg Val Ser Ile Leu Tyr Pro Glu
    1010                1015                1020

Ala Ser Ala Val Gln Ser Thr Glu Val Asp Arg Ser Val Asp Arg Leu
1025                1030                1035                1040

Thr Phe Gly Asp Leu Leu Pro Gly Arg Arg Tyr Thr Val Arg Leu Thr
                1045                1050                1055

Thr Leu Ser Gly Pro Gly Gly Ala Glu Tyr Pro Thr Glu Ser Leu Ala
            1060                1065                1070

Ser Ala Pro Leu Asn Val Trp Thr Arg Pro Leu Pro Pro Ala Asn Leu
        1075                1080                1085

Thr Ala Ser Arg Val Thr Ala Thr Ser Ala His Met Val Trp Asp Thr
    1090                1095                1100

Pro Ala Pro Gly Ile Ser Leu Glu Ala Tyr Val Ile Asn Val Thr Thr
1105                1110                1115                1120

Ser Gln Ser Thr Lys Ser Arg Tyr Ile Pro Asn Gly Lys Leu Val Ser
                1125                1130                1135
```

Tyr Thr Val Arg Asp Leu Met Pro Gly Arg Arg Tyr Gln Leu Ser Val
        1140                1145                1150

Thr Ala Val Gln Ser Thr Glu Gln Gly Gln Leu His Ser Glu Pro Ala
        1155                1160                1165

His Leu Tyr Ile Ile Thr Ser Pro Arg Asp Gly Thr Asp Arg Arg Trp
    1170                1175                1180

His His Gly Gly His His Ser Arg Met Leu Arg Asn Arg Pro Ala Pro
1185                1190                1195                1200

Val Arg Leu Pro Glu Leu Arg Leu Leu Asn Asp His Ser Ala Pro Glu
                1205                1210                1215

Thr Pro Thr Gln Ser Ser Arg Phe Ser Glu Leu Val Asp Gly Arg Gly
        1220                1225                1230

Arg Val Ser Ala Arg Phe Gly Gly Leu Pro Ser Arg Ala Val Thr Val
        1235                1240                1245

Arg Ser Gln Pro Thr Thr Pro Val Pro Leu Lys Asn Thr Glu Ala Pro
    1250                1255                1260

Glu Gln Val His Leu Ala Leu Gln Leu Pro Lys Asn Ser Ser Lys Asp
1265                1270                1275                1280

Thr Glu Ser Thr Pro Gly Ser Cys Ser Glu Asp Ala Cys Gln Asn Gly
                1285                1290                1295

Gly Thr Cys Val Pro Gly Ala Asp Ala His Ser Cys Asp Cys Arg Pro
        1300                1305                1310

Gly Phe Lys Gly Arg His Cys Glu Leu Ala Cys Glu Lys Val Pro Arg
        1315                1320                1325

Pro Cys Thr Arg Leu Phe Ser Glu Thr Lys Ser Phe Pro Val Trp Glu
    1330                1335                1340

Gly Asp Ile Cys His His Val Tyr Lys Lys Val Tyr Lys Val His Gln
1345                1350                1355                1360

Asp Val Cys Phe Lys Glu Arg Cys Gln Ser Thr Ser Leu Arg Lys Pro
                1365                1370                1375

Lys Gln Glu Thr Lys
        1380

<210> SEQ ID NO 4
<211> LENGTH: 365
<212> TYPE: PRT
<213> ORGANISM: Mus musculus

<400> SEQUENCE: 4

Arg Ala Ala Val Ala Leu Ala Asp Phe Tyr Pro Phe Gly Thr Lys Arg
  1               5                  10                  15

Gly Asp Thr Val Thr Pro Lys Gln Asp Asp Gly Gly Ser Gly Leu Gln
             20                  25                  30

Pro Leu Ser Val Pro Phe Pro Phe Gly Ala Glu His Ser Gly Leu
         35                  40                  45

Tyr Val Asn Asn Asn Gly Ile Ile Ser Phe Leu Lys Glu Val Ser Gln
 50                  55                  60

Phe Thr Pro Val Ala Phe Pro Ile Ala Lys Asp Arg Cys Val Val Ala
 65                  70                  75                  80

Ala Phe Trp Ala Asp Val Asp Asn Arg Ala Gly Asp Val Tyr Tyr
                 85                  90                  95

Arg Glu Ala Thr Asp Pro Ala Met Leu Asn Arg Ala Thr Glu Asp Ile
            100                 105                 110

Arg Arg Tyr Phe Pro Glu Leu Pro Asp Phe Ser Ala Thr Trp Val Phe
         115                 120                 125

-continued

```
Val Ala Thr Trp Tyr Arg Val Thr Phe Phe Gly Gly Ser Ser Ser
    130                 135                 140

Pro Val Asn Thr Phe Gln Thr Val Leu Ile Thr Asp Gly Arg Phe Ser
145                 150                 155                 160

Phe Thr Ile Phe Asn Tyr Glu Ser Ile Leu Trp Thr Gly Thr His
                165                 170                 175

Ala Ser Ser Gly Gly Asp Thr Asp Gly Leu Gly Ile Ala Ala Gln
            180                 185                 190

Ala Gly Phe Asn Ala Gly Asp Gly His Arg Tyr Phe Asn Ile Pro Gly
                195                 200                 205

Ser Arg Thr Ala Asp Met Ala Glu Val Glu Thr Thr Asn Val Gly
    210                 215                 220

Val Pro Gly Arg Trp Ala Phe Arg Ile Asp Asp Ala Gln Val Arg Val
225                 230                 235                 240

Gly Gly Cys Gly His Thr Thr Ser Val Cys Leu Val Leu Arg Pro Cys
                245                 250                 255

Leu Asn Gly Gly Lys Cys Ile Asp Asp Cys Val Thr Gly Asn Pro Ser
            260                 265                 270

Tyr Thr Cys Ser Cys Leu Ala Gly Phe Thr Gly Arg Arg Cys His Leu
    275                 280                 285

Asp Val Asn Glu Cys Ala Ser His Pro Cys Gln Asn Gly Gly Thr Cys
    290                 295                 300

Thr His Gly Val Asn Ser Phe Ser Cys Gln Cys Pro Ala Gly Phe Lys
305                 310                 315                 320

Gly Pro Thr Cys Glu Ser Ala Gln Ser Pro Cys Asp Asn Lys Val Cys
                325                 330                 335

Gln Asn Gly Gly Gln Cys Gln Ala Glu Ser Ser Ser Ala Val Cys Val
            340                 345                 350

Cys Gln Ala Gly Tyr Thr Gly Ala Thr Cys Glu Thr Asp
    355                 360                 365

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:Synthetic
<220> FEATURE:
<221> NAME/KEY: misc feature
<222> LOCATION: (12)
<223> OTHER INFORMATION: n is A, C, G or T
<220> FEATURE:
<221> NAME/KEY: misc feature
<222> LOCATION: (15)
<223> OTHER INFORMATION: n is A, C, G or T
<220> FEATURE:
<221> NAME/KEY: misc feature
<222> LOCATION: (18)
<223> OTHER INFORMATION: n is A, C, G or T

<400> SEQUENCE: 5
gaattctgyc nccnggntt yt                                           22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Synthetic
<220> FEATURE:
<221> NAME/KEY: misc feature
```

```
<222> LOCATION: (10)
<223> OTHER INFORMATION: n is A, C, G or T
<220> FEATURE:
<221> NAME/KEY: misc_feature
<222> LOCATION: (13)
<223> OTHER INFORMATION: n is A, C, G or T
<220> FEATURE:
<221> NAME/KEY: misc_feature
<222> LOCATION: (16)
<223> OTHER INFORMATION: n is A, C, G or T

<400> SEQUENCE: 6
ggatccrcan gtnccnccrt t                                              21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 7
agtgccgtcc agagaatcct gg                                             22

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Synthetic

<400> SEQUENCE: 8
ggaggcacat gcaaggaaat gggcgacg                                       28

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence:Synthetic

<400> SEQUENCE: 9
gacatacttt gttgtcacac gaagattggc cgattcaca gg                        42

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 10
cacacgaaga ttggcccgat tcacagg                                        27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 11
gcacttgcca ccattgaggc atggacg                                        27

<210> SEQ ID NO 12
<211> LENGTH: 21
<212> TYPE: DNA
```

-continued

<213> ORGANISM: Artificial Sequence
<220> FEATURE:
<223> OTHER INFORMATION: Description of Artificial Sequence:Synthetic

<400> SEQUENCE: 12
cagatcccgg cgatgcgcct c                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 13
agggaattct ggaaccttcc t                                              21

<210> SEQ ID NO 14
<211> LENGTH: 82
<212> TYPE: DNA
<213> ORGANISM: Artificial Sequence
<220> FEATURE:
<223> OTHER INFORMATION: Description of Artificial Sequence:Synthetic

<400> SEQUENCE: 14
agcttccacc atgtctgcac ttctgatcct agctcttgtt ggagctgcag ttgctgacta    60
caaagacgat gacgacaagc ac                                             82

<210> SEQ ID NO 15
<211> LENGTH: 82
<212> TYPE: DNA
<213> ORGANISM: Artificial Sequence
<220> FEATURE:
<223> OTHER INFORMATION: Description of Artificial Sequence:Synthetic

<400> SEQUENCE: 15
tcgagtgctt gtcgtcatcg tctttgtagt cagcaactgc agctccaaca agagctagga    60
tcagaagtgc agacatggtg gt                                             82

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:Synthetic

<400> SEQUENCE: 16
ccgctcgaga gacatggctg aggtggagac c                                   31

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 17
ctgggatccg gtgaaggcac caggtag                                        27

<210> SEQ ID NO 18
<211> LENGTH: 5
<212> TYPE: PRT
<213> ORGANISM: Unknown Organism
<220> FEATURE:
<223> OTHER INFORMATION: Description of Unknown Organism:EGF like motif

```
<400> SEQUENCE: 18

Cys Pro Pro Gly Phe
 1               5

<210> SEQ ID NO 19
<211> LENGTH: 5
<212> TYPE: PRT
<213> ORGANISM: Unknown Organism
<220> FEATURE:
<223> OTHER INFORMATION: Description of Unknown Organism:EGF like motif

<400> SEQUENCE: 19

Asn Gly Gly Thr Cys
 1               5

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence:Synthetic

<400> SEQUENCE: 20

Cys Gln Ser Thr Ser Leu Arg Lys Pro Lys Gln Glu Thr Lys
 1               5                  10

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
gctgccagag cacaagcctc aggaaaccca acaggaaac aaagtcgata              50

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
gatctatcga ctttgtttcc tgtttgggtt tcctgaggct tgtgctctgg cagc        54

<210> SEQ ID NO 23
<211> LENGTH: 4242
<212> TYPE: DNA
<213> ORGANISM: Homo sapiens
<220> FEATURE:
<221> NAME/KEY: CDS
<222> LOCATION: (1)..(4242)

<400> SEQUENCE: 23 atg cgg cac ggc gtc gcc tgg gcg ctg ctg gtg gcc gcg gcc ctg ggg   48
Met Arg His Gly Val Ala Trp Ala Leu Leu Val Ala Ala Ala Leu Gly
 1               5                  10                  15 ctt ggg gcg cgc ggg gtg cgc ggc gcg gtg gcc ctt gcc gac ttc tac   96
Leu Gly Ala Arg Gly Val Arg Gly Ala Val Ala Leu Ala Asp Phe Tyr
             20                  25                  30 ccg ttc ggc gcc gag cgc ggc gac gcc gtc acc ccc aag cag gac gac  144
Pro Phe Gly Ala Glu Arg Gly Asp Ala Val Thr Pro Lys Gln Asp Asp
```

-continued

|  | 35 |  |  |  | 40 |  |  |  | 45 |  |  |  |  |  |
|---|---|---|---|---|---|---|---|---|---|---|---|---|---|---|
| ggc | ggc | tcg | ggg | ctg | cgg | ccg | ctc | tcg | gtg | ccc | ttc | ccg | ttc | ttc | ggt | 192 |
| Gly | Gly | Ser | Gly | Leu | Arg | Pro | Leu | Ser | Val | Pro | Phe | Pro | Phe | Phe | Gly |  |
|  | 50 |  |  |  | 55 |  |  |  |  | 60 |  |  |  |  |  |  |

```
ggc ggc tcg ggg ctg cgg ccg ctc tcg gtg ccc ttc ccg ttc ttc ggt     192
Gly Gly Ser Gly Leu Arg Pro Leu Ser Val Pro Phe Pro Phe Phe Gly
     50                  55                  60 gcc gag cac tcc gga ctc tac gtg aac aac aac ggg atc atc tcc ttc     240
Ala Glu His Ser Gly Leu Tyr Val Asn Asn Asn Gly Ile Ile Ser Phe
 65                  70                  75                  80 ctg aag gag gtt tct cag ttc acc cca gtg gcc ttc ccc att gcc aag     288
Leu Lys Glu Val Ser Gln Phe Thr Pro Val Ala Phe Pro Ile Ala Lys
                 85                  90                  95 gac cgc tgc gtg gtg gca gcc ttc tgg gca gat gtg gac aac cgg cgt     336
Asp Arg Cys Val Val Ala Ala Phe Trp Ala Asp Val Asp Asn Arg Arg
100                 105                 110 gca ggc gac gtg tac tac cgg gag gcc acc gac cca gcc atg ctg cgc     384
Ala Gly Asp Val Tyr Tyr Arg Glu Ala Thr Asp Pro Ala Met Leu Arg
            115                 120                 125 cga gcc acg gag gac gtc agg cac tac ttc ccc gag ctc ctg gac ttc     432
Arg Ala Thr Glu Asp Val Arg His Tyr Phe Pro Glu Leu Leu Asp Phe
        130                 135                 140 aat gcc acc tgg gtt ttt gtt gcc acc tgg tac cga gtg acc ttc ttt     480
Asn Ala Thr Trp Val Phe Val Ala Thr Trp Tyr Arg Val Thr Phe Phe
145                 150                 155                 160 gga ggc agt tcc tca tcc cct gtc aac aca ttc cag act gtg ctc atc     528
Gly Gly Ser Ser Ser Ser Pro Val Asn Thr Phe Gln Thr Val Leu Ile
                165                 170                 175 aca gac ggc aag ctc tcc ttc acc atc ttc aac tat gag tcc atc gtg     576
Thr Asp Gly Lys Leu Ser Phe Thr Ile Phe Asn Tyr Glu Ser Ile Val
            180                 185                 190 tgg acc aca ggc aca cac gcc agc agc ggg ggc aac gcc act ggc ctc     624
Trp Thr Thr Gly Thr His Ala Ser Ser Gly Gly Asn Ala Thr Gly Leu
        195                 200                 205 ggg ggc atc gca gcc cag gct ggc ttc aac gca ggc gat ggg cag cgt     672
Gly Gly Ile Ala Ala Gln Ala Gly Phe Asn Ala Gly Asp Gly Gln Arg
    210                 215                 220 tac ttc agt atc ccc ggc tcg cgc aca gca gac atg gcc gag gtg gag     720
Tyr Phe Ser Ile Pro Gly Ser Arg Thr Ala Asp Met Ala Glu Val Glu
225                 230                 235                 240 acc acc acc aac gtg ggt gtg ccc ggg cgc tgg gcg ttc aga atc gat     768
Thr Thr Thr Asn Val Gly Val Pro Gly Arg Trp Ala Phe Arg Ile Asp
                245                 250                 255 gat gcc cag gtg cgc gtg ggg ggc tgc ggc cat aca acg tcc gtg tgc     816
Asp Ala Gln Val Arg Val Gly Gly Cys Gly His Thr Thr Ser Val Cys
            260                 265                 270 ctg gcc ctg cgc ccc tgc ctc aac ggc ggc aag tgc atc gac gac tgc     864
Leu Ala Leu Arg Pro Cys Leu Asn Gly Gly Lys Cys Ile Asp Asp Cys
        275                 280                 285 gtc acg ggc aac ccc tcc tac acc tgc tcc tgc ctc tcg ggc ttc acg     912
Val Thr Gly Asn Pro Ser Tyr Thr Cys Ser Cys Leu Ser Gly Phe Thr
    290                 295                 300 ggg cgg agg tgc cac ctg gac gtg aac gaa tgt gcc tcc cag ccc tgt     960
Gly Arg Arg Cys His Leu Asp Val Asn Glu Cys Ala Ser Gln Pro Cys
305                 310                 315                 320 cag aat ggt ggg acc tgt act cac ggc atc aac agt ttc cgc tgc cag    1008
Gln Asn Gly Gly Thr Cys Thr His Gly Ile Asn Ser Phe Arg Cys Gln
                325                 330                 335 tgc ccg gct ggc ttt ggg gga ccc acc tgt gag aca gcc caa tcc ccc    1056
Cys Pro Ala Gly Phe Gly Gly Pro Thr Cys Glu Thr Ala Gln Ser Pro
            340                 345                 350 tgt gac acc aaa gag tgt caa cat ggt ggc cag tgc cag gtg gag aat    1104
```

```
Cys Asp Thr Lys Glu Cys Gln His Gly Gly Gln Cys Gln Val Glu Asn
        355                 360                 365 ggc tct gcg gtg tgt gtg tgc cag gcc gga tac acc gga gca gcc tgc      1152
Gly Ser Ala Val Cys Val Cys Gln Ala Gly Tyr Thr Gly Ala Ala Cys
    370                 375                 380 gag atg gat gtg gac gac tgc agc cct gac ccc tgc ctg aat gga ggc      1200
Glu Met Asp Val Asp Asp Cys Ser Pro Asp Pro Cys Leu Asn Gly Gly
385                 390                 395                 400 tct tgt gtt gac cta gtg ggg aat tac acc tgc ttg tgt gcc gag ccc      1248
Ser Cys Val Asp Leu Val Gly Asn Tyr Thr Cys Leu Cys Ala Glu Pro
                405                 410                 415 ttc aag gga ctt cgc tgt gag aca gga gac cat cca gtg cca gac gcc      1296
Phe Lys Gly Leu Arg Cys Glu Thr Gly Asp His Pro Val Pro Asp Ala
            420                 425                 430 tgc ctc tcg gcc cct tgc cac aat ggg ggc acc tgt gtg gat gcg gac      1344
Cys Leu Ser Ala Pro Cys His Asn Gly Gly Thr Cys Val Asp Ala Asp
        435                 440                 445 cag ggc tac gtg tgc gag tgc ccc gaa ggc ttc atg ggc ctg gac tgc      1392
Gln Gly Tyr Val Cys Glu Cys Pro Glu Gly Phe Met Gly Leu Asp Cys
    450                 455                 460 agg gag aga gtc ccc gat gac tgt gag tgc cgc aac gga ggc aga tgc      1440
Arg Glu Arg Val Pro Asp Asp Cys Glu Cys Arg Asn Gly Gly Arg Cys
465                 470                 475                 480 ctg ggc gcc aac acc acc ctc tgc cag tgc ccc ctg gga ttc ttt ggg      1488
Leu Gly Ala Asn Thr Thr Leu Cys Gln Cys Pro Leu Gly Phe Phe Gly
                485                 490                 495 ctt ctc tgt gaa ttt gaa atc aca gcc atg ccc tgc aac atg aac aca      1536
Leu Leu Cys Glu Phe Glu Ile Thr Ala Met Pro Cys Asn Met Asn Thr
            500                 505                 510 cag tgc cca gat ggg ggc tac tgc atg gag cac ggc ggg agc tac ctc      1584
Gln Cys Pro Asp Gly Gly Tyr Cys Met Glu His Gly Gly Ser Tyr Leu
        515                 520                 525 tgc gtc tgc cac acc gac cac aat gcc agc cac tcc ctg cca tca ccc      1632
Cys Val Cys His Thr Asp His Asn Ala Ser His Ser Leu Pro Ser Pro
    530                 535                 540 tgc gac tcg gac ccc tgc ttc aac gga ggc tcc tgc gat gcc cat gac      1680
Cys Asp Ser Asp Pro Cys Phe Asn Gly Gly Ser Cys Asp Ala His Asp
545                 550                 555                 560 gac tcc tac acc tgc gag tgc ccg cgc ggg ttc cac ggc aag cac tgc      1728
Asp Ser Tyr Thr Cys Glu Cys Pro Arg Gly Phe His Gly Lys His Cys
                565                 570                 575 gag aaa gcc cgg cca cac ctg tgc agc tca ggg ccc tgc cgg aac ggg      1776
Glu Lys Ala Arg Pro His Leu Cys Ser Ser Gly Pro Cys Arg Asn Gly
            580                 585                 590 ggc acg tgc aag gag gcg ggc ggc gag tac cac tgc agc tgc ccc tac      1824
Gly Thr Cys Lys Glu Ala Gly Gly Glu Tyr His Cys Ser Cys Pro Tyr
        595                 600                 605 cgc ttc act ggg agg cac tgt gag atc ggg aag cca gac tcg tgt gcc      1872
Arg Phe Thr Gly Arg His Cys Glu Ile Gly Lys Pro Asp Ser Cys Ala
    610                 615                 620 tct ggc ccc tgt cac aac ggc ggc acc tgc ttc cac tac att ggc aaa      1920
Ser Gly Pro Cys His Asn Gly Gly Thr Cys Phe His Tyr Ile Gly Lys
625                 630                 635                 640 tac aag tgt gac tgt ccc cca ggc ttc tcc ggg cgg cac tgc gag ata      1968
Tyr Lys Cys Asp Cys Pro Pro Gly Phe Ser Gly Arg His Cys Glu Ile
                645                 650                 655 gcc ccc tcc ccc tgc ttc cgg agc ccg tgt gtg aat ggg ggc acc tgc      2016
Ala Pro Ser Pro Cys Phe Arg Ser Pro Cys Val Asn Gly Gly Thr Cys
            660                 665                 670
```

```
gag gac cgg gac acg gat ttc ttc tgc cac tgc caa gca ggg tac atg    2064
Glu Asp Arg Asp Thr Asp Phe Phe Cys His Cys Gln Ala Gly Tyr Met
            675                 680                 685 gga cgc cgg tgc cag gca gag gtg gac tgc ggc ccc ccg gag gag gtg    2112
Gly Arg Arg Cys Gln Ala Glu Val Asp Cys Gly Pro Pro Glu Glu Val
690                 695                 700 aag cac gcc aca ctg cgc ttc aac ggc acg cgg ctg gcg gtg gcc        2160
Lys His Ala Thr Leu Arg Phe Asn Gly Thr Arg Leu Ala Val Ala
705                 710                 715                 720 ctg tat gca tgt gac cgt ggc tac agc ctg agc gcc ccc agc cgc atc    2208
Leu Tyr Ala Cys Asp Arg Gly Tyr Ser Leu Ser Ala Pro Ser Arg Ile
                725                 730                 735 cgg gtc tgc cag cca cac ggt gtc tgg agt gag cct ccc cag tgc ctt    2256
Arg Val Cys Gln Pro His Gly Val Trp Ser Glu Pro Pro Gln Cys Leu
            740                 745                 750 gaa atc gat gag tgc cgg tct cag ccg tgc ctg cat ggg ggc tct tgt    2304
Glu Ile Asp Glu Cys Arg Ser Gln Pro Cys Leu His Gly Gly Ser Cys
            755                 760                 765 cag gac cgc gtt gct ggg tac ctg tgc ctc tgc agc aca ggc tat gag    2352
Gln Asp Arg Val Ala Gly Tyr Leu Cys Leu Cys Ser Thr Gly Tyr Glu
770                 775                 780 ggc gcc cac tgt gag ctg gag agg gat gag tgc cga gct cac ccg tgc    2400
Gly Ala His Cys Glu Leu Glu Arg Asp Glu Cys Arg Ala His Pro Cys
785                 790                 795                 800 aga aat gga ggg tcc tgc agg aac ctc cca ggg gcc tat gtc tgc cgg    2448
Arg Asn Gly Gly Ser Cys Arg Asn Leu Pro Gly Ala Tyr Val Cys Arg
                805                 810                 815 tgc cct gca ggc ttc gtt gga gtc cac tgt gag aca gag gtg gac gcc    2496
Cys Pro Ala Gly Phe Val Gly Val His Cys Glu Thr Glu Val Asp Ala
            820                 825                 830 tgc gac tcc agc ccc tgc cag cat gga ggc cgg tgt gag agc ggc ggc    2544
Cys Asp Ser Ser Pro Cys Gln His Gly Gly Arg Cys Glu Ser Gly Gly
            835                 840                 845 ggg gcc tac ctg tgc gtc tgc cca gag agc ttc ttc ggc tac cac tgc    2592
Gly Ala Tyr Leu Cys Val Cys Pro Glu Ser Phe Phe Gly Tyr His Cys
850                 855                 860 gag aca gtg agt gac ccc tgc ttc tcc agc ccc tgt ggg ggc cgt ggc    2640
Glu Thr Val Ser Asp Pro Cys Phe Ser Ser Pro Cys Gly Gly Arg Gly
865                 870                 875                 880 tat tgc ctg gcc agc aac ggc tcc cac agc tgc acc tgc aaa gtg ggc    2688
Tyr Cys Leu Ala Ser Asn Gly Ser His Ser Cys Thr Cys Lys Val Gly
                885                 890                 895 tac acg ggc gag gac tgc gcc aaa gag ctc ttc cca ccg acg gcc ctc    2736
Tyr Thr Gly Glu Asp Cys Ala Lys Glu Leu Phe Pro Pro Thr Ala Leu
            900                 905                 910 aag atg gag aga gtg gag gag agt ggg gtc tct atc tcc tgg aac ccg    2784
Lys Met Glu Arg Val Glu Glu Ser Gly Val Ser Ile Ser Trp Asn Pro
            915                 920                 925 ccc aat ggt cca gcc gcc agg cag atg ctt gat ggc tac gcg tcc acc    2832
Pro Asn Gly Pro Ala Ala Arg Gln Met Leu Asp Gly Tyr Ala Val Thr
930                 935                 940 tac gtc tcc tcc gac ggc tcc tac cgc cgc aca gac ttt gtg gac agg    2880
Tyr Val Ser Ser Asp Gly Ser Tyr Arg Arg Thr Asp Phe Val Asp Arg
945                 950                 955                 960 acc cgc tcc tcg cac cag ctc cag gcc ctg gcg gcc ggc agg gcc tac    2928
Thr Arg Ser Ser His Gln Leu Gln Ala Leu Ala Ala Gly Arg Ala Tyr
                965                 970                 975 aac atc tcc gtc ttc tca gtg aag cga aac agt aac aac aag aat gac    2976
Asn Ile Ser Val Phe Ser Val Lys Arg Asn Ser Asn Asn Lys Asn Asp
            980                 985                 990
```

| | |
|---|---|
| atc agc agg cct gcc gtg ctg ctg gcc cgc acg cga ccc cgc cct gtg<br>Ile Ser Arg Pro Ala Val Leu Leu Ala Arg Thr Arg Pro Arg Pro Val<br>    995                    1000                  1005 | 3024 |
| gaa ggc ttc gag gtc acc aat gtg acg gct agc acc atc tca gtg cag<br>Glu Gly Phe Glu Val Thr Asn Val Thr Ala Ser Thr Ile Ser Val Gln<br>   1010                 1015                 1020 | 3072 |
| tgg gcc ctg cac agg atc cgc cat gcc acc gtc agt ggg gtc cgt gtg<br>Trp Ala Leu His Arg Ile Arg His Ala Thr Val Ser Gly Val Arg Val<br>1025                 1030                 1035                 1040 | 3120 |
| tcc atc cgc cac cct gag gcc ctc agg gac cag gcc acc gat gtg gac<br>Ser Ile Arg His Pro Glu Ala Leu Arg Asp Gln Ala Thr Asp Val Asp<br>               1045                 1050                 1055 | 3168 |
| agg agt gtg gac agg ttc acc ttt agg gcc ctg ctg cct ggg aag agg<br>Arg Ser Val Asp Arg Phe Thr Phe Arg Ala Leu Leu Pro Gly Lys Arg<br>   1060                 1065                 1070 | 3216 |
| tac acc atc cag ctg acc acc ctc agt ggg ctc agg gga gag gag cac<br>Tyr Thr Ile Gln Leu Thr Thr Leu Ser Gly Leu Arg Gly Glu Glu His<br>      1075                1080                 1085 | 3264 |
| ccc aca gag agc ctg gcc acc gcg ccg acg cac gtg tgg acc cgg ccc<br>Pro Thr Glu Ser Leu Ala Thr Ala Pro Thr His Val Trp Thr Arg Pro<br>  1090                 1095                 1100 | 3312 |
| ctg cct cca gca aac ctg acc gcc gcc cga gtc act gcc acc tct gcc<br>Leu Pro Pro Ala Asn Leu Thr Ala Ala Arg Val Thr Ala Thr Ser Ala<br>1105                 1110                 1115                 1120 | 3360 |
| cac gtg gtc tgg gat gcc ccg act cca ggc agc ttg ctg gag gct tat<br>His Val Val Trp Asp Ala Pro Thr Pro Gly Ser Leu Leu Glu Ala Tyr<br>               1125                 1130                 1135 | 3408 |
| gtc atc aat gtg acc acc agc cag agc acc aag agc cgc tat gtc ccc<br>Val Ile Asn Val Thr Thr Ser Gln Ser Thr Lys Ser Arg Tyr Val Pro<br>   1140                 1145                 1150 | 3456 |
| aac ggg aag ctg gcg tcc tac acg gtg cgc gac ctg ctg ccg gga cgg<br>Asn Gly Lys Leu Ala Ser Tyr Thr Val Arg Asp Leu Leu Pro Gly Arg<br>      1155                1160                 1165 | 3504 |
| cgg tac cag ctc tct gtg ata gca gtg cag agc acg gag ctc ggg ccg<br>Arg Tyr Gln Leu Ser Val Ile Ala Val Gln Ser Thr Glu Leu Gly Pro<br>  1170                 1175                 1180 | 3552 |
| cag cac agc gag ccc gcc cac ctc tac atc atc acc tcc ccc agg gat<br>Gln His Ser Glu Pro Ala His Leu Tyr Ile Ile Thr Ser Pro Arg Asp<br>1185                 1190                 1195                 1200 | 3600 |
| ggc gct gac aga cgc tgg cac cag gga gga cac cac cct cgg gtg ctc<br>Gly Ala Asp Arg Arg Trp His Gln Gly Gly His His Pro Arg Val Leu<br>               1205                 1210                 1215 | 3648 |
| aag aac aga ccg ccc ccg gcg cgc ctg ccg gag ctg cgc ctg ctc aat<br>Lys Asn Arg Pro Pro Pro Ala Arg Leu Pro Glu Leu Arg Leu Leu Asn<br>   1220                 1225                 1230 | 3696 |
| gac cac agc gcc ccc gag acc ccc acc cag ccc ccc agg ttc tcg gag<br>Asp His Ser Ala Pro Glu Thr Pro Thr Gln Pro Pro Arg Phe Ser Glu<br>      1235              1240                 1245 | 3744 |
| ctt gtg gac ggc aga gga aga gtg agc gcc agg ttc ggt ggc tca ccc<br>Leu Val Asp Gly Arg Gly Arg Val Ser Ala Arg Phe Gly Gly Ser Pro<br>  1250                 1255                 1260 | 3792 |
| agc aaa gca gcc acc gtg aga tca caa ccc aca gcc tcg gcg cag ctc<br>Ser Lys Ala Ala Thr Val Arg Ser Gln Pro Thr Ala Ser Ala Gln Leu<br>1265                 1270                 1275                 1280 | 3840 |
| gag aac atg gag gaa gcc ccc aag cgg gtc agc ctg gcc ctc cag ctc<br>Glu Asn Met Glu Glu Ala Pro Lys Arg Val Ser Leu Ala Leu Gln Leu<br>               1285                 1290                 1295 | 3888 |
| cct gaa cac ggc agc aag gac atc gga aac gtc cct ggc aac tgt tca<br>Pro Glu His Gly Ser Lys Asp Ile Gly Asn Val Pro Gly Asn Cys Ser | 3936 |

-continued

```
                1300                1305                1310
gaa aac ccc tgt cag aac gga ggc act tgt gtg ccg ggc gca gac gcc      3984
Glu Asn Pro Cys Gln Asn Gly Gly Thr Cys Val Pro Gly Ala Asp Ala
        1315                1320                1325 cac agc tgt gac tgc ggg cca ggg ttc aaa ggc aga cgc tgc gag ctc      4032
His Ser Cys Asp Cys Gly Pro Gly Phe Lys Gly Arg Arg Cys Glu Leu
    1330                1335                1340 gcc tgt ata aag gtg tcc cgc ccc tgc aca agg ctg ttc tcc gag aca      4080
Ala Cys Ile Lys Val Ser Arg Pro Cys Thr Arg Leu Phe Ser Glu Thr
1345                1350                1355                1360 aag gcc ttt cca gtc tgg gag gga ggc gtc tgt cac cac gtg tat aaa      4128
Lys Ala Phe Pro Val Trp Glu Gly Gly Val Cys His His Val Tyr Lys
            1365                1370                1375 aga gtc tac cga gtt cac caa gac atc tgc ttc aaa gag agc tgt gaa      4176
Arg Val Tyr Arg Val His Gln Asp Ile Cys Phe Lys Glu Ser Cys Glu
        1380                1385                1390 agc aca agc ctc aag aag acc cca aac agg aaa caa agt aag agt cag      4224
Ser Thr Ser Leu Lys Lys Thr Pro Asn Arg Lys Gln Ser Lys Ser Gln
    1395                1400                1405 aca ctg gag aaa tct taa                                              4242
Thr Leu Glu Lys Ser
    1410
```

<210> SEQ ID NO 24
<211> LENGTH: 1413
<212> TYPE: PRT
<213> ORGANISM: Homo sapiens

<400> SEQUENCE: 24

```
Met Arg His Gly Val Ala Trp Ala Leu Leu Val Ala Ala Ala Leu Gly
1               5                  10                  15

Leu Gly Ala Arg Gly Val Arg Gly Ala Val Ala Leu Ala Asp Phe Tyr
            20                  25                  30

Pro Phe Gly Ala Glu Arg Gly Asp Ala Val Thr Pro Lys Gln Asp Asp
        35                  40                  45

Gly Gly Ser Gly Leu Arg Pro Leu Ser Val Pro Phe Pro Phe Phe Gly
    50                  55                  60

Ala Glu His Ser Gly Leu Tyr Val Asn Asn Asn Gly Ile Ile Ser Phe
65                  70                  75                  80

Leu Lys Glu Val Ser Gln Phe Thr Pro Val Ala Phe Pro Ile Ala Lys
                85                  90                  95

Asp Arg Cys Val Val Ala Ala Phe Trp Ala Asp Val Asp Asn Arg Arg
            100                 105                 110

Ala Gly Asp Val Tyr Tyr Arg Glu Ala Thr Asp Pro Ala Met Leu Arg
        115                 120                 125

Arg Ala Thr Glu Asp Val Arg His Tyr Phe Pro Glu Leu Leu Asp Phe
    130                 135                 140

Asn Ala Thr Trp Val Phe Val Ala Thr Trp Tyr Arg Val Thr Phe Phe
145                 150                 155                 160

Gly Gly Ser Ser Ser Pro Val Asn Thr Phe Gln Thr Val Leu Ile
                165                 170                 175

Thr Asp Gly Lys Leu Ser Phe Thr Ile Phe Asn Tyr Glu Ser Ile Val
            180                 185                 190

Trp Thr Thr Gly Thr His Ala Ser Ser Gly Gly Asn Ala Thr Gly Leu
        195                 200                 205

Gly Gly Ile Ala Ala Gln Ala Gly Phe Asn Ala Gly Asp Gly Gln Arg
    210                 215                 220
```

```
Tyr Phe Ser Ile Pro Gly Ser Arg Thr Ala Asp Met Ala Glu Val Glu
225                 230                 235                 240

Thr Thr Thr Asn Val Gly Val Pro Gly Arg Trp Ala Phe Arg Ile Asp
            245                 250                 255

Asp Ala Gln Val Arg Val Gly Gly Cys Gly His Thr Thr Ser Val Cys
        260                 265                 270

Leu Ala Leu Arg Pro Cys Leu Asn Gly Gly Lys Cys Ile Asp Asp Cys
        275                 280                 285

Val Thr Gly Asn Pro Ser Tyr Thr Cys Ser Cys Leu Ser Gly Phe Thr
    290                 295                 300

Gly Arg Arg Cys His Leu Asp Val Asn Glu Cys Ala Ser Gln Pro Cys
305                 310                 315                 320

Gln Asn Gly Gly Thr Cys Thr His Gly Ile Asn Ser Phe Arg Cys Gln
                325                 330                 335

Cys Pro Ala Gly Phe Gly Gly Pro Thr Cys Glu Thr Ala Gln Ser Pro
            340                 345                 350

Cys Asp Thr Lys Glu Cys Gln His Gly Gly Gln Cys Gln Val Glu Asn
        355                 360                 365

Gly Ser Ala Val Cys Val Cys Gln Ala Gly Tyr Thr Gly Ala Ala Cys
    370                 375                 380

Glu Met Asp Val Asp Cys Ser Pro Asp Pro Cys Leu Asn Gly Gly
385                 390                 395                 400

Ser Cys Val Asp Leu Val Gly Asn Tyr Thr Cys Leu Cys Ala Glu Pro
            405                 410                 415

Phe Lys Gly Leu Arg Cys Glu Thr Gly Asp His Pro Val Pro Asp Ala
        420                 425                 430

Cys Leu Ser Ala Pro Cys His Asn Gly Gly Thr Cys Val Asp Ala Asp
        435                 440                 445

Gln Gly Tyr Val Cys Glu Cys Pro Glu Gly Phe Met Gly Leu Asp Cys
    450                 455                 460

Arg Glu Arg Val Pro Asp Asp Cys Glu Cys Arg Asn Gly Gly Arg Cys
465                 470                 475                 480

Leu Gly Ala Asn Thr Thr Leu Cys Gln Cys Pro Leu Gly Phe Phe Gly
                485                 490                 495

Leu Leu Cys Glu Phe Glu Ile Thr Ala Met Pro Cys Asn Met Asn Thr
            500                 505                 510

Gln Cys Pro Asp Gly Gly Tyr Cys Met Glu His Gly Gly Ser Tyr Leu
        515                 520                 525

Cys Val Cys His Thr Asp His Asn Ala Ser His Ser Leu Pro Ser Pro
    530                 535                 540

Cys Asp Ser Asp Pro Cys Phe Asn Gly Gly Ser Cys Asp Ala His Asp
545                 550                 555                 560

Asp Ser Tyr Thr Cys Glu Cys Pro Arg Gly Phe His Gly Lys His Cys
                565                 570                 575

Glu Lys Ala Arg Pro His Leu Cys Ser Ser Gly Pro Cys Arg Asn Gly
            580                 585                 590

Gly Thr Cys Lys Glu Ala Gly Gly Glu Tyr His Cys Ser Cys Pro Tyr
        595                 600                 605

Arg Phe Thr Gly Arg His Cys Glu Ile Gly Lys Pro Asp Ser Cys Ala
    610                 615                 620

Ser Gly Pro Cys His Asn Gly Gly Thr Cys Phe His Tyr Ile Gly Lys
625                 630                 635                 640
```

-continued

Tyr Lys Cys Asp Cys Pro Gly Phe Ser Gly Arg His Cys Glu Ile
            645                 650                 655

Ala Pro Ser Pro Cys Phe Arg Ser Pro Cys Val Asn Gly Gly Thr Cys
            660                 665                 670

Glu Asp Arg Asp Thr Asp Phe Phe Cys His Cys Gln Ala Gly Tyr Met
            675                 680                 685

Gly Arg Arg Cys Gln Ala Glu Val Asp Cys Gly Pro Pro Glu Glu Val
690                 695                 700

Lys His Ala Thr Leu Arg Phe Asn Gly Thr Arg Leu Gly Ala Val Ala
705                 710                 715                 720

Leu Tyr Ala Cys Asp Arg Gly Tyr Ser Leu Ser Ala Pro Ser Arg Ile
                725                 730                 735

Arg Val Cys Gln Pro His Gly Val Trp Ser Glu Pro Pro Gln Cys Leu
            740                 745                 750

Glu Ile Asp Glu Cys Arg Ser Gln Pro Cys Leu His Gly Gly Ser Cys
            755                 760                 765

Gln Asp Arg Val Ala Gly Tyr Leu Cys Leu Cys Ser Thr Gly Tyr Glu
770                 775                 780

Gly Ala His Cys Glu Leu Glu Arg Asp Glu Cys Arg Ala His Pro Cys
785                 790                 795                 800

Arg Asn Gly Gly Ser Cys Arg Asn Leu Pro Gly Ala Tyr Val Cys Arg
                805                 810                 815

Cys Pro Ala Gly Phe Val Gly Val His Cys Glu Thr Glu Val Asp Ala
            820                 825                 830

Cys Asp Ser Ser Pro Cys Gln His Gly Gly Arg Cys Glu Ser Gly Gly
            835                 840                 845

Gly Ala Tyr Leu Cys Val Cys Pro Glu Ser Phe Phe Gly Tyr His Cys
850                 855                 860

Glu Thr Val Ser Asp Pro Cys Phe Ser Ser Pro Cys Gly Gly Arg Gly
865                 870                 875                 880

Tyr Cys Leu Ala Ser Asn Gly Ser His Ser Cys Thr Cys Lys Val Gly
                885                 890                 895

Tyr Thr Gly Glu Asp Cys Ala Lys Glu Leu Phe Pro Pro Thr Ala Leu
            900                 905                 910

Lys Met Glu Arg Val Glu Glu Ser Gly Val Ser Ile Ser Trp Asn Pro
915                 920                 925

Pro Asn Gly Pro Ala Ala Arg Gln Met Leu Asp Gly Tyr Ala Val Thr
930                 935                 940

Tyr Val Ser Ser Asp Gly Ser Tyr Arg Arg Thr Asp Phe Val Asp Arg
945                 950                 955                 960

Thr Arg Ser Ser His Gln Leu Gln Ala Leu Ala Ala Gly Arg Ala Tyr
                965                 970                 975

Asn Ile Ser Val Phe Ser Val Lys Arg Asn Ser Asn Asn Lys Asn Asp
            980                 985                 990

Ile Ser Arg Pro Ala Val Leu Leu Ala Arg Thr Arg Pro Arg Pro Val
            995                 1000                1005

Glu Gly Phe Glu Val Thr Asn Val Thr Ala Ser Thr Ile Ser Val Gln
    1010                1015                1020

Trp Ala Leu His Arg Ile Arg His Ala Thr Val Ser Gly Val Arg Val
1025                1030                1035                1040

Ser Ile Arg His Pro Glu Ala Leu Arg Asp Gln Ala Thr Asp Val Asp
                1045                1050                1055

Arg Ser Val Asp Arg Phe Thr Phe Arg Ala Leu Leu Pro Gly Lys Arg

```
                    1060                1065                1070
Tyr Thr Ile Gln Leu Thr Thr Leu Ser Gly Leu Arg Gly Glu Glu His
           1075                1080                1085

Pro Thr Glu Ser Leu Ala Thr Ala Pro Thr His Val Trp Thr Arg Pro
    1090                1095                1100

Leu Pro Pro Ala Asn Leu Thr Ala Ala Arg Val Thr Ala Thr Ser Ala
1105                1110                1115                1120

His Val Val Trp Asp Ala Pro Thr Pro Gly Ser Leu Glu Ala Tyr
               1125                1130                1135

Val Ile Asn Val Thr Thr Ser Gln Ser Thr Lys Ser Arg Tyr Val Pro
           1140                1145                1150

Asn Gly Lys Leu Ala Ser Tyr Thr Val Arg Asp Leu Leu Pro Gly Arg
       1155                1160                1165

Arg Tyr Gln Leu Ser Val Ile Ala Val Gln Ser Thr Glu Leu Gly Pro
    1170                1175                1180

Gln His Ser Glu Pro Ala His Leu Tyr Ile Ile Thr Ser Pro Arg Asp
1185                1190                1195                1200

Gly Ala Asp Arg Arg Trp His Gln Gly Gly His His Pro Arg Val Leu
               1205                1210                1215

Lys Asn Arg Pro Pro Pro Ala Arg Leu Pro Glu Leu Arg Leu Leu Asn
           1220                1225                1230

Asp His Ser Ala Pro Glu Thr Pro Thr Gln Pro Pro Arg Phe Ser Glu
       1235                1240                1245

Leu Val Asp Gly Arg Gly Arg Val Ser Ala Arg Phe Gly Gly Ser Pro
    1250                1255                1260

Ser Lys Ala Ala Thr Val Arg Ser Gln Pro Thr Ala Ser Ala Gln Leu
1265                1270                1275                1280

Glu Asn Met Glu Glu Ala Pro Lys Arg Val Ser Leu Ala Leu Gln Leu
               1285                1290                1295

Pro Glu His Gly Ser Lys Asp Ile Gly Asn Val Pro Gly Asn Cys Ser
           1300                1305                1310

Glu Asn Pro Cys Gln Asn Gly Gly Thr Cys Val Pro Gly Ala Asp Ala
       1315                1320                1325

His Ser Cys Asp Cys Gly Pro Gly Phe Lys Gly Arg Arg Cys Glu Leu
    1330                1335                1340

Ala Cys Ile Lys Val Ser Arg Pro Cys Thr Arg Leu Phe Ser Glu Thr
1345                1350                1355                1360

Lys Ala Phe Pro Val Trp Glu Gly Gly Val Cys His His Val Tyr Lys
               1365                1370                1375

Arg Val Tyr Arg Val His Gln Asp Ile Cys Phe Lys Glu Ser Cys Glu
           1380                1385                1390

Ser Thr Ser Leu Lys Lys Thr Pro Asn Arg Lys Gln Ser Lys Ser Gln
       1395                1400                1405

Thr Leu Glu Lys Ser
    1410

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
```

```
ccaaggaccg ctgcgtggtg                                              20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
ttaagatttc accagtgtca gactc                                        25

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
acactctttg gtgtcacagg gggattgggc tgtctcacag g                      41

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
atgcggcacg gcgtcgcctg                                              20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 29
aaggtcactc ggtaccaggt gg                                           22

<210> SEQ ID NO 30
<211> LENGTH: 192
<212> TYPE: DNA
<213> ORGANISM: Artificial Sequence
<220> FEATURE:
<223> OTHER INFORMATION: Description of Artificial Sequence: predicted
      sequence

<400> SEQUENCE: 30
tctgggggct ggccgctcag gctcagactc tccaaacagg actcccagtg ggactcctgg   60
ggccagggac tcatgacagc aggctcagct cagctgaagg aacaggcccg agtgccggtt  120
ctgtctccat ggctcccaga gtgtgacccc aggccaagcc cttatggcag cccagggaat  180
gaaatgcacc tg                                                     192

<210> SEQ ID NO 31
<211> LENGTH: 4084
<212> TYPE: DNA
<213> ORGANISM: Mus musculus
<220> FEATURE:
```

<221> NAME/KEY: promoter
<222> LOCATION: (1)..(3487)
<223> OTHER INFORMATION: SELF gene promoter region including
      transcription factor binding site

<400> SEQUENCE: 31

```
gatatcaggg tattcccaat gccttaaaaa aaaaatccta gcagcatgac tttatctgtt      60
gtggtttctc aagtctacat gcccaaccta tgtcagctgc ctcagtgttc aagaaacagg     120
gaatagagtg ctccctgcag gagatggccc ccaagataca tggtggagcc caagtccaca     180
tatgcatgtg ttcctagcca ccatgaacct caagtagact cagagatttc catagaccaa     240
ctcctgcatc actacccact cgagtgggtg ggaaagttct gcctgagccc cacctgcatt     300
cagttcctgt ttgttggagg caaaacaagt gatagccatt ttgagagcat ttgctgagct     360
ccagctaact atcacccgaa gattaatagc aatggtcaca tcctgggtgc tgaggttggc     420
aggtctcctg tgcatatgcg gtgtgcaggt atgacacccc tcccctcttg gtcaaggtga     480
actgtccagt ctcacatatg ggtgggccat gtaattctcc tcaggagttg ggacctactt     540
ttcccaggac cctgaggcct ctcccaaccc atcctggaag agtagatggt cactggaggg     600
agggaagggc ttgtttatgc tttgtgaaga aaagaattgt tgtagggagc atatgttact     660
ccagctacct ccaaagagaa gcagcaaaag gtagggtagg ctgcagcctc aggcctgctg     720
tgtgggacca gctgactagc ctggttcccc taccaggcgg aacaaggata gtgttcccca     780
tcttgacctt catggactcc taaggcctga acatctggtg ggtggctctg gggctccccc     840
atgtaaacag gcacacacag tcaggcccta aattaaagtg tcacaggcct cttgagaagc     900
tcaggtttcc tgctgcagaa catgagcctg cttgataaaa cgatttgggt tgtgataaat     960
gtggattttc tgtggtagac aaaggcgccc ttgagtccag aggggaacct aaaacagctt    1020
gttgctgaaa agtatttcct gatcatattt ttagcacctg aaaaaagatt ctttttactct   1080
ctctctcttt ttgcctgtgg gtctcgtgtg tgtgtgtgtg tgtgtgtgtg tgtgtgtgtg    1140
tgtgtaatgt gatacccagc aacaacagtg agatctgtta gcctccccac ctcaccccca    1200
accctgtctc ccaggccttg ttgaaaacct acacagggca tccagttggg gatggccgta    1260
agcaccacac cactaccctt gatggagatc agaggatcca gcctgcagct ggacctgtgc    1320
acaagcccag ctctgagatg ggcctctgtc ctggtatccc acagctggtc aggagattct    1380
agtggaaagc agtcaggacc ccatgtctca ccacacctgg agggatactc aacgacgcta    1440
ttgagcactg ctgtgtactt gatagtgtgc tgagtgctgt gccaacccag aaatccctga    1500
gcagacccaa acccttgact aggaccctct gaggcatgtg ctcccggaga aggttggcag    1560
cgttgagatg ggaacagtgg cctggcaata ggtagagcaa ggttgtgtgg ttggagagag    1620
caaggatcgg tagttatggg ctcttctcag tgccccatgg gcagaaaggc aaatccgagt    1680
tctccctagg cttggtgctg cctgctacac ttctgtatga gaaagccaat gagagaggag    1740
aatagagctt ccaaggaggc cctgtgccca acaccagaaa gcaagaggct cttaggtccc    1800
cagcatggtg gccaggcctg ctggcagctc tgtgctagaa gctgtgcagg aggccttgcg    1860
aggcctggtc ctgaccgtga tgtggtctgg tcaatgagac gacggtgttt accagagagt    1920
actcttacat ccagaagcct ggcccaaggg ctgatcggtt tttgttttgt ttttgttttt    1980
gctagccagg gtttcttcat atagctctgc ctatcctaga actcactctg gcctcaaact    2040
cagagatcca cctgcctcct gagtgctggg attaaagtcg tcaccacgcc tggcaccaga    2100
ggctgatctt ctctagccaa ctgtacagca aaacatttca catctccagc cttggcttac    2160
```

```
ccctctgcca atcaggatca ctacacaaag ctggaggggt gggacagagg aaggcaagcc      2220
atgtaccagg tgtggggtag acgtggtcag tgcaaacaaa aatggtctcc ttaaatttgg      2280
tgcctggtcc ccgacgctga gggttgggcg tatcacagtg gtgagtctgc taagaacagg      2340
atctgtgtaa gctaggtacc ccctgactga cacacgagaa actctctgct atacttgaaa      2400
aataatatgc aatgtccctt gtggaactga gacacagcac atgcttgtta gagagatttt      2460
gggaaatcca gaaaaatgca aagccagcac aaaccagaat ctcccggggg cagctgctgc      2520
tacttctgta gcttttcttt ttcttccttg cttctctttg agaggcagca tcttgtcttt      2580
ggggatccca gacttggctt atagtcatat gtatccaaca gtaggatctg ggtgcagaca      2640
aggtggtgag aactgaggcc cccaagaggc gccaagggga cacagaaaaa gaccaggttg      2700
cacccctgag gcaggacagc cacttacaaa gcaattctta agaagatcga gaaaggttaa      2760
ggagccacag caactaactt gcccccaggg cctgggtgac cagcctaccc cgcaggtttc      2820
cctaacattg tccagctgtg ctgcatgact gatcccatag gggaaagtcc ttacacgaga      2880
gaaagctaag taagtcttcg agtctcccag acccaaggtt catcctcagt gaaaccagaa      2940
aaggaataga ccctaggaca ggtttcagct ggttctgaaa gttgatgtcc taacttaggg      3000
ctggggtgtg gccacgcaag gtttgtgtaa gtgttgtagg gagaagtggc ccagactggc      3060
attctgtcag gaaaagccag atgctctggc ctgacaggga ccccagagga cacacaggaa      3120
gcctgttcaa aatcaggcct tagggcaaca agtcagcttc agaactgctg ggtttgccca      3180
cgctcctcct gtgggcaggc cttaagctgg tgacaggaga ctgtaagtcc tcacctcaac      3240
atagcccaaa tgcaagagag caaaagggcc tcggtttgga ggtggagcca acccagtact      3300
agttcggctt taatgagcct cgacacagaa gggcctggga gctacgctcc gctcccgcac      3360
cctcccactc cgcggaccag caagttaaaa atgccactat ttgcatgacc ccgcctctcc      3420
ccgcccctcc cgagtggccg gctgggcagg ctatttaaac cccggtcccc gcgttaggca      3480
ggcggtccgc agtcgtgcct cacgccttcc taagctgcgc gggtctccgg agtgcgacgc      3540
gagctagcgg aagggaactg tgcggccagt cggtcgtgcg gtgactgcag ccacctgccc      3600
gagccccgtg gcccgccctc agatcccggc gatgcgcctc ggcgccgcct gggcgctgct      3660
gctggccgca gccctggggc tcgggacgcg cggggtgcgc gctgccgtgg ccctcgccga      3720
cttctacccg ttcggcacga agcgcggcga caccgtcacc ccgaagcagg acgacggcgg      3780
ctcagggctg caaccactct cggtgccctt tccgttcttc ggcgccgagc actccggact      3840
ctacgtgagt aaccccgagc tcgaggggc tccggggagg gcgccgctgc cctccaccc      3900 aactcttgcc gctgccgccg ccagcaactt ggcaccgcgg cagccagagg tggaatgagg      3960
acagcgcttc ctctctcccg cggccaaggc cggacagcga ctggcgggag aggcgtgggc      4020
agggcggggc gagcaaccgc cagggcacct aggcgacagc caggccagcg gaacgcggcg      4080
cgcc                                                                  4084
```

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: consensus
      sequence of EGF-like motif
<220> FEATURE:
<221> NAME/KEY: SITE
<222> LOCATION: (2), (4), (5), (6), (7), (8), (10) and (11)
<223> OTHER INFORMATION: Xaa is any one of natural occurring amino acids

```
<400> SEQUENCE: 32

Cys Xaa Cys Xaa Xaa Xaa Xaa Xaa Gly Xaa Xaa Cys
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: consensus
      sequence of EGF-like motif
<220> FEATURE:
<221> NAME/KEY: misc_feature
<222> LOCATION: (2)..(2)
<223> OTHER INFORMATION: Xaa is any one of natural occurring amino acids
<220> FEATURE:
<221> NAME/KEY: misc_feature
<222> LOCATION: (4)..(5)
<223> OTHER INFORMATION: Xaa is any one of natural occurring amino acids
<220> FEATURE:
<221> NAME/KEY: misc_feature
<222> LOCATION: (6)..(6)
<223> OTHER INFORMATION: Xaa is Gly or Pro
<220> FEATURE:
<221> NAME/KEY: misc_feature
<222> LOCATION: (7)..(7)
<223> OTHER INFORMATION: Xaa is Phe, Tyr or Trp
<220> FEATURE:
<221> NAME/KEY: misc_feature
<222> LOCATION: (8)..(11)
<223> OTHER INFORMATION: Xaa is any one of natural occurring amino acids

<400> SEQUENCE: 33

Cys Xaa Cys Xaa Xaa Xaa Xaa Xaa Xaa Xaa Xaa Cys
 1               5                  10

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: consensus
      sequence of EGF-like motif
<220> FEATURE:
<221> NAME/KEY: misc_feature
<222> LOCATION: (2)..(2)
<223> OTHER INFORMATION: Xaa is any one of natural occurring amino acids
<220> FEATURE:
<221> NAME/KEY: misc_feature
<222> LOCATION: (4)..(5)
<223> OTHER INFORMATION: Xaa is any one of natural occurring amino acids
<220> FEATURE:
<221> NAME/KEY: misc_feature
<222> LOCATION: (6)..(6)
<223> OTHER INFORMATION: Xaa is Gly or Pro
<220> FEATURE:
<221> NAME/KEY: misc_feature
<222> LOCATION: (7)..(7)
<223> OTHER INFORMATION: Xaa is Phe, Tyr or Trp
<220> FEATURE:
<221> NAME/KEY: misc_feature
<222> LOCATION: (8)..(15)
<223> OTHER INFORMATION: Xaa is any one of natural occurring amino acids

<400> SEQUENCE: 34

Cys Xaa Cys Xaa Xaa Xaa Xaa Xaa Xaa Xaa Xaa Xaa Xaa Xaa Xaa Cys
 1               5                  10                  15
```

PROTEIN HAVING AN EGF-LIKE REPEAT SEQUENCE

CROSS REFERENCE TO RELATED APPLICATIONS

This application is a Continuation-In-Part of application Ser. No. 11/219,698 filed on Sep. 7, 2005, now abandoned, which is a Continuation of application Ser. No. 10/959,996 filed on Oct. 8, 2004, now abandoned, which is a Continuation of application Ser. No. 10/795,402 filed on Mar. 9, 2004, now abandoned, which is a Continuation of application Ser. No. 10/404,841 filed on Apr. 2, 2003, now abandoned, which claims benefit of the filing date of Provisional Application No. 60/369,318 filed Apr. 3, 2002, the entire contents of all of which are hereby incorporated by reference and for which priority is claimed under 35 U.S.C. §120 and §119.

FIELD OF THE INVENTION

The present invention relates to a novel bioactive substance having controlling effects on growth and differentiation of undifferentiated cells.

BACKGROUND OF THE INVENTION

Higher animals have a system for supplementing cells after death of cells that form tissues and organs by apoptosis or injury. For example, the amphibian newt can regenerate the limbs and tail if they are cut off, and birds can easily regenerate the nervous system. Mammals have lost such high regenerative capacity, but their liver can regenerate oneself unless it has suffered a severe damage. Additionally, skin, hair, small intestine and hematopoietic cells are regenerated while a mammalian individual is alive. In these tissues, the cell cycle of new cell birth, differentiation and death is repeated as long as the individual is alive. The regenerative capacity depends on cells known as stem cells (Fuchs and Segre, Cell, 100, 143-155, 2000; Weissman Cell, 100, 157-168, 2000). Of various cells types forming tissues and organs, blood cells, nerve cells, vascular endothelial cells and epithelial cells are known to mature through several stages from the undifferentiated cells known as stem cells.

Stem cells have the ability of self-replication (self-renewal) to reproduce oneself by cell division, and the ability of differentiation into specific mature cells. In stem cells, a delicate balance is struck between the self-replication and the differentiation.

For one mechanism of maintaining the balance, the hereinafter-mentioned systems have been proposed.

The localization sites of stem cells are referred to as niches, in which there is a molecular infrastructure that allows the stem cells to be maintained and reproduced. In niches, the stem cells are typically maintained in a growth arrest phase. Once released from the arrested conditions due for example to a tissue injury, the stem cells enter a growth phase, and form a certain population of cells. In this growth process, heterogeneity arises within the population of cells. Some cells re-enter the cell arrest phase and retain their characteristics as stem cells, whereas others statistically express a transcription factor and thereby become destined to differentiate, and subsequently differentiate to different lineages of mature cells. There are thought to be stromal cells in the niches, which can come in contact with the stem cells and trigger a signal for growth arrest in the stem cells.

In the differentiation process to mature cells from so-called precursor cells (or progenitor cells), wherein the precursor cells has left the niches, expressed the transcription factor, and thereby become destined to differentiate, there is a mechanism which controls the process to allow the differentiation to proceed properly. It is thought that other stromal cells, which are different from the stromal cells that trigger a signal for growth arrest in the stem cells, come in contact with the precursor cells, and the precursor cells are subjected to control by certain molecules expressed by these stromal cells, and then that differentiation proceeds properly.

If the identities of the stem cell growth activating/arresting signals possessed by the stromal cells (or the stromal cells population) present in the niches, or those of the precursor cell differentiation control signals, are ascertained, whereby the methods for keeping stem cells in an undifferentiated state for a long time and for controlling differentiation of stem cells, by controlling the growth and arrest of stem cells, can be provided. These methods have many applications in fields such as regenerative medicine, gene therapy and transplantation. Specifically, the methods can be used in hematopoietic stem cell transplantation for a medical treatment of aplastic anemia, or in neural stem cell transplantation for a medical treatment of Alzheimer's disease, but these are only a few examples.

Various studies have been conducted in the past aimed at ascertaining the identities of stem cell growth activating/arresting signals and of precursor cell differentiation control signals.

Leukemia inhibitory factor (LIF) and transforming growth factor (TGF-β) are known to be cytokines which inhibit the differentiation of stem cells. LIF is known to cause the growth of mouse embryonic stem cells without differentiation, but it does not have such effect on mouse hematopoietic stem cells. Also, LIF does not affect human or monkey embryonic stem cells. For TGF-β, there are many reports regarding its inhibitory effects on various types of cells, but no fixed consensus has been obtained regarding its effect on stem cells. Examples of the molecules that control the differentiation of precursor cells are M-CSF, GM-CSF, G-CSF, SCF, TPO and FLK ligands. However such molecules discovered to date cannot account for the differentiation of various types of cells, which suggests the presence of hitherto unidentified molecules.

Recently, Notch, which is a molecule involved in differentiation control of nerve cells in *Drosophila*, has been discovered, and homologs of this molecule have been found in a broad spectrum of organisms across the classification of invertebrates and vertebrates (Artavanis-Tsakonas et al., Science 268, 225-232, 1995). In mammals, it has been shown that the mutation of Notch is related to T cell leukemia and lymphoma (Pear et al., J. Exp. Med. 183, 2283-2291, 1996). It has also demonstrated that expression of activated Notch molecule in myeloblast cell lines causes the inhibition of their innate ability to differentiate into neutrophils by G-CSF (Milner et al., Proc. Natl. Acad. Sci. USA 93, 13014-13019), and the Notch molecule are involved in the determination of the fate of CD4/CD8 cells in T cell differentiation (Robey et al., Cell 87, 483-492, 1996). Therefore, Notch molecules have attracted further attention as differentiation control molecules. Moreover, Delta and Serrate, which are ligands of the Notch molecule, have been identified in *Drosophila* (Kopczynski et al., Genes Dev., 1723-1753, 1988, Thomas et al., Development, 111, 749-761, 1991). X-Delta and Dl11, homologs of Delta, have been identified in the *Xenopus* (Chitnis et al., Nature, 375, 761-766, 1995) and mouse (Bettenhausen et al., Development 121, 2431-2418, 1995), respectively, and Jagged, homologs of Serrate, has been identified in rat and human (Luo et al., Mol. Cell. Biol. 17, 6057-6067, 1997).

From these findings, Notch receptor, and ligands thereof (Delta, Serrate and Jagged), are now attracting attention as cell differentiation and growth control molecules.

Comparing the structures of Notch, Delta and Jagged, the repetition of an EGF (Epidermal Growth Factor)-like domain is commonly found in them (Lindsell et al., Cell, 80, 909-917, 1995). The repetition is referred to as EGF-like repeat sequence or EGF-like repeat motif.

The consensus sequence of the EGF-like domain is C-X-C-X(5)-G-X(2)-C (SEQ ID NO:32) or C-X-C-X(2)-[GP]-[FYW]-X(4, 8)-C (SEQ ID NOS: 33 and 34). These domain structures are found in EGF and many extracellular proteins, and are involved in protein interactions or cellular interactions (Campbell and Bork Curr. Opin. Struct. Biol, 3, 385-392, 1993, Rao et al., Cell, 82, 131-141, 1995).

These suggest that the stromal cells in the niches possess a differentiation and growth control molecule, and the molecule belongs to the Notch, Delta and Jagged family. But the previously identified molecules of the family cannot explain the differentiation and growth control mechanism of stem cells. Accordingly, it is thought that there is also a hitherto unidentified functionally similar molecule as the above molecule possessed by the stromal cells.

A transcriptional induction system is known as a common gene expression control mechanism in animals (Nature, 321: 409-413, 1984). A promoter is generally located 5' upstream to a region that is transcribed into mRNA on a chromosome. Furthermore, through binding or dissociation of a transcription factor to a sequence referred to as the regulatory region within the promoter sequence (transcriptional regulatory sequence), the promoter regulates the transcription level of a gene that is present in the 3' downstream region of the promoter. Therefore, the gene expression level at the transcription stage can be estimated to some extent by measuring promoter activity. In the meantime, promoter activity is not affected in most cases by the 3' downstream region thereof. Hence, promoter activity can be measured by inserting an appropriate reporter gene encoding an enzyme protein or the like into a downstream region of the promoter and then detecting the expression of the reporter gene. Very sensitive and convenient promoter activity measurement has become possible with the use of such a reporter, owing to recent technical innovation. Thus, such promoter activity measurement is used for drug screening and examination of biological functions. For example, screening with the promoter of peroxisome proliferator activated receptor γ (PPARγ) that is a transcription factor for adipose cells differentiation, for a compound that controls the expression of PPARγ was reported (Cell, 99: 239-242, 1999).

Production of transgenic non-human animals using promoters has also been performed. In general, it is difficult to examine the functions of genes that are essential for developmental processes or maintenance of living systems, because deletion of such genes is often lethal in mice. Conditional gene targeting techniques have been used as a potential method for addressing the problem, using a Cre-loxP recombination system under control of a promoter.

Cre recombinase is a site-specific recombinase derived from bacteriophage P1 and specifically recognizes a loxP sequence of 34 base pairs. This enzyme mediates recombination between two loxP sequences, and then a DNA fragment flanked by the two loxP sequences is excised in a cyclic form only under conditions where Cre recombinase is expressed, and the DNA fragment is deleted. For example, lck is a gene that is expressed in T cells and is strongly expressed particularly in the thymus where the development and differentiation of T cells take place. Thus, in a mouse in which a Cre recombinase gene ligated to downstream of the promoter of the lck gene has been introduced, Cre recombinase is specifically expressed only in T cells and the gene flanked by loxP sequences is disrupted (Science, 265: 103-106, 1994, Proc. Natl. Acad. Sci. U.S.A., 92: 12070-12074, 1995).

Mice known to have a Cre recombinase gene under control of such a tissue-specific promoter used therein includes: a mouse having a PO promoter that is expressed in neural crest cells (Dev Biol, 212: 191-203, 1999); a mouse having an L7 promoter that is expressed in Purkinje cells (Genesis, 28, 93-8, 2000); a mouse having a keratin 14 promoter that functions in epidermal basal cells (Horm Res, 54: 296-300, 2000); a mouse having an Mx1 promoter whose activity is induced in the presence of interferon (Science, 269: 1427-1429, 1995); and a mouse having a crystallin promoter that functions in the lens of the eyes (Proc. Natl. Acad. Sci. U.S.A., 89: 6232-6236, 1992). Discovery of a new tissue-specific promoter in addition to these promoters may cause further advancement in functional verification of genes by the conditional gene targeting.

Promoters are important also in production of recombinant proteins. When a protein is recombinantly produced using cells, the gene of a target protein is ligated downstream of a promoter and then the resultant is introduced into and expressed by cells. When animal cells are used as hosts, in general, promoters derived from viruses, such as SV40 and CMV (Proc. Natl. Acad. Sci. U.S.A., 78: 1527-1531; 1981, Nature, 329: 840-842, 1987), an actin gene promoter (Gene, 108: 193-200, 1991), and an elongation factor gene promoter (Nucleic Acids Res., 18: 5322, 1990) are used. However, the strength of the activity of these promoters differs depending on the types of proteins to be expressed and host cell types. Hence, it is necessary to examine such combination to select an optimum promoter. Therefore, provision of a new promoter is always desired for more effective production of individual proteins.

SUMMARY OF THE INVENTION

It is an object of the present invention, which was conceived in view of the above technical backgrounds, to provide a novel molecule by discovering a protein molecule which can affect stem cells to trigger the growth arrest signal in stem cells, or a protein molecule which can affect precursor cells to control their differentiation and growth other than Delta and Jagged; and determining the genetic sequence and amino acid sequence of that novel molecule. It is further object of the present invention to provide a pharmaceutical composition which comprises such molecule as an active ingredient for treating diseases caused by cell or tissue damage, based on the differentiation and growth control effect which is one of the features of this molecule. It is a further object of the present invention to provide a method for gene therapy by using the genes of this molecule. It is yet another object of the present invention to provide a method of regenerative medicine by discovering a molecule that controls stem cell or precursor cell growth and differentiation. It is further object of the present invention to provide a novel tissue specific promoter and use thereof.

We have cloned the gene of stem cell/precursor cell differentiation and growth controlling molecules that contain an EGF-like repeat sequence, from the mRNA of stromal cell lines considered to present in the "niches", by RT-PCR method using primers designed based on the amino acid sequence which is appeared with a relatively high frequency in EGF-like motif sequences. Primers have been designed based on sequence information of the resulting cDNA fragments, and the cDNA which encodes the full amino acid sequence of the novel molecule containing an EGF-like repeat sequence has been successfully isolated by the 3' and 5'RACE method. By using this cDNA, the cells that express the above gene has been detected, transformed cells have been generated, antibodies have been produced, and in vivo localization of the expression product of the gene have been identified. The protein molecule of the present invention, which contains an EGF-like repeat sequence or EGF-like repeat motif, has been named "stromal cell-derived EGF-like repeat containing factor", which is abbreviated as SELF. Then, the nucleic acid molecule of the present invention, which encodes such SELF protein, has been called also SELF gene. In addition, we isolated a promoter sequence of SELF gene (SELF promoter) and assayed functions of SELF protein.

The present invention generally relates to SELF protein, SELF gene and SELF promoter, and their use.

One aspect of the present invention is an isolated protein comprising the amino acid sequence as shown in SEQ ID NO: 2, 3, 4 or 24.

Another aspect of the present invention is an isolated protein comprising an amino acid sequence having one or more amino acids deleted, substituted or added in the amino acid sequence as shown in SEQ ID NO: 2, 3, 4 or 24, wherein the protein contains an EGF-like repeat motif and has bioactivity as a growth and differentiation controlling factor.

Another aspect of the present invention is an isolated protein, wherein the protein has at least 80% homology to a protein comprising the amino acid sequence as shown in SEQ ID NO: 2, 3, 4 or 24, contains the EGF-like repeat motif, and has bioactivity as the growth and differentiation controlling factor.

Another aspect of the present invention is an isolated protein, wherein the protein has at least 90% homology to a protein comprising the amino acid sequence as shown in SEQ ID NO: 2, 3, 4 or 24, contains the EGF-like repeat motif, and has bioactivity as the growth and differentiation controlling factor.

Another aspect of the present invention is an isolated nucleic acid which encodes a protein comprising the amino acid sequence as shown in SEQ ID NO: 2, 3, 4 or 24.

Another aspect of the present invention is an isolated nucleic acid comprising the nucleotide sequence as shown in SEQ ID NO: 1.

Another aspect of the present invention is an isolated nucleic acid consisting of the nucleotide sequence of nucleotides 157 to 4365 of SEQ ID NO: 1.

Another aspect of the present invention is an isolated nucleic acid consisting of the nucleotide sequence of nucleotides 1 to 1251 of SEQ ID NO: 1.

Another aspect of the present invention is an isolated nucleic acid consisting of a nucleotide sequence of nucleotides 1624 to 2174 of SEQ ID NO: 1.

Another aspect of the present invention is an isolated nucleic acid comprising a nucleotide sequence as shown in SEQ ID NO: 23.

Another aspect of the present invention is an isolated nucleic acid which hybridizes under stringent conditions with the above nucleic acid, and encodes a protein containing the EGF-like repeat motif and having bioactivity as the growth and differentiation controlling factor.

Another aspect of the present invention is an isolated nucleic acid comprising a nucleotide sequence which has at least 80% homology with the above nucleic acid, and encodes a protein containing the EGF-like repeat motif and having bioactivity as the growth and differentiation controlling factor.

Another aspect of the present invention is an isolated nucleic acid comprising a nucleotide sequence which has at least 90% homology with the above nucleic acid, and encodes a protein containing the EGF-like repeat motif and having bioactivity as the growth and differentiation controlling factor.

Another aspect of the present invention is a recombinant DNA construct, comprising the above nucleic acid or part thereof, and a vector DNA functionally linked thereto wherein the vector can be expressed in a host cell. Preferably, the present invention relates to a recombinant vector comprising the above nucleic acid, for example, a recombinant expression vector capable of expressing the above nucleic acid in a host cell.

Another aspect of the present invention is a cell transformed with the above recombinant vector.

Another aspect of the present invention is a method of producing the above protein comprising culturing the above transformed cell, and recovering a produced protein from the culture medium or cultured cells.

Another aspect of the present invention is an antibody, which specifically binds to the above protein or fragments of the protein. For example, an antibody, which specifically recognizes a protein comprising the amino acid sequence as shown in SEQ ID NO: 2, 3, 4 or 24 is provided.

Another aspect of the present invention is an antibody, which specifically recognizes a protein comprising the amino acid sequence of amino acids 1390 to 1403 of SEQ ID NO: 2.

Another aspect of the present invention is an antibody, which specifically recognizes a protein comprising the amino acid sequence of amino acids 235 to 432 of SEQ ID NO: 2.

Another aspect of the present invention is a method of controlling the growth and differentiation of undifferentiated cells with the above protein. More specifically, the present invention relates to a method for controlling the growth and differentiation of undifferentiated cells, comprising contacting the above protein with undifferentiated cells. The undifferentiated cells are preferably hematopoietic undifferentiated cells.

Further, another aspect of the present invention is a pharmaceutical composition containing the above protein, and/or a recombinant expression vector comprising the above nucleic acid. Preferably, the pharmaceutical composition of the present invention further comprises a vascular endothelial growth factor inhibitor.

Another aspect of the present invention is a pharmaceutical kit which further comprises a vascular endothelial growth factor inhibitor, or a recombinant expression vector encoding a vascular endothelial growth factor inhibitor, together with the above protein, or a recombinant expression vector comprising the above nucleic acid.

Another aspect of the present invention is a method for controlling the growth and differentiation of undifferentiated cells, comprising administering to a subject the above protein, or a recombinant expression vector comprising the above nucleic acid.

More particularly, the present invention relates to a method for stimulating hematopoiesis comprising administering the above protein or a recombinant expression vector comprising the above nucleic acid to a subject. The present invention also relates to a method for treating or preventing hypocythemia due to the hematopoiesis-stimulating effects. Preferably, the hypocythemia is a cytopenic condition in the subject suffering from anaplastic anemia, myelodysplastic syndrome, or leukemia; or following cancer chemotherapy, radiation therapy, or bone marrow transplantation.

Further, the present invention relates to a method for inhibiting the growth and differentiation of smooth muscle cells, a method for inhibiting angiogenesis, and a method for treating or preventing angiogenic disease, by administering the above protein or the recombinant expression vector comprising the above nucleic acid to a subject. The preferred examples of the angiogenic disease include malignant tumors, diabetic retinopathy, retinopathy of prematurity, rubeosis iridis, sickle-cell retinopathy, central retinal vein occlusion, central retinal artery occlusion, branch retinal vein occlusion, age-related macular degeneration, neovascular glaucoma, rheumatoid arthritis, psoriasis, ascites cancer, malignant pleural effusion, Crow-Fukase syndrome, ovarian hyperstimulation syndrome, atherosclerosis, cerebral infarction, cardiac infarction and peripheral artery occlusive disease. In these methods, the effects of inhibiting blood vessel formation can be enhanced by further administering a vascular endothelial growth factor inhibitor or a recombinant expression vector encoding the vascular endothelial growth factor inhibitor to the subject.

Another aspect of the present invention is an isolated promoter comprising a nucleic acid selected from the group consisting of: (a) an isolated nucleic acid consisting of the nucleotide sequence of nucleotides 1 to 3487 of SEQ ID NO: 31; (b) an isolated nucleic acid consisting of at least 114 contiguous nucleotides of SEQ ID NO: 31 wherein said at least 114 contiguous nucleotides comprise nucleotides 3374 to 3487 of SEQ ID NO: 31; (c) an isolated nucleic acid hybridizing under stringent conditions with the nucleic acid of the above (b); (d) an isolated nucleic acid comprising a nucleotide sequence having at least 70% homology to the nucleic acid of the above (b); (e) an isolated nucleic acid comprising a nucleotide sequence having one or more nucleotides deleted, substituted or added in the nucleic acid of the above (b).

Another aspect of the present invention is an isolated promoter according to the above (b) consisting of the nucleotide sequence of nucleotides 3374 to 3487 of SEQ ID NO: 31.

Another aspect of the present invention is an isolated promoter according to the above (b) comprising the nucleotide sequence of nucleotides 3299 to 3487 of SEQ ID NO: 31.

Another aspect of the present invention is an isolated promoter according to the above (b) comprising the nucleotide sequence of nucleotides 2796 to 3487 of SEQ ID NO: 31.

Another aspect of the present invention is a recombinant vector comprising the above promoter. Preferably, the present invention relates to a recombinant vector comprising a structural gene (i.e., an exogenous gene) under the expression control of the above promoter, or a recombinant vector further comprising a viral enhancer sequence inserted adjacent to said promoter. Another aspect of the present invention is a cell transformed with the above recombinant vector. Another aspect of the present invention is a transgenic non-human animal transformed with the above recombinant vector.

Further another aspect of the present invention is a method for screening for a substance that enhances or inhibits a SELF promoter activity comprising containing the above transformed cell with a test substance.

Another aspect of the present invention is a kit for screening for a substance that enhances or inhibits a SELF promoter activity comprising the above transformed cell.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 4 is a photograph showing the SELF protein produced in the culture supernatants of PA6 cells, as examined by the Western blotting. Lane 1: a supernatant sample of cultured stromal cells PA6 in a serum-free medium, that has been concentrated 50 times with 50% saturated ammonium sulfate; and Lane 2: a supernatant sample prepared by culturing stromal cells in a medium containing 10% FCS.

DETAILED DESCRIPTION OF THE INVENTION

Figure 1:
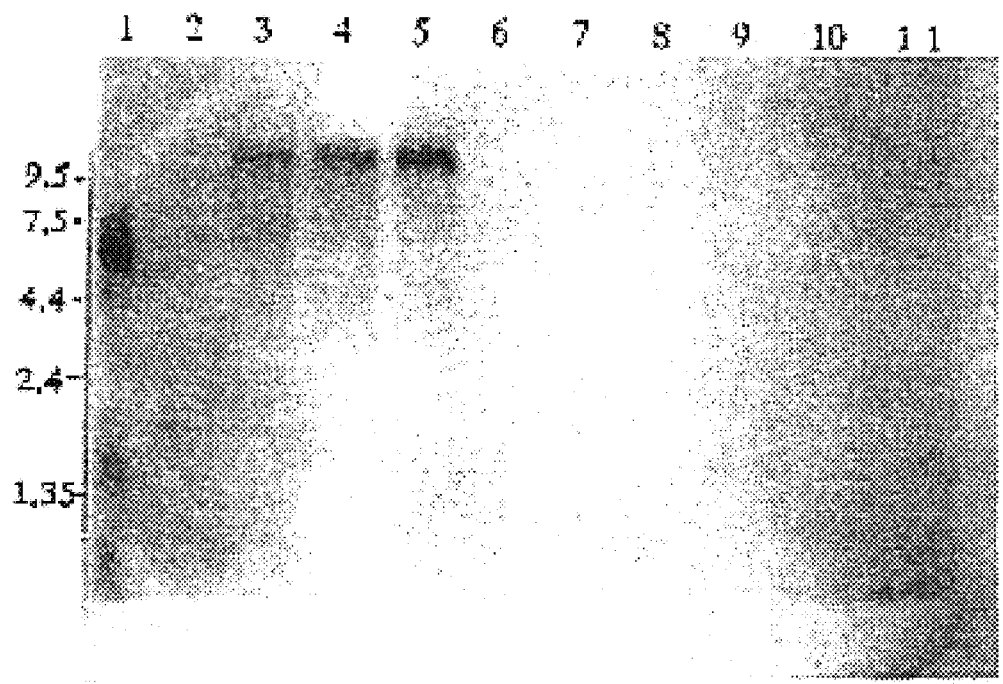
FIG. 1 is a photograph showing SELF mRNA expression in various mouse cell lines. The expression of the SELF gene was examined for various mouse cell lines by the Northern blot method using a SELF cDNA fragment. Lane 1: marker; Lane 2: human fibroblast (DIP2); Lane 3: MC3T3E1 cells; Lane 4: MC3T3E1 cells (cultured for 60 days); Lane 5: MC3T3E1 cells (stimulated with TGF-β); Lane 6: hepatic parenchymal cells (on day 2 of culture); Lane 7: hepatic parenchymal cells (on day 4 of culture); Lane 8: hepatic parenchymal cells (on day 6 of culture); Lane 9: SPB2.4 cells (LGL strain); Lane 10: GRSL cells (T cells); and Lane 11: J774.1 cells (macrophage).

The present invention will now be described in detail. The necessary experiments for the present invention, such as preparation of mRNA, production of cDNA, RT-PCR method, RACE method, DNA sequencing and identification of gene expression by Northern blot, can be performed according to methods described in standard laboratory books. An example is "Molecular Cloning, A Laboratory Manual", 2001, Eds., Sambrook, J & Russell, D W., Cold Spring Harbor Laboratory Press.

1. Obtainment of SELF Gene

The genes of the present invention, which encode the novel protein SELF containing the EGF-like repeat motif, can be cloned by searching any genes for the amino acid sequence of the EGF-like motif found in Notch and Delta, obtaining a sequence appeared in the sequences of the EGF-like motif with a relatively high frequency, and using the obtained sequence as an indicator. Examples of the amino acid sequence of EGF-like motif are CPPGF (SEQ ID NO: 18) and NGGTC (SEQ ID NO: 19), but it is not limited thereto. The genes can be cloned by designing degenerate primers based on the amino acid sequence, synthesizing the primers on a DNA synthesizer, purifying the synthesized primers, and performing RT-PCR with the purified primers.

Stromal cells may be used as the mRNA source for RT-PCR using the primers. The stromal cells may be cell lines that support the growth and differentiation of stem cells or precursor cells, preferably PA6, OP9, ST2, more preferably PA6. mRNA are extracted from the stromal cells, and amplified by RT-PCR.

cDNA fragments which have been amplified from PA6 mRNAs by the RT-PCR method, are cloned in various vectors, and the DNA sequences contained in the clones are determined. By comparing the determined genetic sequences of the DNAs with genetic sequences corresponding to well-known proteins containing the EGF-like repeat sequence such as Notch and Delta, it can be verified that a partial fragment of SELF gene has been cloned.

A coding region of the gene fragment can be cloned by labeling the partially cloned gene as mentioned above with e.g. a radioactive isotope, and screening cDNA library prepared from mRNA extracted from stromal cells using e.g. hybridization method. Alternatively, a coding region of the gene fragment can be also cloned by RACE method using primers which are designed based on the sequence information of the partial cloned gene. RACE method allows one to obtain the full-length sequence of the gene encoding SELF protein containing the EGF-like repeat motif.

The cDNA nucleotide sequence of the invention, which encodes a mouse novel protein SELF containing an EGF-like repeat motif, is shown as SEQ ID NO: 1 in the sequence listing. As a result of homology searching between the DNA sequence shown by SEQ ID NO: 1 and the DNA sequence of known genes, it has been found that the DNA sequence shown by SEQ ID NO: 1 is homologous to the genes encoding the protein containing the EGF-like repeat motif, such as human Tan1, mouse Notch 4, rat Jagged 2 and human Delta.

Further, human SELF cDNA can be obtained by PCR amplification using cDNA derived from human spleen as a template and primers or probes designed from the sequence information of the above mouse SELF DNA, and then sequenced, as described in the after-mentioned Examples. The nucleotide sequence of human SELF cDNA as obtained in this way is typically shown in SEQ ID NO: 23 and the corresponding amino acid sequence is shown in SEQ ID NO: 24.

Figure 6B:
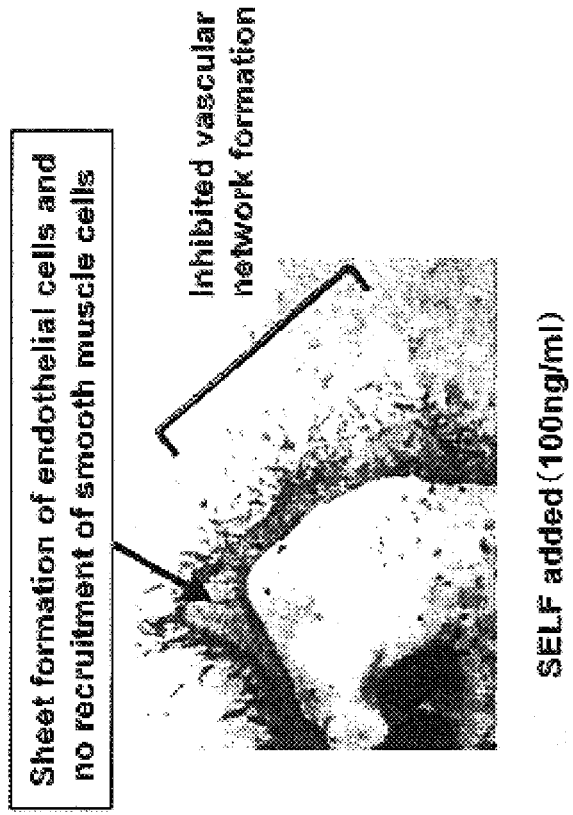
FIG. 6A and FIG. 6B show photographs showing the effects of the SELF protein on the growth and differentiation of smooth muscle cells as examined in Example 10. Photograph in FIG. 6A: no SELF protein was added. In this case, as shown in the figure, vascular network was formed. Photograph in FIG. 6B: the SELF protein (100 ng/ml) was added to a culture system. In this case, sheet formation of endothelial cells was observed, but no recruitment of smooth muscle cells was found (the site indicated with an arrow). Furthermore, vascular network formation was also inhibited.
Figure 6A:
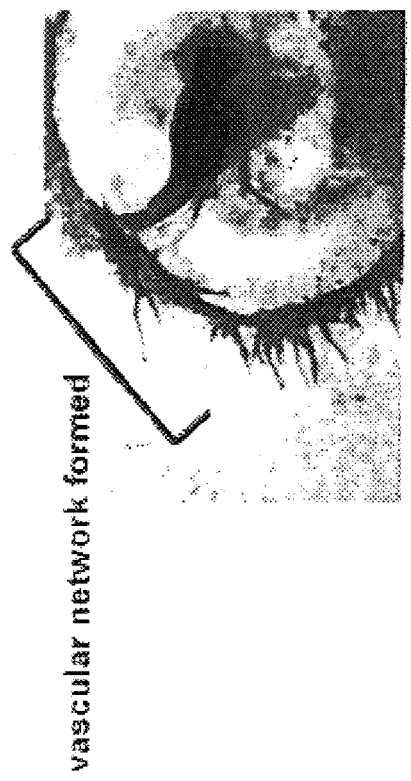

It has also been found that the SELF gene of the invention is homologous to the nucleotide sequences described in International Publication No. WO 01/32873 A1 (FIG. 4 and FIG. 6 of WO 01/32873 A1; GenBank accession Nos. NM_172463 and XM_059482). The nucleotide sequence shown in FIG. 4A of International Publication No. WO 01/32873A1, which has been derived from rat, shows homology with the nucleotide sequence between the nucleotides 1342 to 4368 of SEQ ID NO: 1 of the present invention. The nucleotide sequence shown in FIGS. 6A and 6B of International Publication No. WO 01/32873A1, which has been derived from human, shows homology with the nucleotide sequence between the nucleotides 1252 to 4368 of SEQ ID NO: 1. However, the physiological function of a protein encoded by the nucleotide sequence of NM_172463 has been unresolved. The nucleotide sequence of XM_059482 contains additional 192 nucleotides within the above shown sequence of human SELF gene, and the physiological function of a protein encoded by the nucleotide sequence of XM_059482 sequence has not yet been determined.

The protein encoded by the gene disclosed in International Publication No. WO 01/32873A1 is an intracellular transcription factor, which regulates insulin signal transduction. On the other hand, the SELF protein encoded by the gene of the present invention is secreted extracellularly, has bioactivity as a growth and differentiation controlling factor, in particular, hematopoiesis-stimulating effects, and/or inhibiting effects on the growth and differentiation of smooth muscle cells. Further, the SELF protein can act directly on cells. Hence, the SELF gene of the present invention is different from any known genes and is therefore a novel gene.

The nucleotide sequence of the polynucleotide which encode the polypeptide comprising the amino acid sequences of SEQ ID NO: 2, 3 and 4 is also shown in SEQ ID NO: 1. The amino acid sequence of SEQ ID NO: 2 corresponds to the nucleotide sequence of nucleotides 157 to 4365 of SEQ ID NO: 1. The amino acid sequence of SEQ ID NO: 3 corresponds to the nucleotide sequence of nucleotides 223 to 4365 of SEQ ID NO: 1. The amino acid sequence of SEQ ID NO: 3 shows a SELF protein devoid of the signal sequence. The amino acid sequence of SEQ ID NO: 4 corresponds to the nucleotide sequence of nucleotides 223 to 1317 of SEQ ID NO: 1. The amino acid sequence of SEQ ID NO: 4 shows a part of the SELF protein devoid of the signal sequence (SEQ ID NO: 3).

It may be often found for the genetic sequence of the present invention that the DNA sequence of its chromosomal DNA or cDNA, which is obtained from nature, is mutated without causing any mutation at the amino acid level because of degeneracy of the genetic code. Also, the DNA sequences of the 5' untranslated region and 3' untranslated region may have high variability since the regions are not involved in definition of the amino acid sequence of the protein. The varied nucleotide sequences based on the degeneracy of the genetic code as mentioned above, are also included in the nucleic acids (or polynucleotides) of the present invention. Further, variants of the protein of the invention produced by alternative splicing are also included in the proteins of the present invention, provided that the variants retain the characteristics of the SELF proteins comprising the amino acid sequence of SEQ ID NO: 2, 3, 4 or 24 in the sequence listing.

The present invention further includes the other animal-derived SELF nucleic acids corresponding to the nucleic acids comprising the nucleotide sequences of SEQ ID NOs: 1 and 23, and their partial fragments; and the other animal-derived proteins corresponding to the proteins comprising the amino acid sequences of SEQ ID NOs: 2, 3, 4 and 24 and their partial fragments.

In addition, nucleic acids of the present invention include not only the nucleic acid comprising the nucleotide sequence of SEQ ID NO: 1 (i.e., nucleotides 1 to 5245 of SEQ ID NO: 1), but also the nucleic acid having the nucleotide sequence of nucleotides 1 to 1251 of SEQ ID NO: 1, the nucleic acid having the nucleotide sequence of nucleotides 1624 to 2174 of SEQ ID NO: 1.

Nucleic acids of the present invention also includes nucleic acids which hybridizes under stringent conditions with the DNA comprising the nucleotide sequence of SEQ ID NO: 1, the nucleic acid having the nucleotide sequence of nucleotides 1 to 1251 of SEQ ID NO: 1 or the nucleic acid having the nucleotide sequence of nucleotides 1624 to 2174 of SEQ ID NO: 1 or the nucleic acid comprising the nucleotide sequence of SEQ ID NO: 23 (i.e, nucleotides 1 to 4242 of SEQ ID NO: 23). Such nucleic acids preferably contain the nucleotide sequences encoding EGF-like repeat motifs, and encode proteins having bioactivity as a growth and differentiation controlling factor.

In the present invention, "stringent conditions" means conditions defined by carrying out hybridization at 68° C. in the presence of 0.7-1.0 M NaCl on a DNA-immobilized filter, and subsequently washing the filter at 68° C. with the 0.1-2.0×SSC solution (1×SSC contains 150 mM NaCl and 15 mM sodium citrate), under which conditions detection of DNA of interest can be accomplished, or the substantially equivalent conditions. The "bioactivity as a growth and differentiation controlling factor" means an effect of controlling the growth and differentiation on undifferentiated cells. "Undifferentiated cells" as used herein refers to stem cells or precursor cells. Stem cells are defined as cells which can reproduce themselves and can differentiate into many types of cell lineages. These include myeloid stem cells, neural crest cells, skin stem cells, neural stem cells, muscle stem cells, hematopoietic stem cells and liver stem cells, and each of them has the ability of self-replication and the ability of generating the cell lineages. Precursor cells refer to the cell lineage-committed cells from each stem cell, which have not achieved their final differentiation. Preferably, the undifferentiated cells may be hematopoietic undifferentiated cells, for example, hematopoietic stem cells or hematopoietic progenitor cells. Alternatively, the undifferentiated cells may be preferably myeloid stem cells, neural crest cells, mesenchymal stem cells, smooth muscle progenitor cells or ES cells (embryonic stem cells).

"Controlling effects on the growth and differentiation" means an effect that allows the differentiation and/or growth of undifferentiated cells to be autonomously or heteronomously promoted or inhibited. Specifically, this term means an effect of causing undifferentiated cells to 1) reach a differentiating state, 2) remain in their present state without differentiating, or 3) reach a replicating state. Any molecules having the differentiation and growth control effect may be used, as long as they affect, directly or indirectly, the undifferentiated cells in a body or a culture system and result in showing the effect. For example, such effects of the molecules may be demonstrated by adding the molecules to cultured marrow cells to produce blood cells or osteoclasts.

In the preferred aspect of the invention, the controlling effect on growth and differentiation of undifferentiated cells with respect to SELF protein of the present invention may be controlling effects on growth and differentiation of hematopoietic undifferentiated cells, for example, hematopoiesis-stimulating effects. Alternatively, the controlling effect on growth and differentiation of undifferentiated cells may be inhibiting effects on the growth and differentiation of undifferentiated cells into smooth muscle cells.

The term "SELF," herein described, refers to SELF protein and/or SELF gene.

Nucleic acids of the present invention further include nucleic acids comprising a nucleotide sequence having at least 70% homology, preferably at least 80% homology, more preferably 90% homology, and still more preferably 95%, 96%, 97%, 98% or 99% homology, with the nucleotide sequence of SEQ ID NO: 1, the nucleotide sequence of nucleotides 1 to 1251 of SEQ ID NO: 1, the nucleotide sequence of nucleotides 1624 to 2174 of SEQ ID NO: 1, or the nucleotide sequence of SEQ ID NO: 23, wherein the homology is calculated using BLAST (e.g., with the default or initial setting parameters of BLAST).

Mutations can be introduced into the genes of the present invention by known techniques such as the Kunkel method or Gapped duplex method or a technique based thereon, e.g., with a mutagenesis kit based on site-specific mutagenesis method (e.g., Mutan™-K (TAKARA) or Mutan™-G (TAKARA), or a kit of TAKARA LA PC™ in vitro Mutagenesis series).

Once the nucleotide sequences of genes of the present invention are determined, the genes of the present invention can then be obtained by chemical synthesis, by PCR using cDNA as a template, or by hybridization using DNA fragments having this nucleotide sequence as a probe.

The recombinant vectors of the present invention can be obtained by ligation (insertion) of a gene of the present invention into a suitable vector. There is no particular limitation on the vectors into which a gene of the present invention is inserted, provided that they are replicable in the host, e.g., plasmid DNA or phage DNA.

Examples of plasmid DNA are plasmids derived from *E. coli* (e.g., pBR322, pBR325, pUC118, pUC119, pUC18, pUC19), plasmids derived from *Bacillus subtilis* (e.g., pUB110, pTP5), and plasmids derived from yeast (e.g., YEp13, YEp24, YCp50). Examples of phage DNA are λ phage (Charon 4A, Charon 21A, EMBL 3, EMBL 4, λ gt10, λ gt11, λ ZAP). Further, detoxified DNA viruses or RNA viruses, such as retroviruses, adenoviruses, adeno-associated viruses, herpes viruses, vaccinia viruses, poxviruses, polioviruses, Sinbis virus, Sendai virus, SV40 and Human Immunodeficiency Virus (HIV); animal viruses such as pCI-neo, pcDNA3, or pZeoSV, and insect virus vectors, e.g., baculoviruses, can also be used.

In order to insert the genes of the present invention into the vector, for example, purified DNA is first cleaved with one or more suitable restriction enzymes, and the resulting gene fragment is then inserted and ligated into a restriction enzyme site or a multi-cloning site of a suitable vector DNA.

The genes of the present invention need to be inserted into a vector in a manner that the gene can perform its function. For this purpose, the vectors of the invention may be optionally contain other fragments, including those containing a cis-element such as an enhancer, a splicing signal consisting of a splice donor site on the 5' terminal side of intron and a splice acceptor site on the 3' terminal side of intron, a poly A addition signal, a selectable marker or a ribosome binding sequence (SD sequence), in addition to a promoter and the gene of the present invention. Examples of selectable marker include dihydrofolic acid reductase gene, ampicillin resistant gene, and neomycin resistant gene.

The transformants of the present invention, for example transformed cells, can be obtained by introducing a recombinant vector of the present invention into a host such that the gene of interest can be expressed. There is no particular limitation on the host used in the invention provided that the DNA of the present invention can be expressed in the host. Examples of the host include bacteria belonging to the genus *Escherichia* (such as *Escherichia coli*), the genus *Bacillus* (such as *Bacillus subtilis*), and the genus *Pseudomonas* (such as *Pseudomonas putida*); yeasts such as *Saccharomyces cerevisiae* or *Schizosaccharomyces pombe*; animal cells such as COS cells or CHO cells; and insect cells such as Sf21.

When *Escherichia coli* (*E. coli*) is used as the host, preferably the recombinant vectors of the present invention are autonomously replicable in the host cells, and contain a promoter, a ribosome binding sequence, a gene of the present invention and a transcription termination sequence. The vectors may also contain a gene for controlling the promoter.

Examples of *E. coli* include *Escherichia coli* DH1. Example of grass *bacillus* is *Bacillus subtilis*. However the host bacteria used in the invention is not limited to these organisms.

There is no limitation on the promoters when bacteria are used as the host, provided that it can be expressed in the host such as *E. coli*. For example, the promoters derived from *E. coli*, such as trp promoter, lac promoter, $P_L$ promoter and $P_R$ promoter, and phage-based promoters can be used. Any artificially modified promoter, such as tac promoter, can also be used.

There is no limitation on the methods of introducing a recombinant vector into bacteria used in the invention, provided that it can introduce DNA into bacteria. Examples of the method are a method using calcium ion [Cohen, S, N. et al.: Proc. Natl. Acad. Sci., USA, 69:2110 (1972)], and electroporation method.

When yeast is used as the host, *Saccharomyces cerevisiae*, *Schizosaccharomyces pombe* or *Pichia pastoris*, etc. can be used. There is no limitation on the promoters when yeast is used as the host, provided that it can be expressed in the yeast, and e.g., gall promoter, ga110 promoter, heat shock protein promoter, MFα1 promoter, PH05 promoter, PGK promoter, GAP promoter, ADH promoter or AOX1 promoter can be used.

There is no limitation on the methods of introducing a recombinant vector into the yeast, provided that it can introduce DNA into yeast. Examples are electroporation method [Becker, D. M. et al.: Methods. Enzymol., 194:182 (1990)], spheroplast method [Hinnen, A. et al.: Proc. Natl. Acad. Sci., USA, 75:1929 (1978)] and lithium acetate method [Itoh, H.: J. Bacteriol., 153:163 (1983)].

When animal cells are used as the host, for example, monkey cell COS-7, Vero, Chinese hamster ovarian cell (CHO cell), mouse L cell, rat GH3 or human FL cell, can be used. In this case, for example, SRα promoter, SV40 promoter, LTR promoter or CMV promoter, can be used as the promoter. The recombinant vectors can be introduced into the animal cells by, e.g., electroporation method, calcium phosphate method or lipofection method.

When insect cells are used as host, for example, Sf21 cells can be used. The recombinant vectors can be introduced into the insect cells by e.g., calcium phosphate method, lipofection method or electroporation method.

In this specification, both "nucleic acid" and "polynucleotide" mean compounds wherein nucleotides are polymerized, and no special distinction is made between them. Moreover, both nucleic acids and polynucleotides include DNA and RNA.

2. Preparation of the Proteins of the Present Invention

The proteins of the present invention are proteins comprising an amino acid sequence encoded by the SELF gene of the present invention; or proteins comprising an amino acid sequence having one or more amino acids deleted, substituted or added in the above amino acid sequences, containing an EGF-like repeat motif, and having bioactivity as a growth and differentiation controlling factor, preferably a hematopoiesis-stimulating effect and an inhibiting effect on growth and differentiation of smooth muscle cells.

The SELF proteins containing the EGF-like repeat motif of the invention have the particular structures as follows. In the amino acid sequence as shown in SEQ ID NO: 2 in the sequence listing, the sequence of amino acids 1 to 22 of SEQ ID NO: 2 is predicted to be a signal peptide region with the method of von Heijin (Nucleic Acids Res. 14, 4683-4690, 1986). The amino acid sequence of amino acids 38 to 40 is cell attachment sequence RGD. The amino acid sequence of amino acids 1081 to 1084 is glycosaminoglycan attachment sequence. There are ten sites where asparagine-linked sugar is added to, which are respectively the amino acid no. 408, no. 484, no. 536, no. 712, no. 886, no. 977, no. 1015, no. 1109, no. 1139, no. 1298 of SEQ ID NO: 2. EGF-like motif is found at 15 sites. The first EGF-like motif sequence is from amino acid no. 278 cysteine to amino acid no. 308 cysteine, the second EGF-like motif sequence is from amino acid no. 315 cysteine to amino acid no. 346 cysteine, the third EGF-like motif sequence is from amino acid no. 353 cysteine to amino acid no. 384 cysteine, the fourth EGF-like motif sequence is from amino acid no. 387 cysteine to amino acid no. 422 cysteine, the fifth EGF-like motif sequence is from amino acid no. 433 cysteine to amino acid no. 464 cysteine, the sixth EGF-like motif sequence is from amino acid no. 472 cysteine to amino acid no. 499 cysteine, the seventh EGF-like motif sequence is from amino acid no. 545 cysteine to amino acid no. 576 cysteine, the eighth EGF-like motif sequence is from amino acid no. 584 cysteine to amino acid no. 615 cysteine, the ninth EGF-like motif sequence is from amino acid no. 623 cysteine to amino acid no. 654 cysteine, the tenth EGF-like motif sequence is from amino acid no. 661 cysteine to amino acid no. 692 cysteine, the eleventh EGF-like motif sequence is from amino acid no. 753 cysteine to amino acid no. 788 cysteine, the twelfth EGF-like motif sequence is from amino acid no. 791 glutamic acid to amino acid no. 826 cysteine, the thirteenth EGF-like motif sequence is from amino acid no. 833 cysteine to amino acid no. 864 cysteine, the fourteenth EGF-like motif sequence is from amino acid no. 871 cysteine to amino acid no. 902 cysteine, and the fifteenth EGF-like motif sequence is from amino acid no. 1310 cysteine to amino acid no. 1341 cysteine.

The fourth EGF-like sequence, the eleventh EGF-like sequence and the twelfth EGF-like sequence are calcium-linked EGF-like sequences and are involved in protein interactions. Also, there is a sequence similar to an EGF-like sequence between the sixth EGF-like sequence and the seventh EGF-like sequence at one location.

Further, the sequence of amino acids 1 to 29 of SEQ ID NO: 24 is predicted to be a signal peptide region by searching with a software SOSUI (http://sosui.proteome.bio.tuat.ac.jp/sosuiframe0.html). The amino acid sequence of amino acids 38 to 40 is cell attachment sequence RGD. There are thirteen sites where asparagine-linked sugar is added to, which are respectively the amino acid no. 145, no. 204, no. 368, no. 408, no. 484, no. 536, no. 712, no. 886, no. 977, no. 1015, no. 1109, no. 1139, no. 1310 of SEQ ID NO: 24. EGF-like motif is found at 15 sites. The first EGF-like motif sequence is from amino acid no. 278 cysteine to amino acid no. 308 cysteine, the second EGF-like motif sequence is from amino acid no. 315 cysteine to amino acid no. 346 cysteine, the third EGF-like motif sequence is from amino acid no. 353 cysteine to amino acid no. 384 cysteine, the fourth EGF-like motif sequence is from amino acid no. 387 cysteine to amino acid no. 422 cysteine, the fifth EGF-like motif sequence is from amino acid no. 433 cysteine to amino acid no. 464 cysteine, the sixth EGF-like motif sequence is from amino acid no. 472 cysteine to amino acid no. 499 cysteine, the seventh EGF-like motif sequence is from amino acid no. 545 cysteine to amino acid no. 576 cysteine, the eighth EGF-like motif sequence is from amino acid no. 584 cysteine to amino acid no. 615 cysteine, the ninth EGF-like motif sequence is from amino acid no. 623 cysteine to amino acid no. 654 cysteine, the tenth EGF-like motif sequence is from amino acid no. 661 cysteine to amino acid no. 692 cysteine, the eleventh EGF-like motif sequence is from amino acid no. 753 cysteine to amino acid no. 788 cysteine, the twelfth EGF-like motif sequence is from amino acid no. 791 glutamic acid to amino acid no. 826 cysteine, the thirteenth EGF-like motif sequence is from amino acid no. 833 cysteine to amino acid no. 864 cysteine, the fourteenth EGF-like motif sequence is from amino acid no. 871 cysteine to amino acid no. 902 cysteine, and the fifteenth EGF-like motif sequence is from amino acid no. 1311 cysteine to amino acid no. 1342 cysteine.

The proteins of the present invention include a protein consisting of the amino acid sequences of SEQ ID NOs: 2, 3, 4 and 24 in the sequence listing, but also include variants based on intraspecies mutations known to occur in nature, mutations such as allelic mutations or point mutations which can be produced artificially, provided that they retain the characteristics of the proteins of SEQ ID NOs: 2, 3, 4 and 24 in the sequence listing.

The proteins of the invention include a protein consisting of an amino acid sequence having one or more amino acids deleted, substituted or added in the amino acid sequence as shown in SEQ ID NO: 2, 3, 4 or 24, wherein the protein contains an EGF-like repeat motif and has bioactivity as the growth and differentiation controlling factor, for example, preferably, the hematopoiesis-stimulating effect and the inhibiting effect on growth and differentiation of smooth muscle cells.

Herein, "one or more amino acids deleted, substituted or added", means, but are not limited to, that preferably 1-50 amino acids, more preferably one to several amino acids or most preferably 1-3 amino acids are deleted, substituted or added in the given amino acid sequence. Examples of the amino acid sequence having one or more amino acids deleted, substituted or added in the amino acid sequence as shown in SEQ ID NO: 2, 3, 4 or 24 include amino acid sequences having at least 70% homology, preferably at least 80% homology, more preferably 90% homology, and yet more preferably 95%, most preferably 96%, 97%, 98% or 99% homology, with the amino acid sequence as shown in SEQ ID NO: 2, 3, 4 or 24, wherein the homology is calculated using BLAST (e.g., with the default or initial setting parameters of BLAST).

The SELF proteins of the present invention containing the EGF-like repeat motif can be obtained by culturing the aforesaid transformant and recovering the protein from the culture. The term "culture" means a culture supernatant, cultured non-bacterial cells or bacterial cells, or a cell debris of non-bacterial cells or bacterial cells.

The transformants of the present invention are cultured according to usual method for culturing a host.

When the transformants obtained from microorganisms such as E. Coli or yeast as the host are cultured, the culture medium may be natural culture medium or synthetic culture medium, as long as it contains carbon source, nitrogen source and mineral salts utilized by the microorganism and is useful for efficient culturing of the transformants.

Examples of carbon source are carbohydrates such as glucose, fructose, sucrose or starch, organic acids such as acetic acid or propionic acid, and alcohols such as ethanol or propanol.

Examples of nitrogen source are ammonia, and inorganic or organic ammonium salts such as ammonium chloride, ammonium sulfate, ammonium acetate and ammonium phosphate, and other nitrogen-containing compounds, as well as peptone, meat extracts and corn steep liquor.

Examples of mineral salts are monopotassium phosphate, dipotassium phosphate, magnesium phosphate, magnesium sulfate, sodium chloride, ferrous sulfate, manganese sulfate, copper sulfate and calcium carbonate.

The culturing is typically performed aerobically by e.g. shaking culture or aeration stirring culture at 37° C. The pH of the culture is adjusted with an inorganic or organic acid, or alkaline solution.

Antibiotics such as ampicillin or tetracycline may also be added to the culture medium, if necessary.

When microorganisms transformed with an expression vector using an inducible promoter are cultured, inducers may be added to the culture if necessary. For example, to culture a microorganism transformed by an expression vector using the Lac promoter, isopropyl-β-D-thiogalactopyrranoside (IPTG) may be added to the culture. Also, to culture an microorganism transformed by an expression vector using the trp promoter, indoleacetic acid (IAA) may be added to the culture.

When the transformant obtained from animal cells as host are cultured, the commonly-used RPMI1640 medium, DMEM medium, αMEM or the like, or these culture supplemented with fetal calf serum can be used as the culture medium.

The culturing is typically performed in the presence of 5% $CO_2$ at 37° C. for 1-30 days. During the culturing, antibiotics such as kanamycin or penicillin may be added to the culture if necessary.

After the culturing, when SELF protein of the present invention is produced intracellularly in bacterial cells or non-bacterial cells, the protein can be extracted by crushing the bacterial cells or non-bacterial cells. If the protein of the present invention is produced extracellularly by bacterial cells or non-bacterial cells, the culture solution itself may be used, or the bacterial cells or non-bacterial cells may be removed by centrifugation from the culture solution to be used. The protein according to the present invention can be isolated from the culture by subsequent protein isolation/purification process, for example, by using a conventional biochemical method for protein isolation and purification, such as ammonium sulfate precipitation, gel chromatography, ion exchange chromatography or affinity chromatography, alone or in combinations as appropriate.

3. Preparation of Antibodies

Antibodies specifically recognizing (or binding to) the protein of the present invention or fragments thereof can be produced as shown in Example 5 below. They can also be produced by the various methods shown in the printed books (see, e.g., "Antibodies: A Laboratory Manual", Cold Spring Harbor Laboratory Press). For example, antibodies recognizing SELF protein can be produced as follows: fully immunizing animals, such as mouse, guinea pig, rabbit and goat by inoculating SELF protein several times subcutaneously, intramuscularly, intraperitoneally or intravenously; drawing blood from the animal; and separating the serum from the blood. A suitable adjuvant can also be used in the immunization. Monoclonal antibodies can also be produced by well-known methods. For example, spleen cells from the mouse immunized with SELF protein are fused to mouse myeloma cells to produce hybridoma, and the monoclonal antibodies are prepared from a culture supernatant of the hybridoma, or a peritoneal fluid from a mouse which was administered intraperitoneally with the hybridoma. For use as an immunogen, SELF protein may be native proteins, recombinant proteins, or chemically synthesized proteins. Furthermore, proteins comprising the full amino acid sequence, peptide fragments having a partial structure of the protein, or fusion proteins of the protein and an additional protein, may also be used as the immunogen. The peptide fragment may be a fragment of the protein obtained by proteolysis with an appropriate protease, or a product expressed from a expression vector which incorporates whole or a part of the nucleotide sequence of SEQ ID NO: 1 or 23. The polypeptide fragment may be combined with a suitable carrier protein by chemical bonding and then may be used. The reactivities of the obtained antibodies can be determined by methods well known to those skilled in the art, such as enzyme immunoassay (EIA), radioimmunoassay (RIA), or Western blotting.

The antibodies produced as mentioned above can be applied to the purification, detection and measurement of the present protein, and can be used also as a diagnostic reagent for abnormal cell differentiation associated diseases. Example 6 shows that the antibody produced in Example 5 is used to determine where and on which developmental stages the present protein appears in mouse. As a result, the expression is observed on the fetal whole-mount at both the 9th day and 11th day in the limb buds and throughout the mesenchymal cells of the face, whereas in blood vessels at the 9th day, the expression is strongly observed in the arteria vitellina (omphalomesenteric membrane artery), and, although weakly, in the anterior cardinal veins of the head. It is weakly expressed in the heart on both embryonal days 9 and 11, and on the 9th day heart it is expressed only in the ventricle of heart, indicating that the present protein (the SELF protein) is expressed in the cardiac muscle. In the 11th embryonal day, it is found that the present protein is expressed in the internal epithelial layer of the intestine and outermost coat of the intestine.

4. Methods for Detecting Self Protein or Self Gene, and Detecting Reagents

SELF protein, antibodies against SELF protein and the gene encoding SELF protein (SELF gene) according to the invention, can be used for diagnosis of diseases associated with abnormal cell differentiation or the like.

In the present invention, the probe, which hybridize with the above nucleic acids to specifically recognize the nucleic acids, can be used as a detecting reagent for detection of the genes encoding SELF protein. The probes may be labeled with the commonly used radioactive isotopes (for example, $^{32}$P, $^{35}$S) or enzymes (for example, digoxygenin, fluorescein), etc., and may be specifically hybridized with the nucleic acids using the conventional blotting analysis or in situ hybridization, and thus may be detected.

Nucleic acids used as a probe in the present invention may be nucleic acids having at least part of the nucleotide sequence as shown in SEQ ID NO: 1 or 23. The length of the probe may be, but are not limited to, the full-length of the sequence of SEQ ID NO: 1, or more preferably 200-300 nucleotides in length.

Primers are also designed and synthesized based on the nucleic acid sequence of the present invention, the synthesized primers are used in gene amplification methods such as PCR, and thereby SELF gene can be detected.

The novel protein containing the EGF-like repeat motif of the present invention, SELF protein, can be detected using the antibodies against SELF protein. The detection may be made by immunological assay methods known in the art, such as EIA or RIA.

5. Activities of SELF Protein and SELF Gene, Pharmaceutical Composition Containing the Same, and Therapeutic and Preventive Method Using the Same The SELF protein of the present invention has a function of controlling the growth and differentiation of undifferentiated cells. The present invention also relates to a method for controlling the growth and differentiation of undifferentiated cells, comprising causing the SELF protein to come into contact with undifferentiated cells in vitro, ex vivo, or in vivo, for example. Undifferentiated cells herein may be any of the above-described undifferentiated cells. Preferable examples of such undifferentiated cells include: hematopoietic undifferentiated cells such as hematopoietic stem cells and hematopoietic progenitor cells; stem cells or progenitor cells contained in the bone marrow such as peripheral blood stem cells, myeloid stem cells, neural crest cells, neural stem cells, smooth muscle progenitor cells, and mesenchymal stem cells; and ES cells. These undifferentiated cells may be removed and obtained from subjects such as humans or non-human mammals.

The SELF protein has hematopoiesis-stimulating effects. In the present invention, that the SELF protein "has hematopoiesis-stimulating effects" means that, in the presence of the SELF protein, the number of blood cells generated from hematopoietic undifferentiated cells such as hematopoietic stem cells or hematopoietic progenitor cells or generated from cell populations (e.g., marrow cells) containing these undifferentiated cells, is increased by the effects. As described in Example 8, when stromal cells caused to over-express the SELF gene after introduction of the gene are cocultured with differentiation-antigen-negative bone marrow cells, the SELF protein secreted from stromal cells acts on the bone marrow cells, so as to promote the production of blood cells in the bone marrow cells. Furthermore, as described in Example 9, when bone marrow cells are cultured for a long time in the presence of the SELF protein, their capability for growth and differentiation is maintained for a time longer compared with a case of the culture in the absence of the SELF protein. Moreover, when bone marrow cells are cultured in the presence of the SELF protein, the amount of cell growth (or proliferation) is increased compared with a case of the culture in the absence of the SELF protein. Preferably, most blood cells produced in such bone marrow cells are neutrophils or macrophages. As described above, the SELF protein is capable of supporting the growth of hematopoietic progenitor cells in bone marrow cells.

Various hematopoietic factors such as G-CSF, GM-CSF, M-CSF, and EPO are used for treating hypocythemia. G-CSF is known to form neutrophil colonies in an in vitro colony formation test (Nicola et al., J. Biol. Chem., 258: 9017-9023, 1983). Furthermore, increases in neutrophils have been observed upon administration of G-CSF to mice (Tamura et al., Biochem. Biophys. Res. Commun., 142: 454-460, 1987). Furthermore, it has been shown that similar to the case of such an experiment conducted on mice, increases in neutrophils are also observed in a dose-dependent manner upon administration of G-CSF to humans (Asano et al., Behring Int. Mitt.

83: 222-228, 1988). For example, hematopoietic factors are clinically used and exert effects in: treatment of anaplastic anemia, myelodysplastic syndrome (MDS), or acute myeloid leukemia (AML); recovery of blood cell counts after cancer chemotherapy for non-Hodgkin's lymphoma, breast cancer, ovarian cancer, head and neck cancer, esophageal cancer, small cell lung cancer, urothelial carcinoma, non-small cell lung cancer, neuroblastoma, or the like; or recovery of blood cell counts after bone marrow transplantation performed for patients with acute leukemia, chronic myeloid leukemia, multiple myeloma, malignant lymphoma, anaplastic anemia, myelodysplastic syndrome, or the like (Ogawa, Blood, 81: 2844-2853, 1993; Sonoda et al., Stem Cells, 11: 543-554, 1993; Antin et al., Blood, 72: 707-713, 1988; Akio Urabe et al., Clinical Hematology (Rinsho Ketsueki), 34: 928-936, 1002-1010, 1993; Bessho et al., Br. J. Haematol. 80: 409-411, 1992; Hijiri Kitamura, hematopoietic factor 3: 64-70, 1990; Bessho et al., Stem Cells, 12: 604-615, 1994; Hoelzer et al., Behring Inst. Mitt., 83: 134-138, 1988; Shinpei Furusawa et al., Journal of Clinical and Experimental Medicine (Igaku no ayumi), 171: 851-855, 1994; Estey et al., J. Clin. Oncol. 12: 671-678, 1994; Kazumasa Ogawa, Journal of Clinical and Experimental Medicine (Igaku no ayumi), 171: 847-855, 1994; Tooru Masaoka, Journal of Clinical and Experimental Medicine (Igaku no ayumi), 171: 856-859, 1994). The SELF protein has hematopoiesis-stimulating effects, so that the protein is useful for treating and preventing the above hypocythemia in a manner similar to that in the case of hematopoietic factors.

In the present invention, hematopoiesis can be stimulated in a subject using the SELF protein or the SELF gene. According to the present invention, hypocythemia in a patient with anaplastic anemia, myelodysplastic syndrome, leukemia, or the like, and hypocythemia in a patient after cancer chemotherapy, bone marrow transplantation, or the like can be treated or prevented through administration of the SELF protein or a recombinant expression vector containing the SELF gene, preferably as a pharmaceutical composition containing the protein or the vector. The SELF protein or the SELF gene is preferable for treating leukemia and particularly preferable for treating acute myeloid leukemia. Furthermore, hematopoiesis can be stimulated and hypocythemia can be treated or prevented through administration of the SELF protein or the SELF gene to patients suffering from induced hypocythemia or patients who are expected to develop hypocythemia, after cancer chemotherapy against malignant tumors such as non-Hodgkin's lymphoma, breast cancer, ovarian cancer, head and neck cancer, esophageal cancer, small cell lung cancer, urothelial carcinoma, non-small cell lung cancer, or neuroblastoma, or following bone marrow transplantation therapy that is performed for treating acute leukemia, chronic myeloid leukemia, multiple myeloma, malignant lymphoma, anaplastic anemia, myelodysplastic syndrome, or the like. Moreover, the SELF protein or a recombinant expression vector containing the SELF gene can be administered to a patient, so as to increase peripheral blood stem cells. Thereafter, stem cells for stem cell transplantation can also be recovered from the peripheral blood. Preferably, such the SELF protein or recombinant expression vector containing the SELF gene is used by administering the vector into the bone marrow of a patient, for example.

The SELF protein or a recombinant expression vector containing the SELF gene is added to an in vitro coculture system of stromal cells and bone marrow cells to enhance the production of blood cells in the bone marrow cells. The thus obtained blood cells can also be administered to a patient. In this case, the bone marrow cells may be recovered from the relevant patient or another patient.

The SELF protein also has inhibiting effects on the growth and differentiation into smooth muscle cells from undifferentiated cells (inhibiting effects on the growth and differentiation of smooth muscle cells). The SELF protein can inhibit the growth and differentiation of any smooth muscle cells such as vascular smooth muscle cells, pericytes, gastrointestinal smooth muscle cells, bronchial smooth muscle cells, and urinary bladder smooth muscle cells, and preferably vascular smooth muscle cells. Examples of undifferentiated cells used herein include any undifferentiated cells. Such undifferentiated cells may be preferably hematopoietic stem cells, hematopoietic progenitor cells, myeloid stem cells, peripheral blood stem cells, neural crest cells, neural stem cells, mesenchymal stem cells, or smooth muscle progenitor cells. In the present invention, that the SELF protein has "inhibiting effects on the growth and differentiation of smooth muscle cells" means that under conditions where the growth and differentiation of smooth muscle cells can be induced and in the presence of the SELF protein, the number of smooth muscle cells does not increase or its level of increase decreases compared with a case in the absence of the SELF protein. In the present invention, according to the method of Takakura et al. (Takakura, N. et al., Immunity 9: 677-686, 1998), the para-aortic splanchnopleural mesoderms (P-Sp) of mouse fetuses were cocultured on a stromal cell line OP9 for 10 days in the presence of the SELF protein. When sheet-like structure (vascular bed) formation by vascular endothelial cells is observed but no vascular network formation takes place, it can be confirmed that the growth and differentiation of smooth muscle cells have been inhibited by the SELF protein.

Various diseases are known to be developed in association with elevated levels of the growth and differentiation of smooth muscle cells. For example, excessive growth of smooth muscle cells is observed in the case of glomerulonephritis. Furthermore, excessive growth of vascular smooth muscle cells causes blood vessel wall thickening or the stricture or occlusion of vascular lumina. Such excessive growth induces arteriosclerotic diseases such as atherosclerosis, diabetic vascular disorders, cerebral ischemic stroke, stenocardia, and cardiac infarction (Ross, R. et al., N. Engl. J. Med., 314, p. 488-500, 1986). It is thought that inhibition of the growth and differentiation of vascular smooth muscle cells leads to treatment and prevention of such arteriosclerotic diseases. Treatment for diseases that are associated with elevated levels of the growth and differentiation of smooth muscle cells, such as arteriosclerotic diseases, is under development, which comprises administration of an inhibitor for the growth and differentiation of smooth muscle cells to patients (Gordon, A et al., Science, 253, p. 1129, 1991).

Diseases associated with elevated levels of the growth and differentiation of smooth muscle cells (e.g., arteriosclerotic diseases or glomerulonephritis) can be treated or prevented by administering the SELF protein or a recombinant expression vector containing the SELF gene to a subject, preferably as a pharmaceutical composition containing such protein or vector, to inhibit the growth and differentiation of smooth muscle cells in the subject. For example, through administration of them to a subject with arteriosclerotic disease, the progression of arteriostenosis can be inhibited or its stenosis state can be alleviated.

Moreover, the SELF protein can inhibit angiogenesis through inhibition of the growth and differentiation of smooth muscle cells.

The vascular structures of mature blood vessels are stabilized through lining of vascular endothelial cells via matrices by parietal cells. Parietal cells surrounding vascular endothelial cells are composed of smooth muscle lineage cells such as smooth muscle cells and/or pericytes. Parietal cells function not only for supporting the vascular structure but also for vascular relaxation and contraction, for example. Parietal cells are desorbed from existing blood vessels when subjected to angiogenesis stimulation. Subsequently, bared vascular endothelial cells produce various proteases to digest vascular basement membranes or their surrounding extracellular matrices. Furthermore, the vascular endothelial cells grow and migrate to form a luminal structure. Parietal cells are then recruited to surround the vascular endothelial cells, so as to arrest the migration and the growth of the vascular endothelial cells. New vascular basement membranes are formed, and then mature blood vessels are constructed. Formation of new blood vessels based on such budding from existing blood vessels is generally referred to as angiogenesis.

Whereas angiogenesis is known to play an important role in endometrial formation, follicle formation, wound healing, and the like, abnormal angiogenesis is known to cause various pathological conditions. Folkman and Klagsbrun have proposed to generically designate diseases (a group of diseases) associated with abnormally elevated levels of vascular growth (e.g., malignant tumors, diabetic retinopathy, and psoriasis) as angiogenic diseases (Folkman & Klagsbrun, Science 235: 442-447, 1987). In particular, malignant tumors that are developed due to abnormal cell growth induce angiogenesis (tumor angiogenesis) at tumor-forming sites for supply of oxygen and nutrients, thereby causing tumor growth or metastasis. In recent years, therapeutic methods for angiogenic diseases using various angiogenesis inhibitors produce effects. Examples of angiogenesis inhibitors that have been reported to be useful as antitumor drugs include interferon, a vascular endothelial growth factor (VEGF) inhibitor (e.g., a neutralization antibody against VEGF), NK4, angiostatin, endostatin, and prolactin. For example, angiogenesis inhibitors targeting VEGF have been reported as follows. Inhibition of angiogenesis through administration of an anti-VEGF monoclonal antibody exerts tumor growth inhibitory effects (Kim et al., Nature 362, 841-844, 1993). Inhibition of angiogenesis through administration of an anti-VEGF monoclonal antibody can inhibit cancer metastasis (Melnyk et al., Cancer Research 56, 921-924, 1996). An effect of prolonging the survival time of a cancer patient can be obtained by the use of an anti-VEGF monoclonal antibody Bevacizumab (Avastin™; Genentech) in combination with anticancer agents (3 agents: irinotecan, 5-fluorouracil, and leucovorin) (Hurwitz et al., New Engl. J. Med. 350: 2335-2342, 2004). Tumor growth can be inhibited through inhibition of angiogenesis using an antisense DNA against a VEGF gene or small interfering RNA (siRNA) (Saleh et al., Cancer Research 56, 393-401, 1996). A vector expressing a soluble VEGF receptor protein (that binds to VEGF to inhibit VEGF activity) is introduced into a human ovarian cancer cell line RMG-1 and stably expressed therein, and then administration of the resulting RMG-1 cells to nude mice results in prolonged survival time of the nude mice and inhibited tumor growth in the nude mice, compared with control mice inoculated with an RMG-1 cell line expressing no soluble VEGF receptors (Hasumi et al., Cancer Res. 62: 2019-2031, 2002). When a chimeric protein comprising a soluble VEGF receptor and a human IgG1 constant region (Fc) is administered to nude mice into which a human ovarian cancer cell line OVCAR-3 has been transplanted, the chimeric protein binds to VEGF in a manner similar to that in the case of the soluble VEGF receptor, so as to inhibit the effects, and thereby the weights of tumors generated in vivo in mice are significantly lower than those in a control group to which a human IgG1 Fc alone has been administered (Byrne et al., Clin. Cancer Res. 9: 5721-5728, 2003). These reports show that gene therapy that involves introducing a vector capable of expressing a soluble VEGF receptor into cancer cells has therapeutic effects similar to those exerted by a therapeutic method that involves administering a soluble VEGF receptor protein to a subject. Furthermore, a low molecular weight compound SU5416 that is a tyrosine kinase inhibitor for a VEGF receptor has an effect of improving disease conditions against lung cancer, large bowel cancer, and Kaposi's sarcoma (Rosen et al., Proceedings of 35th ASCO, No. 618, 1999; Fong et al., Cancer Res. 59: 99-106, 1999). However, a case has also been reported wherein sufficient effects of inhibiting angiogenesis cannot be obtained by inhibition of the growth of vascular endothelial cells alone using such VEGF inhibitor.

In the present invention, the growth of vascular smooth muscle cells can be inhibited in a subject so as to inhibit angiogenesis through administration of the SELF protein or a recombinant expression vector containing the SELF gene to the subject. Furthermore, "angiogenesis" in the present invention means not only a process during which new blood vessels bud from existing blood vessels to generate mature blood vessels, but also a process during which mature blood vessels are generated through vasculogenesis that is initiated by undifferentiated cells. According to the present invention, by the use of the SELF protein or the SELF gene, tumor angiogenesis can be inhibited, so that tumor growth can be inhibited. Particularly, according to the present invention, angiogenic diseases in subjects can be treated or prevented by administering the SELF protein or a recombinant expression vector containing the SELF gene of the present invention to subjects, preferably as a pharmaceutical composition containing the protein or the vector. Target angiogenic disease may be any disease associated with abnormally elevated levels of angiogenesis and is not limited. Examples of such angiogenic diseases include malignant tumors such as solid tumors (including primary carcinoma and metastatic carcinoma) including renal cancer, breast cancer, brain tumor, gastrointestinal cancer, ovarian cancer, hepatic cancer, angioma, vascular fibrous tumor, and multiple myeloma; ophthalmic angiogenesis-related diseases such as diabetic retinopathy, retinopathy of prematurity, rubeosis iridis, sickle-cell retinopathy, central retinal vein occlusion, branch retinal vein occlusion, central retinal artery occlusion, age-related macular degeneration, and neovascular glaucoma; chronic inflammatory diseases such as rheumatoid arthritis; dermatologic angiogenesis-related diseases such as psoriasis (e.g., psoriasis vulgaris); diseases associated with abnormally elevated levels of vascular permeability such as ascites cancer, malignant pleural effusion, Crow-Fukase syndrome, and ovarian hyperstimulation syndrome; and ischemic diseases such as atherosclerosis, cerebral infarction, acute cardiac infarction, and peripheral artery occlusive disease. Through the above administration to subjects suffering from angiogenic diseases, the pathological conditions of angiogenic diseases can be improved. For example, tumor growth can be inhibited (that is, arrested or delayed) or tumor regeneration can be induced. Through the use of the SELF protein or a recombinant expression vector containing the SELF gene in combination with a VEGF inhibitor, therapeutic and preventive effects can also be enhanced in angiogenic diseases such as malignant tumors.

For the purpose of inhibiting angiogenesis or treating or preventing angiogenic diseases, the SELF protein or a recombinant expression vector containing the SELF gene may be systemically or topically administered to a subject. Preferably, such vector is administered topically to a site where angiogenesis is taking place or a site where angiogenesis is predicted to take place or to the periphery thereof. For example, it is preferable to directly inject the SELF protein or a recombinant expression vector containing the SELF gene into malignant tumors or to topically administer such protein or vector to the eyes of patients with ophthalmic angiogenesis-related diseases. Alternatively, such the SELF protein or recombinant expression vector containing the SELF gene is systemically administered such that the protein or the vector is delivered in a tissue specific manner to angiogenesis sites or organs containing such sites.

Blood vessel formation initiated by undifferentiated cells can also be inhibited by adding the SELF protein or a recombinant expression vector containing the SELF gene to an in vitro coculture system of stromal cells and undifferentiated cells (e.g., ES cells).

The dose of such the SELF protein or recombinant expression vector containing the SELF gene may differ depending on symptoms, age, and body weight of a subject, and the like. In the case of oral administration, the dose is generally between approximately 0.001 mg and several hundred mg per day. In this case, the protein or the vector is administered once or at several separate times. Furthermore, in the case of perenteral administration, the dose is generally between 0.001 mg and several hundred mg per administration via subcutaneous injection, intramuscular injection, or intravenous injection. In the case of gene therapy, more preferably, the dose is between 0.001 mg and several hundred mg per administration via subcutaneous injection, intramuscular injection, or intravenous injection at intervals of few days, several weeks, or several months.

In the present invention, through administration of the SELF protein or a recombinant expression vector containing the SELF gene in combination with a vascular endothelial growth factor (VEGF) inhibitor, higher inhibitory effects can be obtained against angiogenesis (e.g., tumor angiogenesis). As a result, for example, tumor growth and metastasis can be significantly inhibited.

Examples of such vascular endothelial growth factor (VEGF) inhibitor include, but are not limited to, antibodies such as a neutralization antibody against a vascular endothelial growth factor (VEGF), a neutralization antibody against EGF, a neutralization antibody against angiopoietin-2, Tie-2 antibody, and an antibody against a VEGF receptor; angiogenesis-related proteins such as a VEGF receptor, Tie-2, endostatin, angiostatin, chondromodulin (Hiraki et al., J. Biol. Chem., 272: 32419-32426, 1997), tenomodulin (Shukunami et al., Biochem. Biophys. Res. Commun. 280: 1323-1327, 2001), angiopoietin-2, thrombospondin, and interferon; and nucleic acids encoding such proteins. Moreover, a VEGF inhibitor may be an antisense oligonucleotide or a siRNA against a gene encoding VEGF, a VEGF receptor, FGF, a FGF receptor, angiopoietin-2, or Tie-2. A preferable example of a VEGF inhibitor is a vector mFlt-1-hIgG1 capable of expressing a Flt1-Fc protein that is a chimeric protein of a soluble VEGF receptor and a human IgG1 constant region (Fc) (Hirashima, M., et al., Blood 93: 1253-1263, 1999). In addition, a gene encoding VEGF has been identified in the case of a human (GenBank accession No. X51602), a mouse (GenBank accession No. NM_010228), a rat (GenBank accession No. NM_019306), and the like.

The SELF protein or a recombinant expression vector containing the SELF gene and a VEGF inhibitor may also be administered in mixed state, may be administered separately but simultaneously, or may be sequentially administered. More preferably, they are both directly administered to an angiogenesis site (e.g., tumor). The SELF protein or the recombinant expression vector containing the SELF gene, and the VEGF inhibitor, are more preferably administered at a dose ratio of 1:1, but the ratio is not limited thereto.

In the present invention, "subject" means a human or a non-human animal (e.g., a non-human mammal). Examples of such non-human animals include rodents (e.g., mice, rats, and hamsters), domestic animals (e.g., cattle, horses, and sheep), and companion animals (e.g., dogs and cats).

The present invention also provides a pharmaceutical composition containing an effective dose of the SELF protein or a recombinant expression vector that contains the SELF gene. The pharmaceutical composition of the present invention is useful for stimulating hematopoiesis in a subject, for inhibiting the growth and differentiation of smooth muscle cells, for inhibiting angiogenesis, and for obtaining antitumor effects. Such pharmaceutical composition containing a recombinant expression vector that contains the SELF gene can also be preferably used as a medicament for gene therapy. The pharmaceutical composition containing the recombinant expression vector that contains the SELF gene can also be used for ex vivo gene therapy according to a conventionally known method. A vector to be used for gene therapy in the present invention is preferably a vector that can be expressed in a host to be subjected to administration. For example, when a vector is administered to a human, a vector based on a plasmid, a virus, or the like, for which a mammalian cell is used as a host, is preferably used.

The pharmaceutical compositions of the present invention can be administered to patients in various forms. Examples of such administration forms include an oral administration of a tablet, capsule, granule, powder, syrup, etc., or a parenteral administration of an injection solution, ophthalmic solution, drop, suppository, etc. Such pharmaceutical compositions can be prepared by well-known methods. The pharmaceutical compositions may comprise a pharmaceutically acceptable carrier, diluent and excipient, as usually used in the pharmaceutical industry. For example, lactose or magnesium stearate may be used as the carrier or excipient for tablets. The injection solution is prepared using the solution wherein the SELF or its salt is dissolved, suspended or emulsified in a sterile aqueous or oily solution commonly used for injection. The aqueous solution used for injection solution may be an isotonic solution containing physiological saline, glucose or other auxiliaries, and can be used in combination with a suitable solubilizing agent, e.g., an alcohol or polyalcohol such as propylene glycol, a nonionic surfactant, etc. The oily solution may be sesame oil, soybean oil, etc., and can be used in combination with a solubilizing agent, e.g., benzyl benzoate or benzyl alcohol, etc.

The present invention also relates to a pharmaceutical kit for angiogenesis inhibition or tumor growth inhibition, which contains the SELF protein or a recombinant expression vector containing the SELF gene and a vascular endothelial growth factor inhibitor in combination. Such pharmaceutical kit contains each of these agents in a single dosage unit or in multiple dosage units. The pharmaceutical kit may also contain a syringe, medication instructions, and the like.

6. SELF Promoter

A SELF promoter region of the present invention comprises the nucleotide sequence as shown in SEQ ID NO: 31. "SELF promoter" or "SELF promoter region" in the present invention means a region that substantially affects the transcription of the SELF gene. SELF promoter may contain transcriptional regulatory sequences such as an enhancer and silencer in addition to a region having promoter activity. Furthermore, "promoter activity" means ability of transcription from a gene into mRNA.

As shown by comparison of the SELF promoter sequence shown in SEQ ID NO: 31 with a SELF cDNA sequence shown in SEQ ID NO: 1, the transcription initiation position is at nucleotide 3487 of SEQ ID NO: 31. Furthermore, the portion between nucleotides 3632 and 3848 of SEQ ID NO: 31 is the 5' terminal portion of a structural gene of the SELF protein. The 1st intron begins from nucleotide 3849 of SEQ ID NO: 31.

A region having basic promoter activity of the SELF gene is the CpG island region between nucleotides 3299 and 3487 in the nucleotide sequence shown in SEQ ID NO: 31. Hence, any fragment of the nucleotide sequence as shown in SEQ ID NO: 31 that contains the nucleotide sequence of nucleotides 3299 to 3487 has SELF promoter activity. For example, DNA consisting of the nucleotide sequence of nucleotides 2360 to 3487 of SEQ ID NO: 31 or DNA consisting of the nucleotide sequence of nucleotides 3374 to 3487 of SEQ ID NO: 31 has SELF promoter activity.

In particular, the region exerting the highest promoter activity is the nucleotide sequence of nucleotides 2796 to 3487 of SEQ ID NO: 31. Therefore, the SELF promoter of the present invention preferably contains at least the region of nucleotides 2796 to 3487 as shown in SEQ ID NO: 31.

Several transcriptional regulatory sequences (sequences to which transcription controlling factors can bind) are present in such SELF promoter region as shown in SEQ ID NO: 31. Specifically, a C/EBPβ (CCAAT/Enhancer Binding Protein β) binding sequence is present between nucleotides 1590 and 1603, between nucleotides 2402 and 2415, between nucleotides 2456 and 2469, or between nucleotides 2744 and 2757 of SEQ ID NO: 31. A sequence containing a NF-kappaB binding sequence is present between nucleotides 8 and 17, between nucleotides 830 and 839, or between nucleotides 2581 and 2590 of SEQ ID NO: 31. A MyoD (myoblast determining factor) binding sequence is present between nucleotides 92 and 101, between nucleotides 727 and 736, between nucleotides 810 and 819, between nucleotides 1053 and 1062, between nucleotides 2047 and 2056, between nucleotides 2509 and 2518, or between nucleotides 2831 and 2840 of SEQ ID NO: 31. An AML-1a (runt-factor AML-1) binding sequence is present between nucleotides 411 and 416, between nucleotides 437 and 442, between nucleotides 971 and 976, between nucleotides 1606 and 1611, between nucleotides 1881 and 1886, between nucleotides 2233 and 2238, between nucleotides 2317 and 2322, or between nucleotides 3002 and 3007 of SEQ ID NO: 31. An Oct-1 (octamer binding factor 1) binding sequence is present between nucleotides 2472 and 2488 or between nucleotides 3052 and 3065 of SEQ ID NO: 31. More preferably the SELF promoter of the present invention contains at least one of such transcriptional regulatory sequences in addition to the above highly active promoter region.

Other examples of the SELF promoter of the present invention include the nucleotide sequence of nucleotides 2355 to 3487 of SEQ ID NO: 31, the nucleotide sequence of nucleotides 2795 to 3487 of SEQ ID NO: 31, the nucleotide sequence of nucleotides 3298 to 3487 of SEQ ID NO: 31, and the nucleotide sequence of nucleotides 3370 to 3487 of SEQ ID NO: 31.

Examples of the SELF promoter of the present invention are not limited to the DNA comprising the nucleotide sequence as shown in SEQ ID NO: 31 or a fragment thereof. Examples of the SELF promoter of the present invention also include DNAs that hybridize to the aforementioned DNAs under stringent conditions, as long as they have promoter activity. Here, the stringent conditions mean conditions wherein identification is possible through hybridization reaction at 68° C. in the presence of 0.7 M to 1.0 M NaCl using a DNA-immobilized filter and then washing at 68° C. using 0.1× to 2×SSC solution (1×SSC contains 150 mM NaCl and 15 mM sodium citrate). Such conditions may be any conditions, as long as substantially the same results can be obtained with such conditions.

Furthermore, examples of the SELF promoter of the present invention also include a DNA comprising a nucleotide sequence that has 70% or more, preferably 80% or more, more preferably 90% or more, and particularly preferably 95% or more, 96% or more, 97% or more, 98% or more, or 99% or more homology with the DNA comprising the nucleotide sequence as shown in SEQ ID NO: 31 or a fragment thereof when calculated using BLAST or the like (for example, with BLAST default (or initial) parameters), as long as it has promoter activity.

However, it is desired that the nucleotide sequences corresponding to the regions having basic promoter activities within the nucleotide sequence shown in SEQ ID NO: 31, (the nucleotide sequence of nucleotides 3374 to 3487, preferably of nucleotides 3299 to 3487, and more preferably of nucleotides 2796 to 3487 of SEQ ID NO: 31) or the above-mentioned transcriptional regulatory sequences are conserved without mutation.

The origin of the SELF promoter of the present invention is not particularly limited, as long as it satisfies the above requirements. The SELF promoter may be derived from a human, a mouse, or from other mammals.

The SELF promoter of the present invention can be obtained as follows, for example. Specifically, an appropriate genomic library is screened by a known method using a SELF DNA portion as a probe, and then a clone hybridizing to the probe is obtained. A DNA fragment containing a sequence upstream from the translation initiation codon of the SELF gene is excised from the obtained clone with a restriction enzyme, and then cloned into an appropriate vector. The cloned DNA fragment is sequenced to verify that the determined sequence is of the SELF promoter. Furthermore, motif search is performed for the thus obtained SELF promoter sequence, so that its transcriptional regulatory sequence (binding site of a transcription controlling factor) can be found.

The present invention also provides a recombinant vector containing the SELF promoter. Such recombinant vector containing the SELF promoter may also contain a foreign structural gene being operably linked thereto under expression control of the SELF promoter.

Such foreign structural gene may also be a reporter gene for examining SELF promoter activity. Examples of a reporter gene include, but are not limited to, a luciferase gene, a chloramphenicol acetyltransferase gene, an alkaline phosphatase gene, a green fluorescent protein (GFP), and a β-galactosidase gene. When such recombinant vector containing the SELF promoter is used for producing conditional gene targeting mice, a Cre recombinase gene may also be ligated as such a foreign structural gene.

Examples of a vector for insertion of the SELF promoter are not particularly limited, as long as such vector is replicable in a host. Specifically, any vectors described above in this specification can be used.

Furthermore, the present invention also provides cells transformed with recombinant vectors containing the SELF promoter of the present invention.

As hosts for transformation using the above recombinant vectors, bacteria of the genus *Escherichia*, bacteria of the genus *Bacillus*, yeast, insect cells, insects, and animal cells, for example, as described above in this specification are used. The SELF promoter of the present invention can be derived from an animal. Thus, it is desirable to use an animal cell as a host in order to examine the promoter functions. Examples of animal cells that are used herein include monkey cells COS-1, COS-7, Vero, and CV-1, Chinese hamster cells CHO (hereinafter abbreviated as CHO cells), dhfr gene-deficient CHO cells, mouse L cells, mouse AtT-20, mouse myeloma cells, mouse lymphoma cells EL4, rat GH3, rat pheochromocytoma-derived cells PC12, mouse fibroblasts NIH3T3 and 10T1/2, mouse myoblasts C2C12, mouse stromal cells PA6, ST2, and OP9, human megakaryoblasts CMK, human T cells Jurkat, human renal epithelial cells 293, human hepatoma cells HepG2, human osteosarcoma cells MG-63, human FL cells, white adipose cells, ovum, ES cells, and differentiation-induced cells obtained under appropriate differentiation conditions. In the process for DNA transfer into animal individuals, ovum or ES cells (Nature, 292: 154, 1981) can also be used. As methods used for transformation of these cells, a lipofection method (Focus, 21: 54, 1999), a calcium phosphate method (Virology, 52: 456, 1973), an electroporation method (Molecular Cloning, 3rd. Ed. 16. 33-16. 36, Cold Spring Harbor Laboratory, New York, 2001)), a microinjection method, and the like are used.

7. Screening Using SELF Promoter

A substance that promotes or inhibits SELF promoter activity, such as a compound or a salt thereof that promotes or inhibits cell growth and cell differentiation, can be screened for by the use of transformed cells wherein a recombinant vector containing the SELF promoter of the present invention has been introduced. For example, with the use of the SELF promoter activity of the present invention as an indicator, therapeutic agents for various diseases that are caused by abnormal expression of the SELF gene (overexpression or underexpression of the SELF gene) can also be screened for. Such screening method and screening kit will be described specifically as follows.

(1) Screening Method for a Substance that Promotes or Inhibits Self Promoter Activity An example of a method for screening for a substance that promotes or inhibits the SELF promoter activity of the present invention involves causing a test substance to come into contact with the transformed cells of the present invention wherein a recombinant vector that has a polypeptide-encoding gene (foreign structural gene) inserted therein under control of the SELF promoter has been introduced, measuring the amount of the polypeptide expressed by the gene, and comparing the measured amount with that in the case of causing the same test substance to come into contact with transformed cells wherein the same vector not containing any SELF promoter of the present invention has been introduced. Examples of such test substances include, in addition to peptides, proteins, sugars, organic compounds, inorganic compounds, and salts thereof, fermentation products, plant extracts, and animal tissue extracts. Furthermore, such substances may be either novel or known substances. The above polypeptide-encoding gene may be any structural gene, as long as its gene product is detectable, and it is preferably a reporter gene. An example of a method for measuring the expression amount of a polypeptide is a method for measuring luciferase activity based on a method according to Brasier, A. R. et al. (Biotechniques vol. 7, 1116-112, 1989).

(2) Screening Kit for Use in Screening for a Substance that Promotes or Inhibits Self Promoter Activity A screening kit of the present invention contains a transformed cell wherein the recombinant vector that contains the SELF promoter of the present invention and preferably a polypeptide-encoding gene placed under control of the SELF promoter has been introduced. The screening kit of the present invention may further contain other screening reagents. An example of the screening kit of the present invention is as follows.

An example of the screening kit
Screening reagents contained in the kit:
1. Cell culture medium: Dulbbecco's modified Eagle's MEM (D-MEM; Invitrogen) supplemented with 15% fetal calf serum (Invitrogen).
2. Plasmid for measuring SELF promoter activity: pGL3-basic plasmid DNA (Promega) wherein a structural gene (e.g., a luciferase gene) ligated downstream of the SELF promoter of the present invention has been inserted.
3. Host cells: Mouse myoblasts C2C12 (RIKEN Cell Bank).
4. Test substance: A test substance in an aqueous solution state is stored at 4° C. or −20° C. When it is used, the test substance is diluted at a concentration of 1 µM using the cell culture medium. Test substances that are slightly soluble in water are dissolved in dimethylformamide (DMSO), methanol, or the like.
5. Luminescent reagent (Promega).
Screening can be appropriately performed using the kit according to description in Example 17, for example.

8. Other Uses of Vector Containing Self Promoter

The SELF gene is expressed in mesenchymal cells, so that the SELF promoter can cause expression specific to mesenchymal cells. Therefore, through insertion of an any foreign gene under control of the SELF promoter of the present invention, a vector can be provided that causes the expression of the foreign gene specifically in mesenchymal cells of bone and cartilage-generating tissues, blood vessels, cardiac muscle, and the like. Specifically, a vector containing the SELF promoter can be used as a vector for gene therapy for bone diseases, chondropathy, vascular diseases, and cardiac muscle diseases.

Here, "mesenchymal cells" means cells that can be differentiated from mesenchymal stem cells. Mesenchymal stem cells are cells of mesodermal lineage and are capable of differentiating into bone, cartilage, skeletal muscles, cardiac muscles, tendons, adipose cells, bone marrow stroma, blood vessels, ectodermal nerve, and endodermal liver cells (Science, 284: 143, 1999; Nature, 418: 41, 2002). For example, it is known that mesenchymal stem cells existing in the bone marrow differentiate into osteoblasts, chondrocytes, adipose cells, muscle cells, ligament cells, and the like.

The above diseases subjected to gene therapy are not particularly limited. For example, the above vectors are effective for treating blood diseases such as anaplastic anemia or pancytopenia after cancer chemotherapy or bone marrow transplantation.

Furthermore, the present invention also relates to transgenic non-human animals wherein the recombinant vector containing the SELF promoter has been introduced. For example, mice subjected to conditional gene targeting can be produced by using a vector containing a Cre recombinase gene under control of the SELF promoter, wherein a target gene has been disrupted specifically in mesenchymal cells. Specifically, a targeting vector containing a gene fragment (to be deleted) flanked by two loxP sequences is constructed. The vector is then introduced into mouse ES cells to cause homologous recombination. Chimeric mice are produced using the ES cells. In the chimeric mice, although the gene region to be deleted in the genome is flanked by the loxP sequences, the gene functions normally and the phenotype is the same as that in a normal mouse. The chimeric mice are crossed with transgenic mice wherein a recombinant vector containing a Cre recombinase gene under control of the SELF promoter has been introduced. In the thus obtained progeny mice, Cre recombinase is expressed depending on the expression of the SELF promoter, so that the gene flanked by the loxP sequences is disrupted specifically in mesenchymal cells.

Furthermore, the vector containing the SELF promoter of the present invention exerts strong promoter activity in mesenchymal cells. Thus, such vector can also be used as an expression vector for protein production in animals or cultured cells. Through insertion of a viral enhancer such as SV40, CMV, HTLV, MLV, or MSV in the vicinity of such promoter, a vector having promoter activity that is even higher than that of such SELF promoter alone can also be constructed. Examples of such vector include a vector prepared by inserting an SV40-derived 72 basepairs repeat (Nucleic Acids Res. 9: 6069, 1981) upstream of the SELF promoter of nucleotides 3298 to 3487 of SEQ ID NO: 31, and a vector prepared by inserting a CMV enhancer upstream of the SELF promoter of nucleotides 3298 to 3487 of SEQ ID NO: 31. The CMV enhancer can be isolated according to the method of Isomura et al. (J. Virol. 77: 3602, 2003).

EXAMPLES

The specific examples of carrying out the invention are provided below. However, the present invention is not limited to these examples.

Example 1

Cloning of a Gene Containing a Novel EGF-Like Repeat Sequence

The amino acid sequences of the EGF-like motif found in Notch and Delta protein were searched, and it was ascertained that sequences CPPGF and NGGTC appeared in the EGF-like motif sequences of these proteins with a relatively high frequency. Special degenerate primers, EGFLM-s and EGLM-as, were designed based on this amino acid sequences. An EcoRI site was introduced at the 5' terminal end of EGFLM-s, and a BamHI site was introduced at the 5' terminal end of EGLFM-as. These sequences were shown as follows:

EGFLM-s: GAATTCTGYCCNCCNGGNTTYT (SEQ ID NO: 5)

EGFLM-as: GGATCCRCANGTNCCNCCRTT (SEQ ID NO: 6)

R=A or G Y=C or T N=G, A, T or C

Using these primers, RT-PCR (reverse transcription PCR) was performed on mRNAs of the mouse stromal cell PA6 (Kodama et al., J. Cell. Physiol. 112, 89-95, 1982) as templates, as follows.

mRNAs of mouse PA6 were prepared using the mRNA separation kit from Pharmacia according to the attached instructions. The synthesis of cDNA was performed using GIBCO-Lifetech-BRL SuperScript™ II reverse transcriptase according to the attached instructions. Using the synthesized cDNA (0.5 µg) as a template, 5 µl of 10× buffer (500 mM KCl, 100 mM Tris-HCl (pH 8.3), 15 mM $MgCl_2$, 0.01% gelatin), 4 µl of 2.5 mM dNTP mixture (Pharmacia), and 1 µl respectively of the above-mentioned 40 µM primers EGFLM-s, EGFLM-as were added, and then deionized water was added to give a total volume of 494 $L^1$. Next, 1 µl of Taq DNA polymerase (TOYOBO, 5 U/µl) was added, and RCR reaction was performed for 35 cycles of 1 minute at 94° C., 2 minutes at 48° C. and 3 minutes at 72° C., and completed at 4° C. When an aliquot of the resulting PCR product was subjected to electrophoresis in an agarose gel, multiple amplification products of approx. 0.2 kb, approx. 0.35 kb and approx. 0.6 kb were observed. Then, this PCR product (2 µl) was ligated into pCR™ II (Invitrogen) with T4 DNA ligase. *Escherichia coli* was transformed with this ligated product according to the usual method, and then plasmid DNA was prepared from the resulting transformant.

Next, this plasmid DNA was digested with the restriction enzyme EcoRI, and a clone incorporating the cDNA was selected based on analysis by agarose electrophoresis.

When the nucleotide sequences of cDNAs in 200 selected clones were determined, among them 50 clones were found to be genes encoding an EGF-like motif. Specifically, they included 30 clones of dlk, 11 clones of Delta-1, 8 clones of Jagged-2 and one clone of the novel gene. This novel gene was named E13. The nucleotide sequence of E13 corresponds to nucleotides 1624 to 2172 of SEQ ID NO: 1 in the sequence listing, and the amino acid sequence deduced from this sequence of E13 corresponds to amino acids 490 to 672 of SEQ ID NO: 2. It was found that the DNA fragment of this gene encodes three EGF-like motifs.

Example 2

Cloning of Full Length E13 cDNA

It is known that RACE (Rapid Amplification of cDNA Ends) method can be used in cloning a full length cDNA.

A Marathon™ cDNA Amplification kit (Clontech) was used to clone the full length cDNA of the gene cloned in Example 1. Unless otherwise specified, experiments were performed according to the manual of this kit.

For the purpose of cloning the 5' terminal end and the 3' terminal end of the E13 gene, E13 specific primers, E13-GSP-1as and E13-GSP-2s were designed based on the sequence of the E13 cDNA cloned in Example 1. The sequences were shown as follows:

E13-GSP-las: AGTGCCGTCCAGAGAATCCTGG (SEQ ID NO: 7)

E13-GSP-2s: GGAGGCACATGCAAGGAAATGGGC-GACG (SEQ ID NO: 8)

The cDNAs synthesized from mouse PA6 mRNAs were ligated to the Marathon™ cDNA adapter in the kit according to this kit manual.

Next, on the 5' end side, PCR was performed using the gene specific primer E13-GSP-1as and the adapter primer AP1 attached to the kit (referred to as 5'RACE), while on the 3' end side, PCR was performed using a gene specific primer E13-GSP-2s and AP1 (referred to as 3'RACE). Each of the resulting PCR products was ligated into pT-Adv (Clontech) with T4 DNA ligase. *Escherichia coli* was transformed with the ligated product. The transformants were replica plated and they were transferred from a replica plate onto Wattmann 541. Using the usual method, colony hybridization was performed on it with the $^{32}$P-labeled E13 gene (DNA fragment obtained in Example 1). Plasmid DNA was prepared from a positive clone. The insertion of the DNA fragment into the plasmid was confirmed by digesting with EcoRI. The nucleotide sequence of the cDNA was determined using the BigDye™ Terminator Cycle Sequencing kit on PRIZM® 377XL of Applied Biosystems.

Sequencing of the DNA fragment of approx. 3.4 kb inserted into clone 5C obtained in 3'RACE reveals the sequence from nucleotide 1930 to 5245 of SEQ ID NO: 1 in the sequence listing. Also, Sequencing of the DNA fragment of approx. 1.4 kb inserted into clone 8N obtained in 5'RACE reveals the sequence from nucleotide 703 to 2127 in SEQ ID NO: 1.

For the purpose of cloning the further 5' upstream sequence, a primer DNA E13-R1718 complementary to E13 mRNA was synthesized, and the cDNA was synthesized using the primer. E13-R1718 was shown as follows.

E13-R1718: GACATACTTTGTTGTCACACGAAGATTG-GCCCGATTCACAGG (SEQ ID NO: 9).

The cDNA was synthesized from 1 μg of PA6 mRNAs using a Lifetech kit. First, 1 μg PA6 mRNAs were dissolved in 4 μl of distilled water, and 1 μl of 2 μM E-13R1718 primer was added. Next, the solution was heated for 2 minutes at 70° C., and then cooled for 2 minutes on ice. 2 μl of 5× first strand reaction buffer, 1 μl of 0.1M DTT solution, 1 μl of 10 mM dNTP mixture and 1 μl of SuperScript™ II reverse transcriptase were added, and the reaction was incubated at 45° C. for 1 hour, and at 55° C. for 30 minutes.

48.4 μl of distilled water, 16 μl of 5× second strand reaction buffer, 1.6 μl of 10 mM dNTP mixture and 4 μl of 20× second strand enzyme mixture were added to the above-mentioned first strand reaction buffer, and made to react at 16° C. for 1.5 hours. Next, 2 μl of 5 U/μl of T4 DNA polymerase was added, and reacted at 16° C. for 45 minutes. 4 μl of EDTA/glycogen mixture was added to stop the reaction, 100 μl of phenol/chloroform (1:1) was added, and stirred vigorously, and then the mixture was centrifuged at 14000 rpm for 10 minutes and the aqueous phase was collected. 100 μl of phenol/chloroform (1:1) was again added to the aqueous phase, and then the mixture was centrifuged at 14000 rpm for 10 minutes and the aqueous phase collected. ½ volume of 4M ammonium acetate solution and 2.5 volumes of ethanol were added to this, and after stirring, centrifuged at 14000 rpm for 20 minutes. After the precipitate was washed with 80% ethanol solution, the precipitate was air-dried, and dissolved in 100 μl of distilled water to obtain a cDNA solution.

1 μl of 10 μM Marathon™ cDNA adaptor (Clontech) solution, 2 μl of 5× ligation solution, 1 μl of 400 U/μl T4 DNA ligase and 1 μl of distilled water were added to 5 μl of the above cDNA solution, made to react at 16° C. for 18 hours, and heated at 70° C. for 5 minutes. The resulting cDNA synthesized using the E13 specific primer as so mentioned above was stored at −20° C. until used. The 5'RACE method using this cDNA, was performed by using the Clontech Marathon™ cDNA amplification kit. The method is shown below.

E13 specific primer E13-1718as was synthesized. The sequence was shown as follows.

E13 specific primer E13-1718as: CACACGAAGATTGGC-CCGATTCACAGG (SEQ ID NO: 10)

5 μl of cDNA synthesized was E13 specific primer as described above diluted 50 times in Trisin EDTA buffer, 1 μl of 10 μM E13 specific primer E13-1718as, 1 μl of 10 μM AP-1 primer, 10 μl of 5×GC2 PCR reaction buffer, 5 μl of GC-Melt, 5 μl of 2 μM dNTP mixed solution, 22 μl of distilled water and 1 μl of 50× Advantage G2 polymerase, were mixed to give a total volume of 50 μl.

The PCR reaction was performed using the following protocols: heating at 94° C. for 5 seconds, 5 cycles of 5 sec at 94° C., 10 min at 72° C.; 5 cycles of 5 sec at 94° C., 10 min at 70° C.; and 25 cycles of 5 sec at 94° C., 10 min at 68° C.; and then completed at 4° C. When 5 μl of the PCR product was subjected to electrophoresis on an agarose gel, an amplification products were observed as several smear bands ranging approx. 3.5 kb to approx. 0.6 kb). The appearance of smear bands indicates the occurrence of nonspecific amplifications. Thus using this amplification product as the template, Nested PCR was performed.

First, a primer E13-GSP-3as for Nested PCR was synthesized. The sequence was as follows.

E13-GSP-3as: GCACTTGCCACCATTGAGGCATGGACG (SEQ ID NO: 11).

Next, 5 μl of the aforesaid amplification product diluted 250 times in Trisin EDTA buffer solution, 1 μl of 10 μM E13 specific Nested PCR primer E13-GSP-3as, 1 μl of 10 mM AP-2 primer (Clontech), 10 μl of 5×GC2PCR reaction buffer, 10 μl of GC-Melt, 5 μl of 2 μM dNTP mixture, 17 μl of distilled water and 1 μl of 50× Advantage G2 polymerase (Clontech), were mixed to give a total volume of 50 μl.

The PCR reaction was performed using the following protocols: heating at 94° C. for 5 seconds, 5 cycles of 5 sec at 94° C., 10 min at 72° C.; 5 cycles of 5 sec at 94° C., 10 min at 70° C.; and 25 cycles of 5 sec at 94° C., 10 min at 68° C.; and then completed at 4° C.

When 5 μl of the PCR product was subjected to electrophoresis on an agarose gel, an amplification product was observed as a band of approx. 0.9 kb. The resulting PCR product was ligated into pT-Adv (Clontech) with T4 DNA ligase. *Escherichia coli* was transformed with this ligated product. Plasmid DNA was prepared from the obtained transformant. Plasmid DNA was digested with the restriction enzyme EcoRI, and a plasmid clone incorporating approx. 0.9 kb cDNA was selected based on analysis by agarose electrophoresis. The nucleotide sequence of approx. 0.9 kb cDNA inserted into the clone ES14, which is one of the selected clones, was determined using the BigDye™ Terminator Cycle Sequencing kit using PRIZM® 377XL from Applied Biosystems. Sequencing of the nucleotide sequence reveals the sequence from nucleotide 1 to 951 of SEQ ID NO: 1 in the sequence listing, was clarified.

When the nucleotide sequences obtained from the above experiment were analyzed for an open reading frame (gene's reading frame) of this cDNA by the genetic information processing software GENETY-WIN (Version 5, Software Development Co.), the translation start methionine may be positioned on nucleotide 157 of SEQ ID NO: 1, and the stop codon may be positioned on nucleotide 4365. The amino acid sequence deduced from this genetic sequence is shown by SEQ ID NO: 2 in the sequence listing. This genetic sequence was analyzed with gene analysis software, and it was predicted that amino acids 1 to 22 of SEQ ID NO: 2 corresponds to a signal sequence, and thereby the number of residues in the amino acid sequence corresponding to the structural gene was 1381, and the estimated molecular weight was 149,400. The amino acid sequence corresponding to the structural gene is shown by SEQ ID NO: 3 in the sequence listing.

This gene was named stromal cell-derived EGF-like repeat containing factor, and it was abbreviated as SELF.

Example 3

Isolation/Identification of SELF cDNA from Mouse Stromal Cell PA6 Using PCR and Construction of an Expression Vector Primers E13F-S1 and E13F-AS1 were synthesized based on the sequence (SEQ ID NO: 1) obtained according to Example 2. The sequences were shown below.

E13F-S1: CAGATCCCGGCGATGCGCCTC (SEQ ID NO: 12)

E13F-AS1: AGGGAATTCTGGAACCTTCCT (SEQ ID NO: 13).

Using single-strand cDNA from PA6 prepared in Example 1 as a template, PCR was performed by GC2 polymerase (Clontech) with the primers E13F-S1 and E13F-AS1. As a result, a DNA fragment of 4399 base pairs (bp) which is a SELF cDNA fragment having whole the sequence information of SELF protein, was obtained.

This DNA fragment was blunted with T4 DNA polymerase, and was further digested with EcoRI. After purification by agarose gel electrophoresis, a EcoRI digested DNA fragment was cloned between EcoRI and EcoRV sites of a pCR™ II vector, and a clone pCR-mSELF was thus obtained. The cDNA in this clone was sequenced using the BigDye™ Terminator Cycle Sequencing kit using PRIZM® 377XL of Applied Biosystems. As a result, the sequence coincided with nucleotides 145 to 4543 of SEQ ID NO: 1.

The PCR-mSELF was digested with XbaI, and then was blunted with T4 DNA polymerase, and further digested with EcoRI to obtain a SELF cDNA fragment. The cDNA fragment was introduced between NheI site (previously blunted) and EcoRI site, which was used for DNA insertion, of the expression vector pCI-neo (Promega) for mammal cell lines. The resulting vector was named pCI-neo-mSELF.

As shown in this example, once the nucleotide sequence information of SEQ ID NO: 1 was produced, it is easy for those skilled in the art to synthesize all or any part of the SELF cDNA by using any SELF expressing cells (for example, stromal cell PA6), to determine its nucleotide sequence, clone it into any expression vector, and to obtain a homolog other than the mouse homolog using hybridization techniques.

Example 4

Expression of SELF Gene

In order to analyze the expression pattern of SELF, RNA was prepared from various mouse tissues and cell lines. After preparing total RNA, Poly A RNA was separated using oligo dT cellulose (NEB). Next, 2 µg of this poly A-containing RNA was subjected to electrophoresis in formalin agarose gel, and then RNA was transferred to a nylon membrane. In some experiments, pre-prepared Multiple tissue Northern Blot (Clontech) was used. Also, pCR2-E13 into which the SELF gene fragment had been cloned, prepared in Example 1, was digested with EcoRI, and subjected to agarose gel electrophoresis, and the SELF gene fragment of approx. 560 bp was purified. The SELF gene fragment was radiolabeled with $^{32}$P using a Nick Translation Kit (Amersham Pharmacia) to prepare a probe. Northern Blot was performed using this probe according to the usual method. Hybridization was performed under stringent conditions (0.5M sodium phosphate, pH 7.2, 7% SDS, 1 mM EDTA, 68° C.). After washing three times at 50° C. with 0.1×SSC containing 0.1% SDS, an autoradiogram was prepared.

As a result, in mouse tissues, SELF was expressed in the brain, heart and testes, whereas it was not expressed in the spleen, lungs, liver, muscles, kidney or bone marrow. In mouse culture cells, it was expressed in PA6, ST2, OP9, 10T1/2, NIH3T3, MC3T3E1, which are mesenchymal tissue cells, whereas it was not expressed in myeloblast cell lines (FDC-P2, NFS-60), mast cell lines (P815, BNu-1), macrophage cell lines (WEHI-3, BABT9I, J774.1), T cell lines (SPB24, GRSL), and cultured hepatocytes. Among mesenchymal cells, HeslKOST did not express it.

The results are shown in FIG. 1. FIG. 1 shows that mouse SELF gene was expressed in osteoblast strain MC3T3E1 (see, lanes 3 to 5). Further, the SFLF gene expression was enhanced by long-term culturing of osteoblasts, in particular osteoblast strain MC3T3E1, and incubating calcification or stimulating the osteoblasts with TGF-β (lanes 4 and 5), suggesting that SELF is a molecule which participates in osteogenesis or affects osteoclasts to control their functions of osteoclasts.

Figure 2:
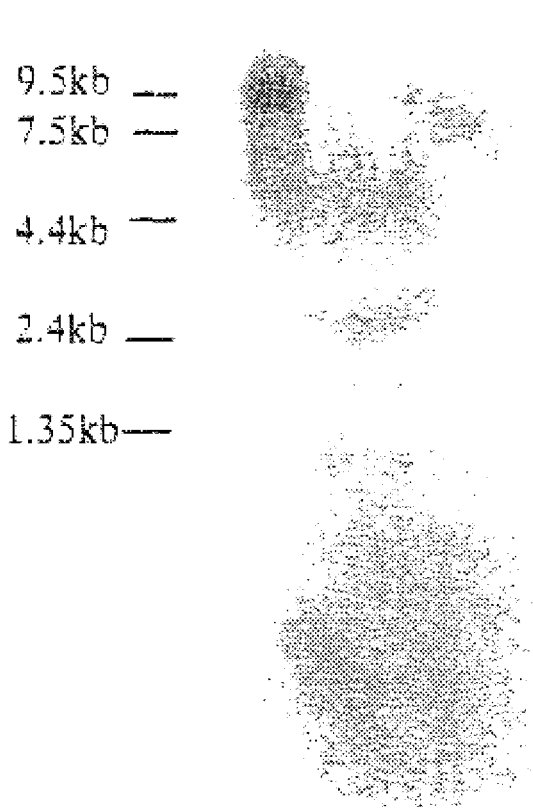
FIG. 2 is a photograph showing the expression of SELF mRNA in mouse fetuses. The expression of the SELF gene was examined for mouse fetuses by Northern blot analysis using a SELF cDNA fragment. Lane 1: marker; Lane 2: fetus on day 7; Lane 3: fetus on day 11; Lane 4: fetus on day 15; and Lane 5: fetus on day 17.

In the mouse fetus, the expression of SELF gene was strongly observed on the 7th embryonal day, whereas the expression was not observed on the 11th, 15th and 17th embryonal days (FIG. 2). SELF gene was also not expressed in the fetal liver (on embryonal days 13 and 14).

The expression of SELF gene was also examined for human various organs by Northern blot analysis using Multiple Tissue Northern Blot #636818 (Clontech) and the mouse SELF cDNA fragment. The results are shown in FIG. 3.

Figure 3:
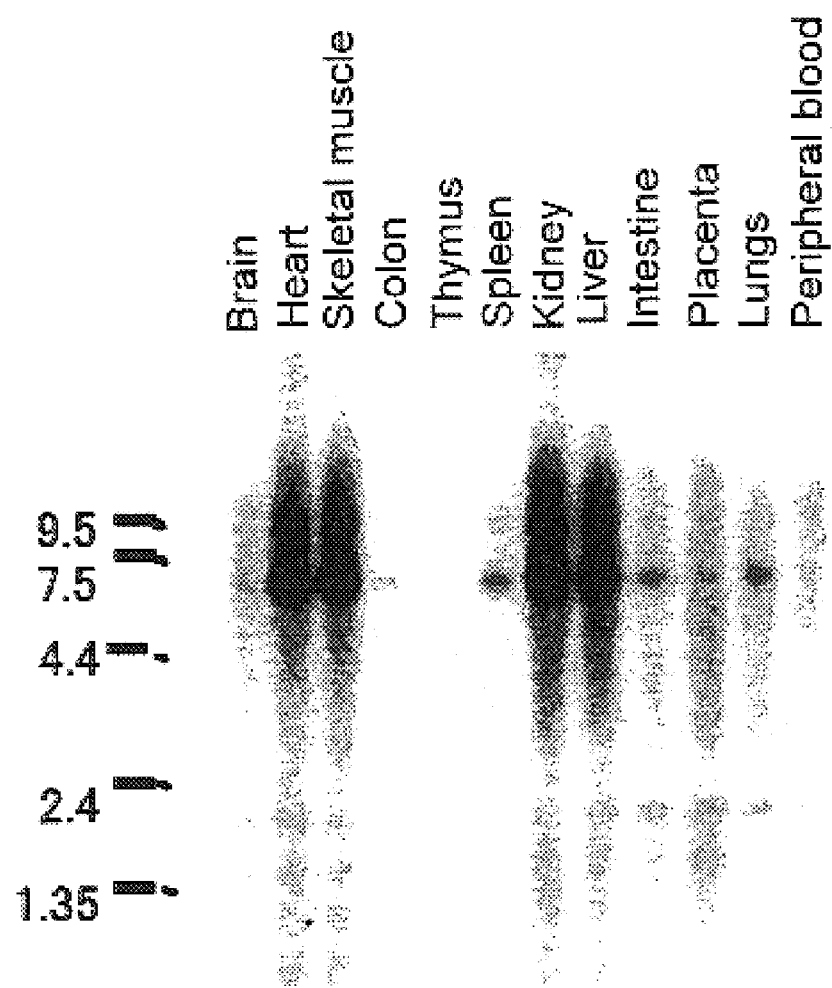
FIG. 3 is a photograph showing the expression of SELF mRNA in human various organs. Each lane indicates samples that were collected from, from left to right, the brain, heart, skeletal muscle, colon, thymus, spleen, kidney, liver, intestine, placenta, lungs, and peripheral blood.

As shown in FIG. 3, SELF gene was strongly expressed in the heart, skeletal muscles, kidney and liver, whereas it was more weakly expressed in the spleen, intestine, and lungs. The two sizes of the human SELF mRNAs, 6.5 kb and 9-9.5 kb, are observed, whereas the size of the mouse SELF mRNA is 9.5-10 kb (approx. 5 kb in the mouse testis). This is thought to be due to an alternative splicing.

Example 5

Production of Antibodies Recognizing E13 Protein

The sequence, CQSTSLRKPKQETK (SEQ ID NO: 20) wherein cysteine was added to the N terminus of the peptide corresponding to the amino acids 1390 to 1403 of SEQ ID NO: 2, was synthesized, and conjugated to KLH via the cysteine of the peptide using Imject Maleimide Activated KLH Kit (Pierce) according to the attached instructions. A rabbit was immunized with 6 mg of this peptide-KLH complex in 4 divided doses. On priming, it was mixed with Freund's complete adjuvant to prepare emulsion, and administered subcutaneously on the back. From the second immunization, it was mixed with Freund's incomplete adjuvant to prepare emulsion, and administered subcutaneously on the back three times every other two weeks. Two weeks after the final administration, exsanguination was performed and the blood serum was separated. An equivalent amount of PBS was added to 10 ml blood serum to dilute it, and the product added to 3 ml Prosep® A column (Bioprocessing). After washing out the unabsorbed substances with 30 ml PBS, the column was eluted with 10 ml of 0.1M glycine buffer (pH 3.0). 0.5 ml of 1M Tris-HCl buffer (pH 8.0) was added to the eluate to neutralize it, and purified rabbit antibody which recognizes SELF protein was thus obtained.

Vector DNA, which was prepared by removing the BamHI recognition site from CDM8 (Invitrogen), was digested with HindIII and XbaI, and the resulting longest DNA fragment was purified by agarose electrophoresis. Next, the oligomer DNAs of AGCTTCCACCATGTCTGCACTTCTGATC- CTAGCTCTTGTTGGAGCTGCAGTTGCT GACTA-
CAAAGACGATGACGACAAGCAC (SEQ ID NO: 14) and
TCGAGTGCTTGTCGTCATCGTCTTTG-
TAGTCAGCAACTGCAGCTCCAACAAGAG CTAGGAT-
CAGAAGTGCAGACATGGTGGT (SEQ ID NO: 15) was annealed each other to produce double-stranded DNA. This DNA has cohensive sites, which correspond those created with HindIII and XhoI digestion, at the ends. This DNA fragment encodes the leader sequence of mouse preprotrypsin and FLAG sequence (Bio/Technology 6, 1204-1210 (1988) Biotechniques 754 (1994)). This DNA fragment was introduced between the HindIII and XhoI sites of the above CDM8 fragment lacking BamHI recognition site to obtain CDM8flag. This CDM8flag was digested with XhoI and XbaI, and the resulting longest fragment was separated by agarose gel electrophoresis. Also, CD4IgG (Zettlmessl et al., DNA Cell Biol. 9, 9125-9129, 1990) was digested with BamHI and XbaI, and the resulting fragment of approx. 1280 bp, which encodes IgGFc, was separated by agarose gel electrophoresis. The DNA fragment encoding IgGFc was ligated to the above CDM8flag fragment, which was obtained by XhoI and XbaI digestion, and thus CDMflagIgG was prepared.

Using PA6 cDNAs prepared in Example 1 as a template, PCR was performed with E13-ATG-2s and E13-Bam-2as primers. The E13-ATG-2s and E13-Bam-2as sequences were as follows:

E13-ATG-2s: CCGCTCGAGAGACATGGCTGAGGTG-
GAGACC (SEQ ID NO: 16)

E13-Bam-2as: CTGGGATCCGGTGAAGGCACCAGG-
TAG (SEQ ID NO: 17)

In E13-ATG-2s, nucleotides 10 to 31 coincide with nucleotides 854 to 882 of SEQ ID NO: 1 in the sequence listing, and an XhoI recognition site (nucleotides 4 to 9) has been artificially added.

In E13-Bam-2as, nucleotides 9 to 27 coincide with the complementary sequence to the sequence of nucleotides 1434 to 1451 of SEQ ID NO: 1 in the sequence listing, and a BamHI recognition site (nucleotides 4 to 9) has been artificially added.

The PCR product was digested with XhoI and BamHI, the resulting DNA fragment of approx. 580 bp was separated by agarose gel electrophoresis. The fragment was introduced into CDMflagIgG digested with XhoI and BamHI. The obtained vector DNA was named CDMflagE13IgG. In this vector, downstream of the cytomegalovirus promoter, mouse preproinsulin leader sequence, Flag sequence, partial sequences of the SELF structural gene (sequence corresponding to amino acid 235 (Asp) to amino acid 432 (Pro) of SEQ ID NO: 2), and the sequence of the Fc part of human IgG, was integrated in-frame (i.e., state with a correct reading frame). Therefore the vector can express the chimeric protein of Flag peptide/SELF/IgGFc in animal cells.

CDMflagE13IgG was introduced into monkey COS-1 cells by the DEAE dextran method.

DEAE Dextran (Pharmacia) and chloroquine (Sigma) were added to a RPMI1640 culture medium containing 20 mM TrisHCl (pH 7.4) and 50 µM 2-mercaptoethanol so that their final concentrations were respectively 400 µg/ml and 100 µM, and 50 µg of CDMflagE13IgG was added per 13 ml of this solution.

Also, COS1 cells were cultured in a 150-square culture flask (Corning Costar) at a split ratio of 1:2 on the day prior to DNA introduction, the culture medium in the flask was removed on the day of DNA introduction and rinsed once with PBS, 13 ml of DNA mixture was added, and culture continued. 4 hours later, the DNA mixture was removed, 50 ml of Hybridoma SFM culture medium (GIBCO) was added, and the culture continued further. After 4 days, the culture medium was collected, 50 ml of Hybridoma SFM culture medium was newly added to the flask, culture continued for four more days, and the culture medium collected. This was ligated into the culture medium collected on the first occasion, the cell debris removed by centrifuging at 3000 rpm for 10 minutes, and the product sterilized by filtration with a 0.2 µm filter. Using the specific binding of IgGFc to Protein A, Protein A immobilized on Prosep® A (Bioprocessing) was used to purify this chimeric protein.

500 ml of this culture medium was added to 1 ml Prosep® A (Bioprocessing) for one day. Next, the unadsorbed substances were washed out with 15 ml PBS, and eluted with 0.1M glycine buffer (pH 3.0). The eluate was collected 1 ml at a time, 0.1 ml of 1M Tris-HCl buffer (pH 8.0) was added to the second fraction which contained the most protein content to neutralize it, and the product dialyzed with PBS. This procedure was performed twice, and 1 mg of the chimeric protein was obtained from the culture medium per litter. 2 µg of this protein was subjected to electrophoresis in 8% SDS polyacrylamide gel, and it was confirmed to have the expected molecular weight.

A rabbit was immunized with 0.8 mg of this chimeric protein in 4 divided doses. On priming, 0.2 mg chimeric protein was mixed with Freund's complete adjuvant to prepare emulsion, and administered subcutaneously on the back. From the second immunization, 0.2 mg the chimeric protein was mixed with Freund's incomplete adjuvant to prepare emulsion, and administered subcutaneously on the back three times every other two weeks. Two weeks after the final immunization, exsanguination was performed and the blood serum was separated. An equivalent amount of PBS was added to 10 ml blood serum to dilute it, and the product added to a 3 ml Prosep® A column (Bioprocessing). After washing out the unadsorbed substances with 30 ml PBS, it was eluted with 10 ml 0.1M glycine buffer (pH 3.0). 0.5 ml of 1M Tris-HCl buffer (pH 8.0) was added to the eluate to neutralize it, and purified rabbit antibody which recognizes flag/E13/IgG chimeric protein was thus obtained.

Example 6

Identification of SELF Protein Expression

It was verified whether SELF protein was actually synthesized as a protein using the two kinds of antibodies produced in Example 5.

Stromal cells PA6, were cultured until confluent in a 150-square culture flask. Next, the product was washed twice with PBS, 50 ml Hybridoma-SFM (GIBCO) was added, and the product cultured for 4 more days. Saturated ammonium sulfate was added to this culture to give 50% saturated ammonium sulfate, and the product allowed to stand overnight at 4° C. to precipitate the protein. Next, the precipitate was centrifuged at 10,000 rpm for 20 minutes, collected, dissolved in 1 ml PBS, and dialyzed twice in 1 L PBS. The dialysis solution was sterilized by filtration with a 0.2 µm filter, and stored at 4° C.

This sample was applied to SDS-polyacrylamide electrophoresis (8% gel) under reducing conditions, and the protein was transferred to Hybond™-ECL cellulose nitrate membrane (Amersham). In this way, two filter sheets on which the protein produced by PA6 cells was blotted, were produced. This filter was blocked by a Block Ace (Snow Brand). One of the filters was treated with 1 µ/ml of the antibody to the C terminus peptide of the SELF protein, and the other was treated with 1 μ/ml of the antibody to flag/E13/IgG chimeric protein. After 1 hour, it was washed 6 times with washing solution, HRP-labeled anti-rabbit IgG antibody (Amersham) diluted 5000 times was added, and after washing thoroughly with washing solution, the proteins recognized by the antibody to SELF C terminus peptide and the antibody to flag/E13/IgG chimeric protein were detected using an Amersham ECL detection kit. As a result, both antibodies recognized approx. 200 kDa of protein. This shows that in PA6, SELF is translated into a protein and secreted. The results are shown in FIG. 4. As shown in the results of the sample (lane 1) obtained by culturing the stromal cells PA6 in the serum-free medium and then concentrating the supernatant 50 times with 50% saturated ammonium sulfate and the supernatant (lane 2) obtained by culturing stromal cells in the medium containing 10% FCS, approximately 200 kDa of the SELF protein could be detected in the case of lane 1.

Moreover, SELF protein expression was examined using the antibody against the SELF C-terminus peptide prepared in Example 5. Specifically, the expression in mouse fetuses on embryonal days 9 and 11 was examined using whole-mount samples. In both samples on embryonal days 9 and 11, the expression was observed in the limb buds and throughout the mesenchymal cells of the face. Regarding blood vessels, the expression was strongly observed in the arteria vitellina (omphalomesenteric membrane arteries) of fetuses on embryonal day 9. Furthermore, the expression was weakly observed also in the anterior cardinal veins of the head. In the cases of both fetuses on embryonal days 9 and 11, the expression was weakly observed also in the heart. Regarding the heart on embryonal day 9, the expression was observed only in the ventricle, indicating that the SELF gene was expressed in cardiac muscle cells. In the case of fetuses on embryonal day 11, the expression was observed in the internal epithelial layer of the intestine and the outermost coat of the intestine.

Example 7

Expression of Recombinant SELF pCI-neo-mSELF obtained in Example 3 was introduced into monkey COS-1 cells by the DEAE dextran method.

DEAE Dextran (Pharmacia) and chloroquine (Sigma) were added to RPMI1640 culture medium containing 20 mM of TrisHCl (pH 7.4) and 50 μM of 2-mercaptoethanol, so that their final concentrations were respectively 400 μg/ml and 100 μM, and 50 μg of pCI-neo-mSELF of 50 μg was added per 13 ml of this solution.

Also, COS1 cells were cultured in a 150 square culture flask (Corning Costar) at a split ratio of 1:2 on the day prior to DNA introduction, the culture medium in the flask was removed on the day of DNA introduction and washed once with PBS, 13 ml of DNA mixture was added, and culture was continued. 4 hours later, the DNA mixture was removed, 50 ml of Hybridoma SFM culture medium (GIBCO) was added, and culture medium was continued further. After 4 days, the culture medium was collected, 50 ml of Hybridoma SFM culture was again added to the flask, the culture medium was continued for 4 more days, and the culture was collected. It was ligated into the culture collected on the first occasion, cell debris were removed by centrifuging at 3000 rpm for 10 minutes, and sterilized by filtration with a 0.2 μm filter. Proteins having a molecular weight of 50,000 or more were concentrated 20 times by applying the culture supernatant to a Centricut (KURABO). This sample was applied to SDS-polyacrylamide electrophoresis (8% gel) under reducing conditions, and the protein was transferred to Hybond-ECL cellulose nitrate membrane (Amersham). The filter was blocked by a Block Ace (Snow Brand), and treated by 1 μg/ml of the antibody to the C-terminus peptide of the SELF protein. After 1 hour, it was washed 6 times with washing solution, HRP-labeled anti-rabbit IgG antibody (Amersham) diluted 5000 times was added, and after washing thoroughly, the protein recognized by the antibody to the SELF C terminus peptide was detected by an Amersham ECL detection kit. As a result, a protein of approximately 200 kDa was recognized. This confirms the production of the SELF protein.

Preparation of Self-Flag Peptide Fusion Protein

For the purpose of preparing a highly purified recombinant SELF protein, a skilled person in the art can generally use a method that comprises adding a tag peptide to the amino terminus or the carboxyl terminus of a target protein and using a carrier to which an antibody against the peptide has been bound. A vector expressing a fusion protein having a Flag peptide as such peptide tag on the SELF carboxyl terminus was constructed. Specifically, p3xflag-CMV-14 (Sigma) was digested with Hind III and Bgl II. The longest fragment containing a CMV promoter was separated by agarose gel electrophoresis and then purified. The resulting fragment, an approximately 4200 bp of SELF cDNA fragment obtained by digesting pCl-neo-mSELF with Hind III and Afe I, and a double-stranded DNA that had been prepared by annealing the two polynucleotides: GCTGCCAGAGCA-CAAGCCTCAGGAAACCCAAACAGGAAACAAAGTC-GATA (SEQ ID NO: 21) and GATCTATCGACTTTGTTTC-CTGTTTGGGTTTCCTGAGGCTTGTGCTCTGGCAGC (SEQ ID NO: 22), were ligated each other with a ligase to produce a vector p3XFLAGCMV14 mSELF that is capable of expressing a SELF-Flag peptide fusion protein. This vector was introduced into monkey COS-1 cells by a DEAE dextran method as above-mentioned. After introduction, the COS-1 cells were cultured for 4 days, and the culture supernatant following 4 days of culture and an anti-Flag peptide antibody-immobilized carriers (M2 agarose; Sigma) were combined and gently stirred for 2 hours at 4° C. Next, the M2 agarose carriers were collected in a chromatography column and then sufficiently washed with a phosphate buffer. 0.1 M glycine (pH 3.5) was added to elute the SELF-Flag peptide fusion protein bound to the M2 agarose carriers from the column. Immediately after elution, a 1 M Tris-HCl buffer (pH 8.0) was added to neutralize the eluate. This sample was subjected to SDS-polyacrylamide electrophoresis (8% gel, TEFCO) under reducing conditions, and the proteins contained in the sample were then transferred to Hybond-ECL nitrocellulose membrane (Amersham). This filter was blocked using a Block Ace (Dainippon Pharmaceutical), followed by treatment with a 10 μg/ml anti-Flag antibody M2 (Sigma) and 1 μg/ml of an antibody against C-terminal peptide of the SELF protein. After 1 hour, the resultants were washed 6 times with a washing solution. An HRP-labeled anti-mouse IgG antibody (Amersham) diluted 5000 times and an HRP-labeled anti-rabbit IgG antibody (Amersham) diluted with 5000 times were added to the resultants. After thorough washing with a washing solution, proteins recognized by the anti-Flag antibody and the antibody against the SELF C terminal peptide were detected using an Amersham ECL detection kit. As a result, both antibodies recognized proteins of approximately the same molecular weight. It was verified from the results that the protein was a SELF-flag peptide fusion protein.

Example 8

Effects of SELF Gene on Hematopoiesis

The effects of the SELF gene on hematopoietic ability were examined through coculture of stromal cells caused to overexpress the SELF gene with differentiation-antigen-negative marrow cells.

p3XFLAGCMV14 mSELF constructed in Example 7 was introduced into a stromal cell line PA6 using lipofectamine 2000 (Invitrogen) according to the manuals for the product. Thus, a clone PA6/SELF-10G overexpressing the SELF gene was obtained.

Differentiation-antigen-positive cells were removed from bone marrow cells using magnetic beads for cell separation (Stem Cells, 19: 71-79, 2001). The stromal cell clone PA6/SELF-10G was cultured in an αMEM medium containing 10% fetal calf serum (FCS, Invitrogen) in a 60 mm dish. $3 \times 10^3$ cells of differentiation-antigen-negative marrow cells were added to the dish and cocultured with the stromal cell clone PA6/SELF-10G. As a control, a non-engineered stromal cell line PA6 and differentiation-antigen-negative bone marrow cells were cocultured by the same method. After 3 weeks of coculture, the number of blood cells derived from the bone marrow that had grown on each PA6 stromal cell line was determined. The number of such blood cells was $5.5 \times 10^3$ in the case of control PA6 cells. In contrast, the number of such blood cells was $1.2 \times 10^5$ in the case of the stromal cells PA6/SELF-10G wherein p3XFLAGCMV14 mSELF had been introduced. Specifically, the number in the case of the stromal cell PA6/SELF-10G was increased to an amount approximately 21 times greater than that in the case of the control PA6. As described above, blood cells that had grown in the coculture of stromal cells with bone marrow cells, was evaluated for their colony forming abilities. Each type of blood cell was cultured at $1 \times 10^4$ cells per 35 mm dish after being added to MethocultGFM3434 (StemCell Technologies) containing EPO, IL-3, SCF, and IL-6. The number of colonies formed on day 4 and that on day 7 after culture were determined. As a result, when the control PA6 were cocultured with bone marrow cells to produce blood cells, 1 colony of blood cell was observed on day 4 and 3 colonies of blood cells were observed on day 7. In contrast, with respect to blood cells that had grown in coculture of bone marrow cells with stromal cells PA6/SELF-10G having p3XFLAGCMV14 mSELF introduced therein, 57 colonies were formed on day 4 and 51 colonies were formed on day 7. These results revealed that stromal cells overexpressing the SELF gene have higher hematopoiesis-supporting ability than that of non-engineered stromal cells. Moreover, the formed colonies were mainly GM colonies (neutrophils and macrophages). Therefore, it was suggested that the SELF gene has an effect of stimulating hematopoiesis.

Example 9

Effects of SELF Protein on Hematopoiesis

Next, the effects of the SELF protein on hematopoietic cells were examined. Bone marrow cells were prepared from a 10-week-old C57BL/6 mouse femur, and then differentiation-antigen-negative cells were separated from them using magnetic beads for cell separation as described above. $1 \times 10^5$ differentiation-antigen-negative bone marrow cells were cultured in the presence or the absence of 100 ng/ml SELF protein in 1 ml of αMEM containing 10% FCS and a cytokine cocktail (10 ng/ml mouse SCF, 10 ng/ml human IL-6, and 10 ng/ml human IL-11) in a 12-well plate. The number of cells was counted every week and $1 \times 10^5$ grown cells were cultured under the same conditions. In the absence of the SELF protein, the number of cells was $6 \times 10^4$ after 5 weeks and hematopoiesis was arrested. In contrast, in the presence of the SELF protein, the number of cells was $2 \times 10^5$ and hematopoiesis was continued. These results revealed that the SELF protein has the ability to support the growth of hematopoietic cells in a long-term culture system for hematopoietic cells.

Furthermore, the colony forming ability of cells cultured with the SELF protein was examined. $2.5 \times 10^5$ differentiation-antigen-negative bone marrow cells were cultured in the presence or the absence of 100 ng/ml SELF protein in 1 ml of αMEM containing 10% FCS and a cytokine cocktail (10 ng/ml mouse SCF, 10 ng/ml human IL-6, and 10 ng/ml human IL-11) in a 12-well plate. Culture was continued under the same conditions using a half of the grown cells removed every 4 to 6 days. After 24 days, the grown cells were added to 1 ml of MethocultGFM3434 (StemCell Technologies) containing EPO, IL-3, SCF, and IL-6 at $1 \times 10^4$ cells per 35 mm dish, and cultured therein. The number of colonies formed after 4 days was counted. The results are shown in Table 1.

TABLE 1

Colony formation test on marrow cells that experienced long-term culture in the presence or the absence of SELF using SCF, IL-6, and IL-11
Number of colonies (colonies) per 10,000 cells

| SELF | Total | Macrophage | Neutrophil-macrophage | Neutrophil |
|---|---|---|---|---|
| None | 31 | 16 | 5 | 9 |
| 100 mg/ml | 80 | 3 | 74 | 3 |

Whereas the total number of colonies formed by marrow cells that were cultured in a medium containing the SELF protein was 80 on average, the total number of colonies formed by marrow cells cultured in a medium containing no SELF protein was 31 on average. Among the entire colonies, whereas the number of neutrophil-macrophage colonies was 74 under conditions in which the SELF protein was contained, the same under conditions with no SELF protein was 5. These results indicate that under conditions in which the SELF protein was contained, cells having colony forming ability can be maintained and these cells are progenitor cells particularly having neutrophil-macrophage colony-forming ability.

Figure 5:
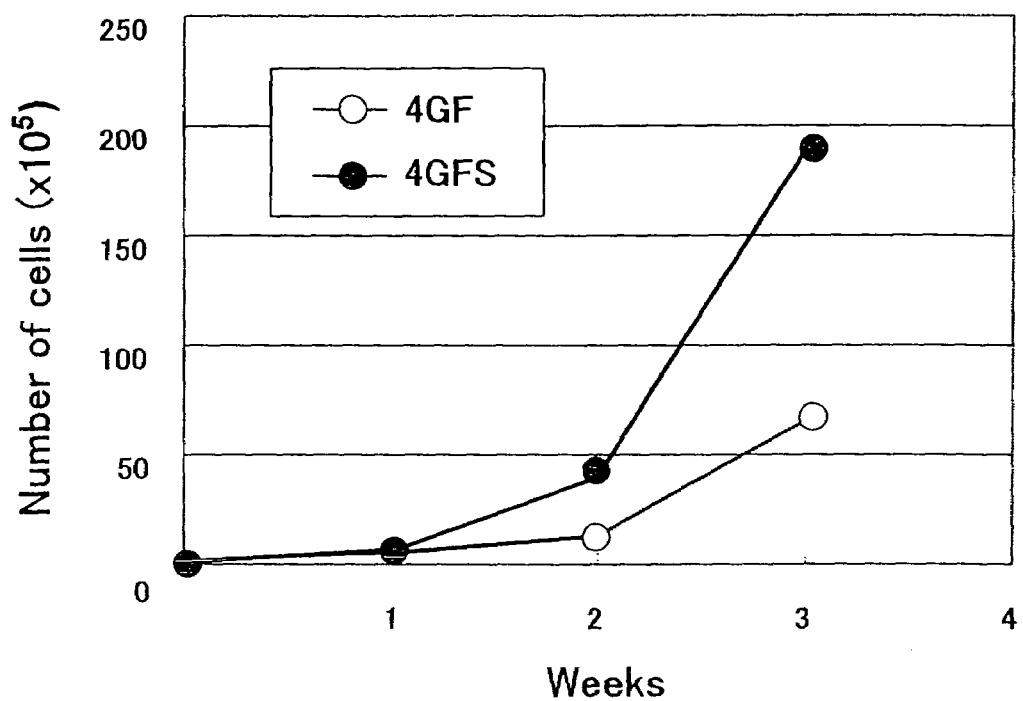
FIG. 5 is a graph showing the effects of the SELF protein on differentiation-antigen-negative marrow cells as examined in Example 9.4GF: mouse SCF+human IL-6+human IL-11+ mouse FLT-3 ligand; and 4GFS: mouse SCF+human IL-6+ human IL-11+mouse FLT-3 ligand+mouse SELF.

Next, $1 \times 10^5$ differentiation-antigen-negative cells prepared from the bone marrow cells of 7-week-old C57BL/6 mice were cultured in the presence or the absence of 100 ng/ml SELF protein in 1 ml of αMEM containing 10% FCS and a cytokine cocktail (10 ng/ml mouse SCF, 10 ng/ml human IL-6, 10 ng/ml human IL-11, and 10 ng/ml mouse Flt-3 ligand) in a 12-well plate. The number of cells was calculated every week and $1 \times 10^5$ grown cells were cultured under the same conditions. The accumulated number of cells over 3 weeks is shown in FIG. 5. 3 weeks later, the accumulated number of cells cultured in the presence of the SELF protein was $1.9 \times 10^7$, whereas the accumulated number of cells cultured in the absence of the SELF protein was $6.5 \times 10^6$. This indicates that SELF promotes the growth of marrow cells by approximately 2.9 times.

Example 10

Effects of SELF Protein on the Growth and Differentiation of Smooth Muscle Cells As attempts for in vitro induction of parietal cells from smooth muscle progenitor cells, a model using a neural crest cell line (Jain, M K. et al., J. Biol. Chem. 273: 5993-5996, 1998), a model using mouse-fetus-derived undifferentiated mesenchymal cells (Yang, Y., et al., Development 126: 3027-3033, 1999), an ES cell model (Yamashita, J. et al., Nature 408: 92-96, 2000), and a P-Sp model (Takakura, N. et al., Immunity 9: 677-686, 1998) have been reported.

In the case of the P-Sp model, through coculture of tissue specimens of the para-aortic splanchnopleural mesoderm (P-Sp) region of a mouse fetus with a stromal cell line OP9 at 37° C., the development and growth of hematopoietic stem cells, the vasculogenesis of vascular endothelial cells, the recruitment of smooth muscle cells, and angiogenesis that takes place while being surrounded by parietal cells containing these smooth muscle cells were observed (Takakura et al., Immunity 9: 677-689, 1998; Takakura et al., Cell 102: 199-209, 2000). The effects of the SELF protein on the growth and differentiation of smooth muscle cells and angiogenesis were examined using the above experimental models in the presence or the absence of the SELF protein.

First, the SELF-Flag peptide fusion protein prepared in Example 7 was added as the SELF protein at a concentration of 100 ng/ml to an RPMI1640 medium (produced by Invitrogen) supplemented with 10% FCS (Invitrogen), 10 µM of 2 ME (Sigma), IL-6 (20 ng/ml; R&D System), IL-7 (20 ng/ml; R&D System), SCF (50 ng/ml; R&D System), and Epo (2 U/ml; KIRIN BREWERY COMPANY, LIMITED). P-Sp tissue specimens derived from C57BL6 mice (SCL) between embryonal days 8.5 and 9.5 were cocultured with the stromal cell line OP9 (RIKEN Cell Bank no. RCB1124) in the thus prepared medium. In a control experiment, P-Sp tissue specimens were cocultured with the stromal cell line OP9 in the same manner, except that no SELF protein was added to a medium. Angiogenesis was observed on day 10 after the start of culture. In the presence of the SELF protein, the formation of a sheet-like structure (vascular bed) by vascular endothelial cells was observed. However, the recruitment of smooth muscle cells and vascular network formation were not observed (FIG. 6B). In contrast, in the absence of the SELF protein, tubular vascular network formation was observed (FIG. 6A). These results indicate that the SELF protein inhibits the growth and differentiation of smooth muscle cells from undifferentiated cells contained in P-Sp, so as to inhibit angiogenesis.

Example 11

Effects of SELF Gene on Tumorigenesis

The effects of the SELF gene on malignant tumors were examined. The vector p3XFLAGCMV14 mSELF (expressing a SELF-Flag peptide fusion protein) constructed in Example 7 was introduced into a mouse colon cancer cell line colon26 (Brattain, M G., et al., Cancer Res. 40: 2142-2146, 1980), thereby preparing colon26 cells expressing the SELF gene (hereinafter referred to as SELF/colon26). In the meantime, a vector mFlt-1-hIgG1 (Hirashima, M., et al., Blood 93: 1253-1263, 1999) expressing a Flt1-Fc protein (chimeric protein comprising a soluble VEGF receptor and a human IgG1 constant region (Fc)) that was capable of inhibiting a vascular endothelial growth factor (VEGF) was introduced into colon26 cells, thereby preparing colon26 cells expressing a Flt1-Fc gene (hereinafter referred to as Flt-Fc/colon26). For introduction of the vectors into the cells, lipofectamine 2000 (Invitrogen) was used according to the manuals of the product.

Subsequently, a colon26 cell line, a SELF/colon26 cell line, and a Flt1-Fc/colon26 cell line were examined for proliferative ability. Each cell line ($1 \times 10^5$ cells each) was cultured in 2 ml of RPMI1640 medium containing 10% FCS using 4 wells of a 6-well plate. The number of cells was calculated d using a hemacytometer 4 days after the start of culture. The average number of the cells of each cell line cultured in the 4 wells was $2.18 \times 10^6$ in the case of Colon26, $2.22 \times 10^6$ in the case of SELF/colon26, and $2.18 \times 10^6$ in the case of Flt1-Fc/colon26. No significant differences were observed in terms of the proliferative ability of these 3 types of cell line (Table 2). With these results, it was confirmed that the expression of the SELF gene and that of the Flt1-Fc gene have no direct effects on colon26 cells' own growth.

TABLE 2

Comparison of in vitro proliferative ability of colon26 cells expressing SELF gene or Flt1-Fc gene

| Well | Number of cells ($\times 10^4$) | | |
|---|---|---|---|
| | Colon26 | Flt1-Fc/colon26 | SELF/colon26 |
| 1 | 232.5 | 224.3 | 234 |
| 2 | 221.3 | 220.5 | 213.8 |
| 3 | 209.3 | 194.5 | 234 |
| 4 | 210 | 232.3 | 208.5 |
| Average | 218.275 | 217.9 | 222.575 |

Next, $2 \times 10^6$ colon26 cells, Flt1-Fc/colon26 cells, SELF/colon26 cells, and a cell mixture containing $1 \times 10^6$ SELF/colon26 cells and $1 \times 10^6$ Flt1-Fc/colon26 cells were each subcutaneously transplanted to ten 8-week-old Balb/c male mice. The mice test groups were referred to as a colon26-transplanted group, a Flt1-Fc/colon26-transplanted group, a SELF/colon26-transplanted group, and a SELF/colon26+Flt1-Fc/colon26-transplanted group, respectively; each group consisting of 10 mice. On day 14 after transplantation, tumor sizes were compared. Tumor volume was estimated according to the following formula (Iwanuma, Y., et al., Cancer Immunol Immunother. 40: 17-23, 1995):

$$V = ab^2 \pi / 6$$

wherein, a=longest diameter (mm) of tumor and b=width (mm) of tumor (the longest diameter and the width of a tumor were measured using vernier calipers).

Figure 7:
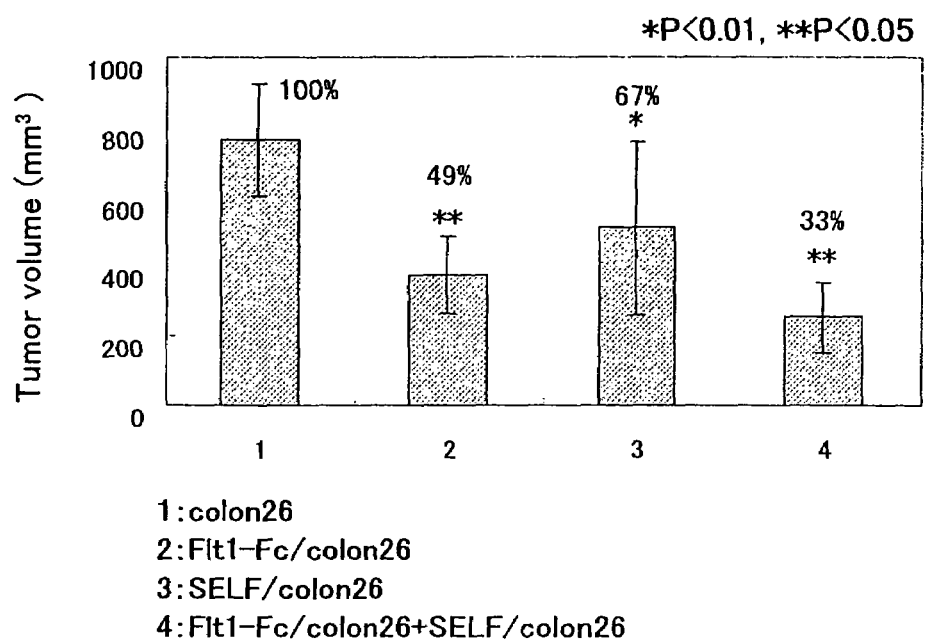
FIG. 7 is a graph showing the in vivo ability of tumorigenesis of colon26 cells, Flt1-Fc gene-expressing colon26 cells, SELF gene-expressing colon26 cells, and cell mixture prepared by mixing Flt1-Fc gene-expressing colon26 cells and SELF gene-expressing colon26 cells at a ratio of 1:1, as examined in Example 11. 1: Colon26 cells; 2: Flt1-Fc gene-expressing colon26 cells; 3: SELF gene-expressing colon26 cells; and 4: Cell mixture prepared by mixing Flt1-Fc gene-expressing colon26 cells and SELF gene-expressing colon26 cells at a ratio of 1:1.

The results are shown in FIG. 7. Tumor sizes were compared using the tumor volume of the colon26-transplanted group as 100%. The tumor volume of the SELF/colon26-transplanted group was 67% and that of the Flt1-Fc/colon26-transplanted group was 49%. It was indicated that in the cases of the Flt1-Fc/colon26-transplanted group and the SELF/colon26-transplanted group, tumorigenesis was significantly inhibited. Furthermore, the tumor volume of the SELF/colon26+Flt1-Fc/colon26-transplanted group was 33% compared with that of the colon26-transplanted group, indicating significantly inhibited tumor growth. Accordingly, it was shown that the SELF protein exerts strong inhibitory effects against tumor growth when it is used in combination with a molecule such as the Flt1-Fc protein having inhibiting effects on the growth of vascular endothelial cells.

As described above, it was shown that the SELF protein does not have a direct effect on tumors, but inhibits angiogenesis by inhibiting the growth and differentiation of smooth muscle cells, which are required for tumorigenesis, so as to inhibit tumor growth in hosts.

Example 12

Cloning of Human SELF cDNA

The NCBI database was searched based on the nucleotide sequence information of SEQ ID NO: 1, revealing that a region having high homology with a mouse SELF cDNA is present on human chromosome 2. Based on detailed comparison between this nucleotide sequence of human genome region and the mouse SELF cDNA sequence of SEQ ID NO: 1, the nucleotide sequence shown in SEQ ID NO: 23 was predicted to be a human SELF cDNA. Furthermore, the amino acid sequence predicted from SEQ ID NO: 23 is shown in SEQ ID NO: 24. Whether or not the predicted sequence is actually transcribed into mRNA was verified as described below.

cDNA was synthesized from 1 μg of human spleen mRNA (Becton, Dickinson and Company) using reverse transcriptase SuperScriptII (Invitrogen). 1 μg of human spleen mRNA was dissolved in 10 μl of distilled water and then 1 μl of 0.5 μg/μl oligo-(dT) was added, followed by 10 minutes of heating at 70° C. Next, the solution was cooled on ice for 2 minutes. 200 units of reverse transcriptase SuperScriptII, and 4 μl of a 5× first-strand reaction solution, 2 μl of a 0.1 M DTT solution, and 2 μl of a 10 mM dNTPs mixture that are attached to the reverse transcriptase were added and the final volume was adjusted to 20 μl using distilled water. The solution was incubated at 45° C. for 1 hour and then at 55° C. for 30 minutes, so that cDNA was synthesized. 5 μl of a 10× buffer, 5 μl of a 2 mM dNTPs mixture attached to Advantage 2 Polymerase Mix (Pharmacia), 1 μl of 10 μM primer human SELF-s2 (CCAAGGACCGCTGCGTGGTG: SEQ ID NO: 25), and 1 μl of primer human SELF-as8 (TTAA-GATTTCACCAGTGTCAGACTC: SEQ ID NO: 26) were added to 1 μl of the synthesized cDNA as a template, and finally, deionized water was added to a total volume of 49 μl. Next, 1 μl of Advantage 2 Polymerase Mix (Becton, Dickinson and Company) was added. PCR reaction was performed under the following conditions: 94° C. for 4 minutes; 35 cycles of 94° C. for 1 minute, 68° C. for 2 minutes, and 72° C. for 3 minutes; followed by the final extension at 72° C. for 7 minutes, and then hold at 4° C.

When aliquots of the resultant PCR product were subjected to agarose gel electrophoresis, an amplification product of approximately 4.0 kb was confirmed. Hence 2 μl of the PCR product was ligated to pCR2.1-TOPO (Becton, Dickinson and Company). *Escherichia coli* were transformed according to a standard method using the resultant clone, and a plasmid DNA was prepared from the thus obtained transformant. Insertion of a DNA fragment of approximately 4 kb was confirmed by digestion with EcoR I, and then the cloned DNA fragment was sequenced. As a result, the nucleotide sequence of cloned DNA coincided with the sequence of nucleotides 84 to 4235 of SEQ ID NO: 23. A vector retaining the DNA fragment was named pCR2.1-TOPO-hSELF5'.

Next, 1 μg of human spleen mRNA was dissolved in 10 μl of distilled water and then 1 μl of 2 μM human SELF-specific primer, human SELF-R1034 (ACACTCTTTGGTGTCA-CAGGGGGATTGGGCTGTCTCACAGG: SEQ ID NO: 27) was added, followed by 2 minutes of heating at 70° C. Next, the solution was cooled on ice for 2 minutes. 200 units of reverse transcriptase SuperScriptII; 4 μl of a 5× first-strand reaction solution, 2 μl of 0.1 M DTT solution, and 2 μl of a 10 mM dNTPs mixture attached to the reverse transcriptase were added, and the final volume was adjusted to 20 μl using distilled water. The solution was incubated at 42° C. for 1 hour and then at 55° C. for 30 minutes, thereby synthesizing cDNA. 1 μl of the thus synthesized cDNA as a template, and 10 μl of a 5× buffer, 10 μl of Advantage GC-Melt, 5 μl of a 2 mM dNTPs mixture attached to Advantage GC2 Polymerase Mix (Becton, Dickinson and Company), 1 μl of 10 μM primer human SELF-s1 (ATGCGGCACGGCGTCGCCTG: SEQ ID NO: 28), and 1 μl of primer human SELF-as2 (AAGGT-CACTCGGTACCAGGTGG: SEQ ID NO: 29) were added. Finally, deionized water was added to a total volume of 49 μl. Next, 1 μl of Advantage GC2 Polymerase Mix (Becton, Dickinson and Company) was added. PCR reaction was performed under the following condition: 94° C. for 4 minutes, 35 cycles of 94° C. for 1 minute, 66° C. for 2 minutes, and 72° C. for 3 minutes, followed by the final extension at 72° C. for 7 minutes, and then hold at 4° C. When an aliquot of the resultant PCR product were subjected to agarose gel electrophoresis, an amplification product of approximately 480 bp was confirmed. 2 μl of the PCR product was ligated to pCR2.1-TOPO (Becton, Dickinson and Company). *Escherichia coli* was transformed according to a standard method using the resultant, so that a plasmid DNA was prepared from the thus obtained transformant. Insertion of a DNA fragment of approximately 480 bp was confirmed by digestion with EcoR I, and then the DNA fragment was sequenced. As a result, the nucleotide sequence coincided with the sequence of nucleotides 1 to 476 of SEQ ID NO: 23. A vector retaining the DNA fragment was named pCR2.1-TOPO-hSELF3'.

As described above, it was demonstrated that a gene predicted from the genomic sequence containing the nucleotide sequence of SEQ ID NO: 23 is actually expressed in human cells. Specifically, it was revealed that the nucleotide sequence shown in SEQ ID NO: 23 is a human SELF cDNA. The NCBI nucleic acid database was searched using the nucleotide sequence shown in SEQ ID NO: 23. The sequence of accession No. XM_059482 (FLJ00133 protein) was identified as a gene having high homology. Regarding the nucleotide sequence of XM_059482, it is additionally described that this sequence information was obtained only by computerized analysis from human genome information. It is also described that whether or not the sequence coincides with an actual mRNA sequence and its biological activity are unknown. Comparison of the nucleotide sequence of SEQ ID NO: 23 with the nucleotide sequence of No. XM_059482 revealed that in the XM_059482 sequence, the nucleotide sequence shown in SEQ ID NO: 30 had been inserted between nucleotides 213 and 214 of SEQ ID NO: 3. That is, the XM_059482 sequence differs from the actual SELF mRNA sequence. Therefore, the transcription product comprising the nucleotide sequence of SEQ ID NO: 23 exists in nature, and is a nucleic acid having a sequence that differs from the known sequence of accession No. XM_059482.

Example 13

Cloning of SELF Genomic Gene

By the use of the gene sequence information of the nucleotide sequence of nucleotides 1624 to 2174 of SEQ ID NO: 1, a BAC genomic library (Genome Systems) derived from mouse ES cells 129Svj was screened by a hybridization method. Thus, 3 types of positive clone were obtained. These 3 clones were digested with restriction enzymes and then electrophoresis was performed. Based on their electrophoresis patterns, bands commonly observed among the 3 clones, bands commonly observed among 2 clones, and unique bands observed in only 1 clone were analyzed. As a result, a clone was selected and it was concluded to be the longest genomic DNA containing many unique bands in addition to bands commonly observed among the 3 clones.

Figure 8:
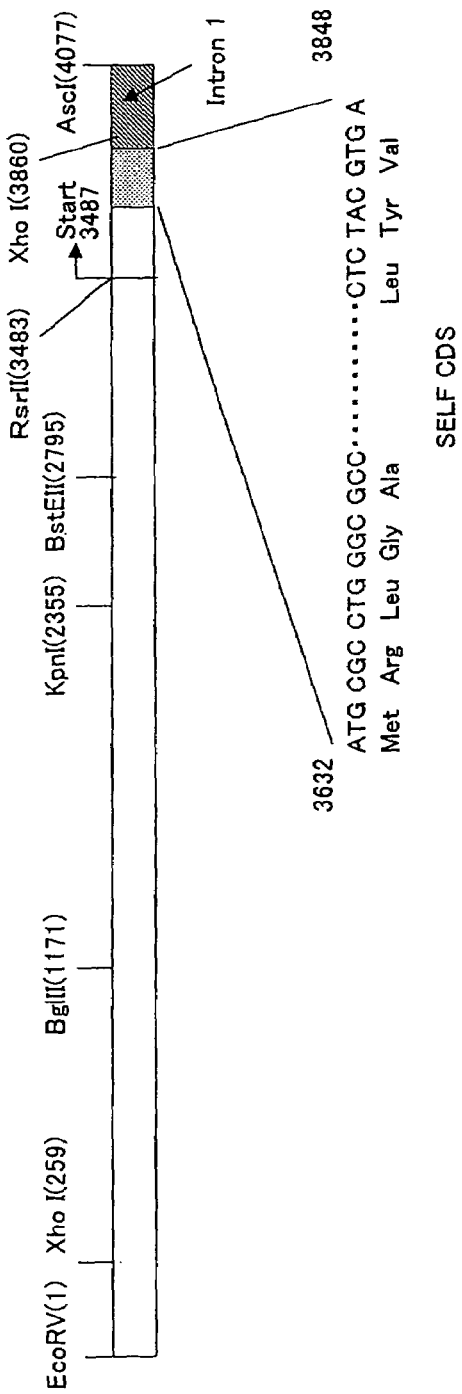
FIG. 8 is a restriction enzyme map showing a SELF genome portion prepared in Example 13.

The GenBank (http://www.ncbi.nlm.nih.gov/Entrez) database was searched by BLASTN for a gene having homology with the SELF gene using the gene sequence information of the nucleotide sequence of nucleotides 20 to 370 of SEQ ID NO: 1. As a result, the genome corresponding to Map element No. NT_039173 having 100% homology with the SELF gene was identified. The restriction enzyme map of the genomic DNA sequence was produced (FIG. 8). It was thus inferred that an expression control region of the SELF gene is present between EcoR V and Asc I. Hence, the previously selected BAC clone DNA containing a mouse SELF genomic gene fragment was digested with EcoR V and Asc I. The thus obtained DNA fragment of approximately 4 kb was cloned into an EcoR V-Asc I site of a vector that had been constructed through conversion of the EcoR I site of pT-AdV (Clontech) into an Asc I site. As a result of sequencing, it was confirmed that in the thus obtained clone a DNA containing a SELF gene exon 1 portion had been cloned. It was inferred that an expression control region of the SELF gene is present upstream of the clone containing exon 1. This clone was named pT-AdV-Self-P. When the nucleotide sequence of the DNA fragment cloned into pT-AdV-Self-P was compared with a sequence on the database, they differed in 3 nucleotides and 15 gaps were present. It was inferred that these differences were due to different origins, such that the DNA used in this experiment was derived from a 129Svj mouse whereas the sequence on the database was derived from a C57/B1 mouse.

Example 14

Examination of SELF Promoter Region

A motif of gene expression control was examined using TFSEARCH (http://www.cbrc.jp/htbin/) and MOTIF (http://motif.genome.adjp/). As a result, it was shown that the SELF promoter does not contain the typical TATA box and CAAT box and is a type of promoter having a C- and G-rich region referred to as CpG island (nucleotide sequence represented by nucleotides 3292 to 3487 of SEQ ID NO: 31).

Comparison with the SELF cDNA sequence (SEQ ID NO: 1) revealed that the $3487^{th}$ nucleotide of SEQ ID NO: 31 is the transcription start position, such that nucleotides 3632 to 3634 correspond to the initial methionine codon of the SELF gene and that the $1^{st}$ intron begins from nucleotide 3849. Specifically, the SELF promoter region containing a transcriptional regulatory sequence was thought to range from nucleotides 1 to 3487 in SEQ ID NO: 31. Furthermore, as a result of detailed examination of transcription factor binding sequences existing in the SELF promoter region, the following binding sequences were confirmed to be present. A C/EBPβ (CCAAT/Enhancer Binding Proteins) binding sequence is present between nucleotides 1590 and 1603, between nucleotides 2402 and 2415, between nucleotides 2456 and 2469, and between nucleotides 2744 and 2757 in SEQ ID NO: 31. A sequence having an NF-kappaB binding sequence is present between nucleotides 8 and 17, between nucleotides 830 and 839, and between nucleotides 2581 and 2590 in SEQ ID NO: 31. A MyoD (myoblast determining factor) binding sequence is present between nucleotides 92 and 101, between nucleotides 727 and 736, between nucleotides 810 and 819, between nucleotides 1053 and 1062, between nucleotides 2047 and 2056, between nucleotides 2509 and 2518, and between nucleotides 2831 and 2840 in SEQ ID NO: 31. An AML-1a (runt-factor AML-1) binding sequence is present between nucleotides 411 and 416, between nucleotides 437 and 442, between nucleotides 971 and 976, between nucleotides 1606 and 1611, between nucleotides 1881 and 1886, between nucleotides 2233 and 2238, between nucleotides 2317 and 2322, and between nucleotides 3002 and 3007 in SEQ ID NO: 31. An Oct-1 (octamer binding factor 1) binding sequence is present between nucleotides 2472 and 2488 and between nucleotides 3052 and 3065 in SEQ ID NO: 31.

Example 15

Construction of Vector Containing SELF Gene Promoter Region

Figure 9:
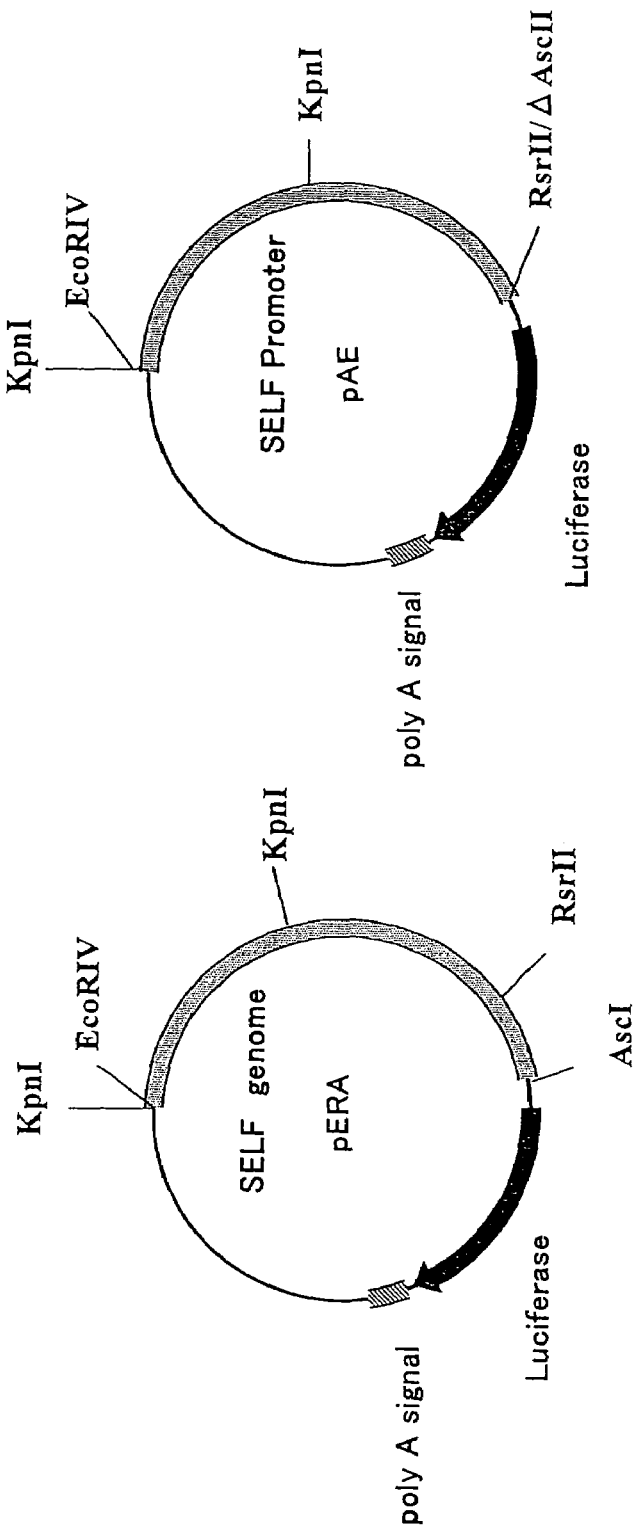
FIG. 9 shows the structures of vectors constructed in Example 15.

A vector containing a promoter region was constructed in order to confirm that the region inferred in Example 14 has promoter activity by luciferase assay. A plasmid pGL3-Basic (Promega) using firefly luciferase as a reporter was used as a basic vector. A vector was constructed through conversion of a Bgl II site of pGL3-Basic to an Asc I site and conversion of a Sac I site of pGL3-Basic to an EcoR V site. A DNA fragment of approximately 4 kb that had been obtained by digesting pT-AdV-Self-P with EcoR V and Asc I was inserted between the EcoR V site and the Asc I site. The vector was named pERA. Next, the vector was digested with Asc I and Rsr II, so as to remove a SELF structural gene region. The DNA ends of the vector were blunted with T4 DNA polymerase and then the vector was self-ligated (self-circularized). The vector was named pAE (FIG. 9). pAE is the vector having the nucleotide sequence (of nucleotides 1 to 3487 of SEQ ID NO: 31) located upstream of the luciferase gene.

Example 16

Construction of Vector Lacking SELF Promoter Region

Figure 10:
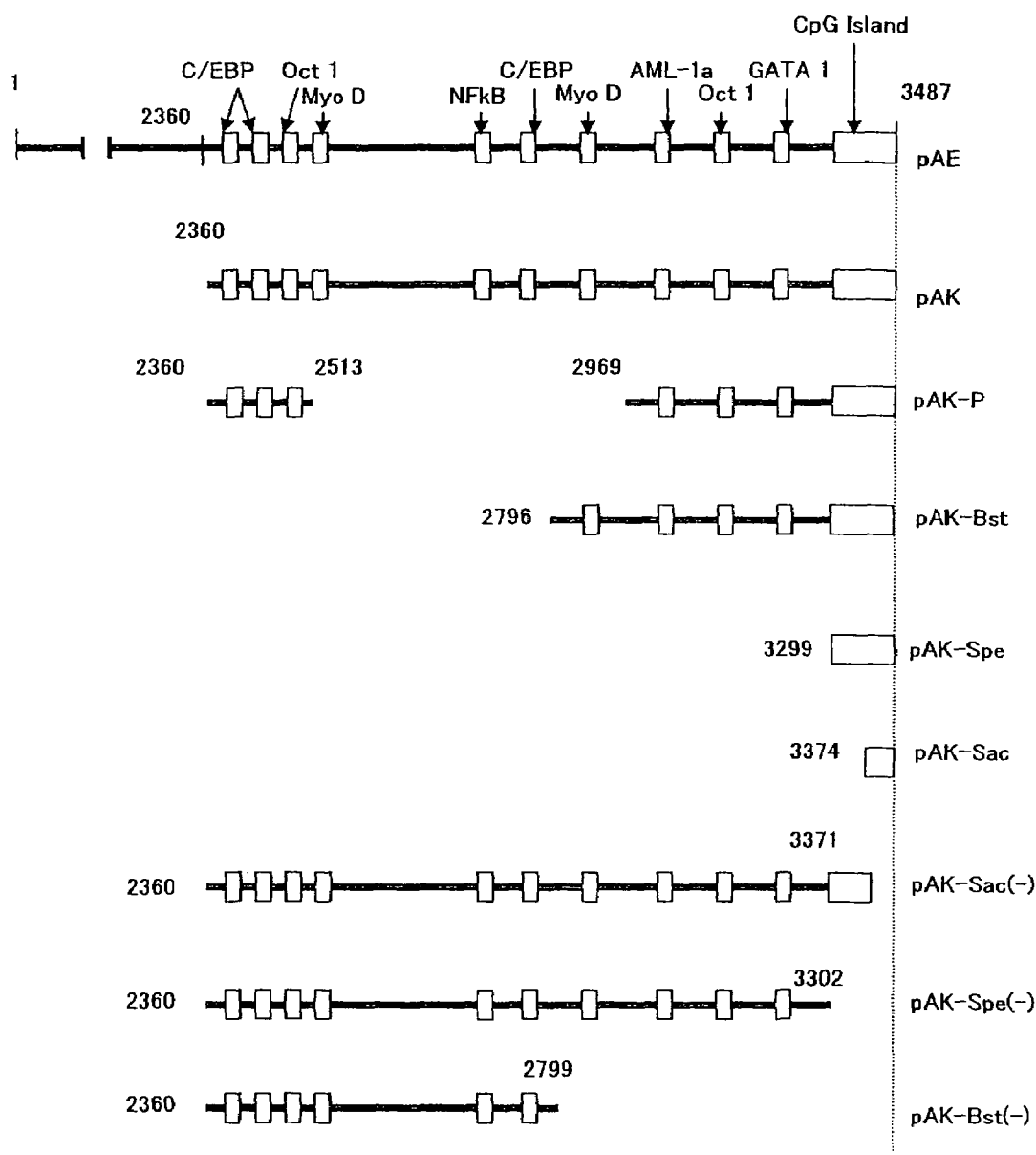
FIG. 10 shows the structures of vectors lacking the SELF promoter, as constructed in Example 16. This figure shows the positions of major transcription factor binding sequences as examined in Example 2. Each numerical value in the figure indicates a nucleotide number of SEQ ID NO: 31.

The vector pAE constructed in Example 15, wherein the SELF promoter region had been cloned, was digested with Kpn I, so as to remove a fragment of approximately 2.3 kb. The vector was self-ligated (self-circularized) and then named pAK. Next, pAK was digested with Kpn I and Spe I and then blunt-ended with T4 polymerase. The resultant was then circularized. The vector was named pAK-Spe. Furthermore, pAK was digested with Kpn I and Sac II and then blunt-ended with T4 polymerase. The resultant was circularized. The vector was named pAK-Sac. Next, pAK was digested with Kpn I and BstE II and then blunt-ended with T4 polymerase. The resultant was circularized. The vector was named pAK-Bst. Moreover, pAK was digested with Pvu II and then the resultant was circularized. The vector was named pAK-P. To construct a vector from which a CpG island has been removed, pAK was digested with Rsr II and Sac II and then blunt-ended with T4 polymerase. The resultant was circularized. The vector was named pAK-Sac(−). Next, pAK was digested with Rsr II and Spe I and then blunt-ended with T4 polymerase. The resultant was circularized. The vector was named pAK-Spe(−). pAK was digested with Rsr II and BstE II and then blunt-ended with T4 polymerase. The resultant was circularized. The vector was named pAK-Bst(−). Which portions of the SELF gene promoter region are possessed by which vectors is summarized in FIG. 10.

Example 17

Measurement of Promoter Activity

Mouse myoblast C2C12 (obtained from RIKEN GENE BANK RIKEN Cell Bank) were suspended at $3 \times 10^5$ cells/ml in a D-MEM medium (Invitrogen) containing 15% FCS (Invitrogen). The prepared C2C12 cells were added to a 25 cm² culture flask (Corning Costar) at 10 ml/flask and then cultured overnight at 37° C. under 5% $CO_2$.

On the next day, the culture solution was removed. 5 ml of a D-MEM medium containing no antibiotic but containing 15% FCS was newly added to continue culture. In the meantime, 8 µl of a vector (1 µg/µl) for promoter activity evaluation containing a reporter gene was added to 492 µl of a serum-free OptiMEM medium containing no antibiotic. 25 µl of Lypofect Amine 2000 (Invitrogen) was added to 475 µl of a serum-free OptiMEM medium containing no antibiotic (Invitrogen). These two samples were mixed and then the mixture was allowed to stand at room temperature for 20 minutes. 1 ml of the sample obtained by mixing was added to the cultured cells, followed by 24 hours of culture.

Figure 11:
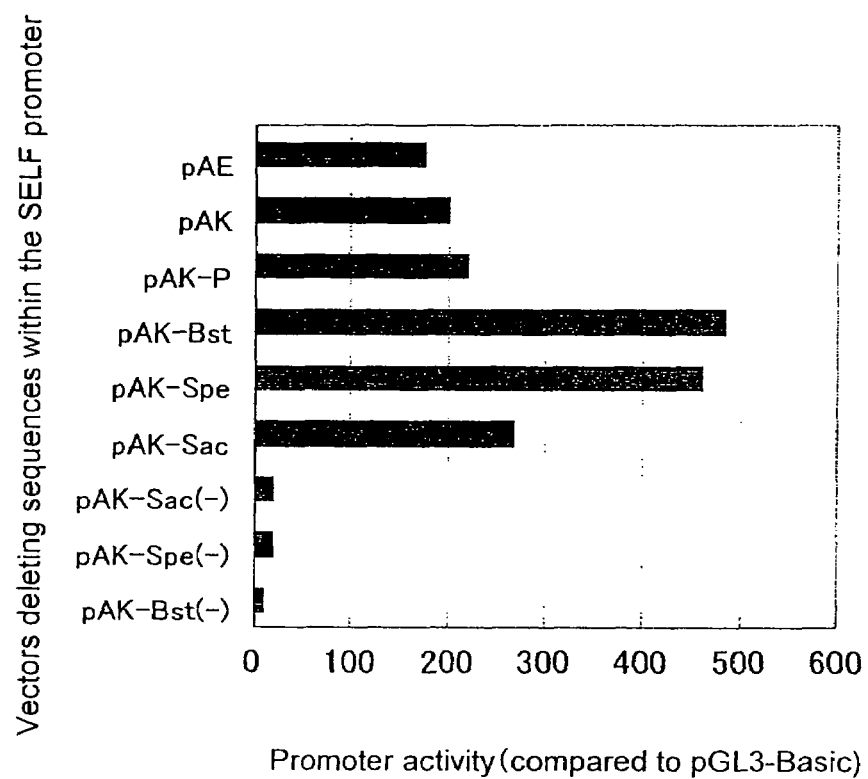
FIG. 11 is a graph showing luciferase activity as measured in Example 17.

After culture, the cells were peeled off from the flask using PBS (NISSUI) containing 0.05% trypsin (Sigma) and 0.5 mM EDTA (Nacalai Tesque). After counting the cells, the cells were prepared to a concentration of $2.8 \times 10^5$ cells/ml using a D-MEM medium containing 15% FCS. The prepared C2C12 cells were added at 180 µl/well to a 96-well plate (Corning Coaster) ($5 \times 10^4$ cells/well) and then cultured overnight at 37° C. under 5% $CO_2$. On the next day, media in the wells were removed by suction. 1×PLB (Passive Lysis Buffer: Promega) was then added at 50 µl/well. The plate was shaken using a plate shaker for 30 minutes so that extraction was performed. The extract was transferred at 10 µl/well to a 96-well white plate (SUMITOMO BAKELITE) for luminescence measurement. Furthermore, a luminescent reagent was added at 50 µl/well. The luminescence level was measured using a luminometer TROPIX (PE systems). As vectors for promoter activity evaluation, a vector pGL3-Basic (produced by Promega) containing a firefly luciferase gene and pAE, pAK, pAK-P, pAK-Bst, pAK-Spe, pAK-Sac, pAK-Sac(−), pAK-Spe(−), and pAK-Bst(−) constructed in the above examples were used. Assay was performed for each vector with n=6 and each average value was found. The results are shown in FIG. 11. The activity in the cases of pAK-Bst, pAK-Spe, and pAK-Sac was higher than that in the case of pAK. Hence, it was discovered that a control region that inhibits promoter activity is present between nucleotides 2513 and 2969 in SEQ ID NO: 31. Furthermore, the activity in the cases of pAK-Sac(−), pAK-Spe(−), and pAK-Bst(−) was significantly lower than that in the case of pAK. Hence, it was revealed that a region exerting the highest promoter activity is present in a region of pAK-Bst; that is, between nucleotides 2796 and 3487 in SEQ ID NO: 31. Moreover, the activity in the case of pAK-Spe was slightly lower than that in the case of pAK-Bst. Hence, it could be inferred that a basic promoter is present in the CpG island region (between nucleotides 3299 and 3487 in SEQ ID NO: 31). Furthermore, the activity in the case of pAK-Sac was lower by approximately 40% compared with that in the case of pAK-Bst. It was thus revealed that a region between nucleotides 3374 and 3487 in SEQ ID NO: 31 can also function as a promoter.

All publications cited herein are incorporated by reference in their entities. It will also be readily understood by those skilled in the art that various modifications and variations of the present invention can be made without departing from the spirit and scope of the invention as defined by the appended claims. Such modifications and variations are intended to be included in the present invention.

---

What is claimed is:

1. An isolated promoter comprising nucleotides 3374 to 3487 of SEQ ID NO:31.

2. An isolated promoter consisting of a nucleotide sequence of nucleotides 3374 to 3487 of SEQ ID NO: 31.

3. An isolated promoter comprising a nucleotide sequence of nucleotides 3299 to 3487 of SEQ ID NO: 31.

4. The isolated promoter of claim 1, wherein the promoter comprises a nucleotide sequence of nucleotides 2796 to 3487 of SEQ ID NO: 31.

5. A recombinant vector comprising the promoter of claim 1.

6. The recombinant vector of claim 5 comprising a structural gene under the expression control of said promoter.

7. The recombinant vector of claim 5 further comprising a viral enhancer sequence inserted adjacent to said promoter.

8. An isolated cell transformed with the recombinant vector of claim 5.

9. A kit for screening for a substance that enhances or inhibits a SELF promoter activity comprising the isolated transformed cell of claim 8.

* * * * *